United States Patent
Pfleger et al.

(10) Patent No.: US 10,982,240 B2
(45) Date of Patent: Apr. 20, 2021

(54) PRODUCTION OF POLYHYDROXY ALKANOATES WITH A DEFINED COMPOSITION FROM AN UNRELATED CARBON SOURCE

(71) Applicant: WISCONSIN ALUMNI RESEARCH FOUNDATION, Madison, WI (US)

(72) Inventors: Brian Frederick Pfleger, Madison, WI (US); Daniel E. Agnew, Brookfield, WI (US)

(73) Assignee: WISCONSIN ALUMNI RESEARCH FOUNDATION, Madison, WI (US)

( * ) Notice: Subject to any disclaimer, the term of this patent is extended or adjusted under 35 U.S.C. 154(b) by 265 days.

(21) Appl. No.: 15/915,964

(22) Filed: Mar. 8, 2018

(65) Prior Publication Data

US 2018/0201961 A1    Jul. 19, 2018

Related U.S. Application Data

(63) Continuation of application No. 13/833,230, filed on Mar. 15, 2013, now abandoned.

(Continued)

(51) Int. Cl.
*C12N 1/20* (2006.01)
*C12P 7/62* (2006.01)
(Continued)

(52) U.S. Cl.
CPC .................. *C12P 7/62* (2013.01); *C12N 1/20* (2013.01); *C12N 9/0006* (2013.01);
(Continued)

(58) Field of Classification Search
None
See application file for complete search history.

(56) References Cited

U.S. PATENT DOCUMENTS 4,837,148 A   6/1989   Cregg
4,929,555 A   5/1990   Cregg et al.
(Continued)

FOREIGN PATENT DOCUMENTS

EP            238023        3/1987
WO        WO 96/00787       1/1996
WO      WO 2013/106464 A1   7/2013

OTHER PUBLICATIONS

Li et al., "A novel-designed *Escherichia coli* for the production of various polyhydroxyalkanoates from inexpensive substrate mixture", Applied Microbiology and Biotechnology, vol. 75, pp. 1103-1109, 2007 (Year: 2007).*

(Continued)

*Primary Examiner* — Richard C Ekstrom
(74) *Attorney, Agent, or Firm* — Daniel A. Blasiole; DeWitt LLP

(57) ABSTRACT

Cells and methods for producing polyhydroxyalkanoates. The cells comprise one or more recombinant genes selected from an R-specific enoyl-CoA hydratase gene, a PHA polymerase gene, a thioesterase gene, and an acyl-CoA-synthetase gene. The cells further have one or more genes functionally deleted. The functionally deleted genes include such genes as an enoyl-CoA hydratase gene, a 3-hydroxyacyl-CoA dehydrogenase, and a 3-ketoacyl-CoA thiolase gene. The recombinant cells are capable of using producing polyhydroxyalkanoates with a high proportion of monomers having the same carbon length from non-lipid substrates, such as carbohydrates.

14 Claims, 6 Drawing Sheets

Specification includes a Sequence Listing.

Related U.S. Application Data

(60) Provisional application No. 61/699,044, filed on Sep. 10, 2012.

(51) Int. Cl.
    *C12N 9/04*         (2006.01)
    *C12N 9/10*         (2006.01)
    *C12N 9/16*         (2006.01)
    *C12N 9/88*         (2006.01)
    *C12N 9/00*         (2006.01)

(52) U.S. Cl.
    CPC ............. *C12N 9/1029* (2013.01); *C12N 9/16* (2013.01); *C12N 9/88* (2013.01); *C12N 9/93* (2013.01); *C12P 7/625* (2013.01); *C12Y 101/01035* (2013.01); *C12Y 402/01017* (2013.01)

(56) References Cited

U.S. PATENT DOCUMENTS

| | | |
|---|---|---|
| 5,480,794 A | 1/1996 | Peoples et al. |
| 5,679,543 A | 10/1997 | Lawlis |
| 6,593,116 B1 | 7/2003 | Huisman et al. |
| 6,759,219 B2 | 7/2004 | Hein et al. |
| 6,913,911 B2 | 7/2005 | Huisman et al. |
| 7,786,355 B2 | 8/2010 | Aguin et al. |
| 7,968,325 B2 | 6/2011 | Hein et al. |
| 2011/0124516 A1* | 5/2011 | Rehm .................. C12N 9/1025 506/9 |
| 2011/0165637 A1 | 7/2011 | Pfleger et al. |
| 2014/0349353 A1 | 11/2014 | Nomura et al. |
| 2018/0201961 A1* | 7/2018 | Pfleger ..................... C12P 7/62 |

OTHER PUBLICATIONS

Nelson et al., "Complete genome sequence and comparative analysis of the metabolically versatile Pseudomonas putida KT2440", Environmental Microbiology, vol. 4, No. 12, pp. 799-808, 2002 (Year: 2002).*
GenBank Accession No. AAN66388.1, published Jan. 31, 2014 (Year: 2014).*
Agnew et al., Implementation of New Routes and Redesign of Native Pathways for Synthesis of Bioplastics in *E. coli*, AIChE Annual Meeting, MN, Oct. 20, 2011.
Amann, E. et al., 1988. Tightly regulated tac promoter vectors useful for the expression of unfused and fused proteins in *Escherichia coli*. Gene. 69, 301-315.
Baba, T. et al., 2006. Construction of *Escherichia coli* K-12 in-frame, single-gene knockout mutants: the Keio collection. Molecular Systems Biology. 2, 11.
Becker, S. et al., 1997. Regulatory O-2 tensions for the synthesis of fermentation products in *Escherichia coli* and relation to aerobic respiration. Archives of Microbiology. 168, 290-296.
Brosius, J. et al., 1985. Spacing of the -10 and -35 regions in the tac promoter: effect on its in vivo activity. Journal of Biological Chemistry. 260, 3539-3541.
Campbell, J. W. et al., 2003. A new *Escherichia coli* metabolic competency: growth on fatty acids by a novel anaerobic beta-oxidation pathway. Molecular Microbiology. 47, 793-805.
Chen et al., Functional Polyhydroxy Alkanoates Synthesized by Microorganisms, Chinese Journal of Polymer Science vol. 18. No. 5 (2000) 389-396.
Chen, G. Q. et al., 2005. The application of polyhydroxyalkanoates as tissue engineering materials. Biomaterials. 26, 6565-6578.
Cherepanov, P. P. et al., 1995. Gene disruption in *Escherichia coli*: TcR and KmR cassettes with the option of Flp-catalyzed excision of the antibiotic-resistance determinant. Gene. 158, 9-14.
Chung, A. et al., 2009. Microbial production of 3-hydroxydodecanoic acid by pha operon and fadBA knockout mutant of Pseudomonas putida KT2442 harboring tesB gene. Applied Microbiology and Biotechnology. 83, 513-519.
Datsenko, K. A. et al., 2000. One-step inactivation of chromosomal genes in *Escherichia coli* K-12 using PCR products. Proceedings of the National Academy of Sciences of the United States of America. 97, 6640-6645.
De Lay, N. R. et al., 2007. In vivo functional analyses of the type II Acyl carrier proteins of fatty acid biosynthesis. Journal of Biological Chemistry. 282, 20319-20328.
Dirusso, C. C., 1990. Primary sequence of the *Escherichia-coli* fadBA operon, encoding the fatty acid-oxidizing multienzyme complex, indicates a high degree of homology to eukaryotic enzymes. Journal of Bacteriology. 172, 6459-6468.
Dirusso, C. C. et al., 2004. Bacterial long chain fatty acid transport: Gateway to a fatty acid-responsive signaling system. Journal of Biological Chemistry. 279, 49563-49566.
Guzman, L. M. et al., 1995. Tight Regulation, Modulation, and High-Level Expression by Vectors Containing the Arabinose PBAD Promoter. Journal of Bacteriology. 177, 4121-4130.
Hoover, S. W. et al., 2011. Bacterial production of free fatty acids from freshwater macroalgal cellulose. Applied Microbiology and Biotechnology. 91, 435-446.
Jiang, X. et al., 2006. Acetone extraction of mcl-PHA from Pseudomonas putida KT2440. Journal of Microbiological Methods. 67, 212-219.
Kato, M. et al., 1996. Production of a novel copolyester of 3-hydroxybutyric acid and medium chain length 3-hydroxyalkanaic acids by *Pseudomonas* sp 61-3 from sugars. Applied Microbiology and Biotechnology. 45, 363-370.
Khanna, S., Srivastava, A. K., 2005. Recent advances in microbial polyhydroxyalkanoates. Process Biochemistry. 40, 607-619.
Klinke et al., Production of Medium-Chain-Length Poly(3-Hydroxyalkanoates) from Gluconate by Recombinant *Escherichia coli*, Applied and Environmental Microbiology, Feb. 1999, p. 540-548.
Langenbach, S. et al., 1997. Functional expression of the PHA synthase gene PhaC1 from Pseudomonas aeruginosa in *Escherichia coli* results in poly(3-hydroxyalkanoate) synthesis. Fems Microbiology Letters. 150, 303-309.
Lee, S. K. et al., 2007. Directed evolution of AraC for improved compatibility of arabinose- and lactose-inducible promoters. Applied and Environmental Microbiology. 73, 5711-5715.
Lennen, R. M. et al., 2010. A Process for Microbial Hydrocarbon Synthesis: Overproduction of Fatty Acids in *Escherichia coli* and Catalytic Conversion to Alkanes. Biotechnology and Bioengineering. 106, 193-202.
Li, Z.-J. et al., 2010. Production of poly(3-hydroxybutyrate-co-4-hydroxybutyrate) from unrelated carbon sources by metabolically engineered *Escherichia coli*. Metabolic Engineering. 12, 352-359.
Liu, Q. et al., 2011. Biosynthesis of poly(3-hydroxydecanoate) and 3-hydroxydodecanoate dominating polyhydroxyalkanoates by beta-oxidation pathway inhibited Pseudomonas putida. Metabolic Engineering. 13, 11-17.
Meng, D.-C. et al., 2012. Production and characterization of poly(3-hydroxypropionate-co-4-hydroxybutyrate) with fully controllable structures by recombinant *Escherichia coli* containing an engineered pathway. Metabolic Engineering. 14, 317-324.
Park, S. J. et al., 2004. New fadB homologous enzymes and their use in enhanced biosynthesis of medium-chain-length polyhydroxyalkanoates in fadB mutant *Escherichia coli*. Biotechnology and Bioengineering. 86, 681-686.
Prieto, M. A. et al., 1999. Engineering of stable recombinant bacteria for production of chiral medium-chain-length poly-3-hydroxyalkanoates. Applied and Environmental Microbiology. 65, 3265-3271.
Qi, Q. S. et al., 1997. Synthesis of poly(3-hydroxyalkanoates) in *Escherichia coli* expressing the PHA synthase gene phaC2 from Pseudomonas aeruginosa: comparison of PhaC1 and PhaC2. Fems Microbiology Letters. 157, 155-162.
Qiu, Y. Z. et al., 2005. Production of Poly(3-hydroxybutyrate-co-3-hydroxyhexanoate) from gluconate and glucose by recombinant Aeromonas hydrophila and Pseudomonas putida. Biotechnology Letters. 27, 1381-1386.

(56) References Cited

OTHER PUBLICATIONS

Rehm et al., A new Metabolic Link between Fatty Acid de NovoSenthesis and Polyhydroxyalkanoic Acid Synthesis, J. Biol. Chem. 1998, 273:24044-24051.

Rehm, B. H. A. et al., 2001. Heterologous expression of the acyl-acyl carrier protein thioesterase gene from the plant *Umbellularia californica* mediates polyhydroxyalkanoate biosynthesis in recombinant *Escherichia coli*. Applied Microbiology and Biotechnology. 55, 205-209.

Ren, Q. et al., 2000. Properties of engineered poly-3-hydroxyalkanoates produced in recombinant *Escherichia coli* strains. Applied and Environmental Microbiology. 66, 1311-1320.

Snell, K. D. et al., 2002. YfcX enables medium-chain-length poly(3-hydroxyalkanoate) formation from fatty acids in recombinant *Escherichia coli* fadB strains. Journal of Bacteriology. 184, 5696-5705.

Steinbuchel, A. et al., 1995. Diversity of Bacterial Polyhydroxyalkanoic Acids. Fems Microbiology Letters. 128, 219-228.

Tappel, R. C. et al., 2012. Precise control of repeating unit composition in biodegradable poly(3-hydroxyalkanoate) polymers synthesized by *Escherichia coli*. Journal of bioscience and bioengineering. 113, 480-6.

Theodorou, E. C. et al., 2012. Involvement of the AtoSCDAEB regulon in the high molecular weight poly-(R)-3-hydroxybutyrate biosynthesis in phaCAB+ *Escherichia coli*. Metabolic Engineering. 14, 354-365.

Thomas on, L. C. et al., 2007. *E. coli* genome manipulation by P1 transduction. Current protocols in molecular biology / edited by Frederick M. Ausubel . . . [et al.]. Chapter 1, Unit 1.17.

Tseng, C. P. et al., 1996. Effect of microaerophilic cell growth conditions on expression of the aerobic (cyoABCDE and cydAB) and anaerobic (narGHJI, frdABCD, and dmsABC) respiratory pathway genes in *Escherichia coli*. Journal of Bacteriology. 178, 1094-1098.

Tsuge, T. et al., 2003. Molecular characterization and properties of (R)-specific enoyl-CoA hydratases from Pseudomonas aeruginosa: metabolic tools for synthesis of polyhydroxyalkanoates via fatty acid beta-oxidation. International Journal of Biological Macromolecules. 31, 195-205.

Voelker, T. A. et al., 1994. Alteration of the specificity and regulation of fatty-acid synthesis of *Escherichia-coli* by expression of a plant medium-chain acyl-acyl carrier protein thioesterase. Journal of Bacteriology. 176, 7320-7327

Wang, H. H. et al., 2011. Biosynthesis of polyhydroxyalkanoate homopolymers by Pseudomonas putida. Applied Microbiology and Biotechnology. 89, 1497-1507.

Wang, Q. et al., 2012. Development of a New Strategy for Production of Medium-Chain-Length Polyhydroxyalkanoates by Recombinant *Escherichia coli* via Inexpensive Non-Fatty Acid Feedstocks. Applied and Environmental Microbiology. 78, 519-527.

Youngquist, J. T. et al., 2012. Kinetic modeling of free fatty acid production in *Escherichia coli* based on continuous cultivation of a plasmid free strain. Biotechnology and Bioengineering. 109, 1518-1527.

Yu, D. G. et al., 2000. An efficient recombination system for chromosome engineering in *Escherichia coli* . Proceedings of the National Academy of Sciences of the United States of America. 97, 5978-5983.

Zhang, Bo, et al., Engineering the Monomer Composition of Polyhydroxyalkanoats Synthesized in *Saccharomyces cerevisiae*, Appl. Environ, Microbiol, 2006, 72(1):536.

Zhou, Q. et al., 2011. Production of 3-hydroxypropionate homopolymer and poly(3-hydroxypropionate-co-4-hydroxybutyrate) copolymer by recombinant *Escherichia coli*. Metabolic Engineering. 13, 777-785.

\* cited by examiner

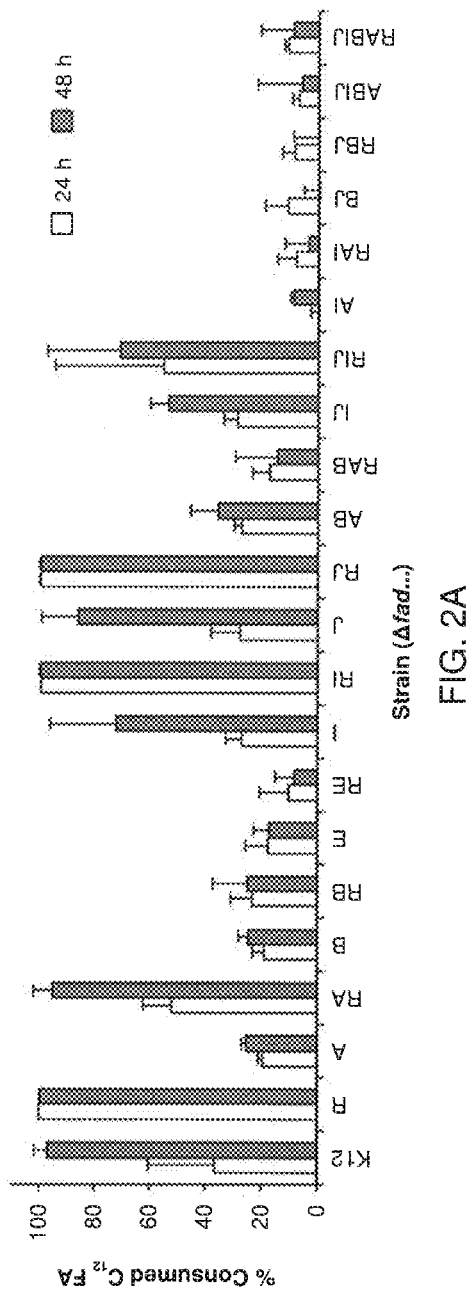
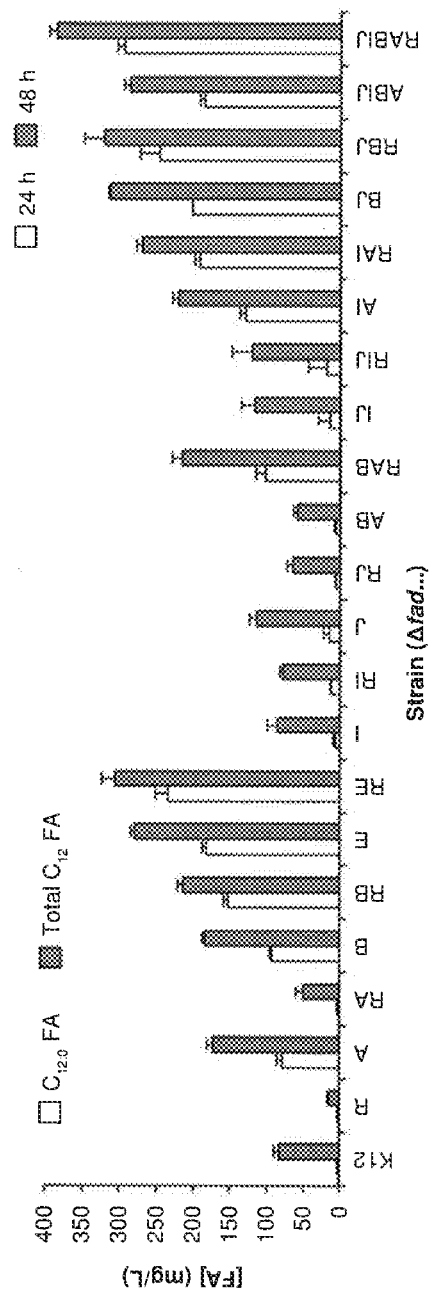
FIG. 2A
FIG. 2B

PRODUCTION OF POLYHYDROXY ALKANOATES WITH A DEFINED COMPOSITION FROM AN UNRELATED CARBON SOURCE

CROSS-REFERENCE TO RELATED APPLICATIONS

This application claims priority under 35 USC § 119(e) to U.S. Provisional Patent Application 61/699,044 filed Sep. 10, 2012, the entirety of which is incorporated herein by reference.

STATEMENT REGARDING FEDERALLY SPONSORED RESEARCH

This invention was made with government support under DE-FC02-07ER64494 awarded by the US Department of Energy. The government has certain rights in the invention.

FIELD OF THE INVENTION

The present invention is directed to cells and methods for producing polyhydroxyalkanoates having a defined monomeric composition at a high yield from an unrelated carbon source.

BACKGROUND

Polyhydroxyalkanoates (PHA) are a class of microbially synthesized polyesters that are produced in large quantities as a form of carbon and energy storage. Natural PHA possesses structural properties that make it attractive as a renewable plastic for select applications. However, most naturally produced PHA contains random monomeric sequences, as the organism adds whatever monomers are present in large enough quantities to the PHA polymer. Such PHA polymers with random monomeric sequences are often not desirable for specific commercial applications. By changing the identity and/or percentage of co-monomers, the structural properties of PHA can be engineered with varying degrees of crystallinity and elasticity (Khanna and Srivastava, 2005).

A wide range of hydroxy-acids have been incorporated as monomers into PHA chains when fed to PHA accumulating organisms (Meng et al., 2012; Steinbuchel and Valentin, 1995; Zhou et al., 2011). However, this strategy requires an external source of each monomer or monomer precursor (e.g., fatty acids), and low-cost sources of such monomers or monomer precursors are not currently available. For this reason, current PHA research is focused on engineering metabolic pathways to produce monomers from unrelated carbon sources such as glucose (Li et al., 2010; Theodorou et al., 2012).

Medium-chain-length PHA (mcl-PHA), which consists of fatty acids containing six or more carbons, is an attractive polymer, desired for novel applications in medical devices, cosmetics, and tissue engineering (Chen and Wu, 2005). Bacteria that naturally produce mcl-PHA incorporate monomers derived from either fatty acid biosynthesis or degradation (β-oxidation) pathways. Efforts to enhance production of mcl-PHA have used metabolic engineering to enhance these pathways. See, e.g., U.S. Pat. No. 5,480,794 to Peoples et al., U.S. Pat. No. 6,593,116 to Huisman et al., U.S. Pat. No. 6,759,219 to Hein et al., U.S. Pat. No. 6,913,911 to Huisman et al., U.S. Pat. No. 7,786,355 Aguin et al., U.S. Pat. No. 7,968,325 to Hein et al., and other references cited herein. However, production of mcl-PHA at high yields from an unrelated carbon source has not been achieved.

Methods and tools for making PHA having a specific monomeric composition, such as mcl-PHA, at a high yield using abundant, inexpensive, and renewable precursors, such as glucose, are needed.

SUMMARY OF THE INVENTION

A specific version of the present invention uses an engineered metabolic pathway for converting glucose into medium-chain-length (mcl)-PHA composed primarily of 3-hydroxydodecanoate monomers. This pathway combines fatty acid biosynthesis, an acyl-ACP thioesterase to generate desired $C_{12}$ and $C_{14}$ fatty acids, β-oxidation for conversion of fatty acids to (R)-3-hydroxyacyl-CoAs, and a PHA polymerase. Expressing an acyl-CoA synthetase, deleting enzymes involved in n-oxidation under aerobic conditions (e.g., fadR, fadA, fadB, fadI, and/or fadJ), and overexpressing an acyl-ACP thioesterase (BTE), an enoyl-CoA hydratase (phaJ3), and mcl-PHA polymerase (phaC2) in a microorganism such as E. coli enables production polyhydroxydodecanoate from glucose under aerobic conditions at yields over 15% cell dry weight (CDW). This is the highest reported production of mcl-PHA of a defined composition from an unrelated carbon source.

The invention provides recombinant cells and methods for producing polyhydroxyalkanoates.

A version of a recombinant cell of the present invention comprises one or more recombinant genes selected from the group consisting of an R-specific enoyl-CoA hydratase gene, a PHA polymerase gene, a thioesterase gene, and an acyl-CoA-synthetase gene, wherein a gene product from a gene selected from the group consisting of an enoyl-CoA hydratase gene, a 3-hydroxyacyl-CoA dehydrogenase, and a 3-ketoacyl-CoA thiolase gene is functionally deleted, and wherein the recombinant cell is capable of producing polyhydroxyalkanoate.

The recombinant cell may be a microbial cell, such as a bacterial cell.

In some versions, the enoyl-CoA hydratase gene is selected from the group consisting of fadB and fadJ.

In some versions, the 3-hydroxyacyl-CoA dehydrogenase gene is selected from the group consisting of fadB and fadJ.

In some versions, the 3-ketoacyl-CoA thiolase gene is selected from the group consisting of fadA and fadI.

In some versions, the gene products of fadA and fadI; fadB and fadJ; or fadA, fadI, fadB and fadJ are functionally deleted.

In some versions, the gene product of fadR is functionally deleted.

In some versions, gene products of fadA and fadI; fad R, fadA, and fadI; fadB and fadJ; fad R, fadB, and fadJ; fadA, fadB, fad, and fadJ; or fad R, fadA, fadB, fadI, and fadJ are functionally deleted.

In some versions, the enoyl-CoA hydratase gene is a phaJ gene.

In some versions, the PHA polymerase gene is a phaC gene.

In some versions, the enoyl-CoA hydratase gene is phaJ3 and the PHA polymerase gene is phaC2.

In some versions, the thioesterase gene is *Umbellularia californica* thioesterase or a homolog thereof.

In some versions, the acyl-CoA-synthetase gene is PP_0.0763 from *P. putida*.

In some versions, the cell further comprises a recombinant phasin gene.

In some versions, the recombinant cell comprises each of a recombinant R-specific enoyl-CoA hydratase gene, a recombinant PHA polymerase gene, a recombinant thioesterase gene, and a recombinant acyl-CoA-synthetase gene, wherein the recombinant cell is capable of producing polyhydroxyalkanoate from carbohydrate in a medium devoid of a fatty acid source.

A version of a method of the present invention comprises culturing a recombinant cell as described herein.

Some versions comprise culturing the recombinant cell in aerobic conditions.

Some versions comprise culturing the recombinant cell in a medium comprising a carbohydrate and substantially devoid of a fatty acid source.

In some versions, the culturing produces polyhydroxyalkanoate to at least about 7.5% cell dry weight.

In some versions, the culturing produces polyhydroxyalkanoate comprised of hydroxyalkanoate monomers, wherein greater than about 50% of the hydroxyalkanoate monomers comprise hydrocarbon chains comprising same number of carbons.

The objects and advantages of the invention will appear more fully from the following detailed description of the preferred embodiment of the invention made in conjunction with the accompanying drawings.

BRIEF DESCRIPTION OF THE DRAWINGS

FIG. 2A shows the metabolism of exogenously fed dodecanoic acid after 24 and 48 h of shake flask cultivation as a percent of the initial fatty acid concentration by a library of *E. coli* β-oxidation knock-out strains harboring the specific fad deletion(s) indicated on the horizontal axis (e.g., K12=*E. coli* K-12 MG1655; R=*E. coli* K-12 MG1655 ΔfadR; etc.). Data for both saturated ($C_{12:0}$) and total $C_{12}$ (including unsaturated and hydroxy) species are presented.

FIG. 2B shows the metabolism of endogenously synthesized fatty acids in strains with plasmid-based expression of BTE after 48 h of cultivation by a library of *E. coli* β-oxidation knock-out strains harboring the specific fad deletion(s) indicated on the horizontal axis (e.g., K12=*E. coli* K-12 MG1655; R=*E. coli* K-12 MG1655 ΔfadR; etc.). Data for both saturated ($C_{12:0}$) and total $C_{12}$ (including unsaturated and hydroxy) species are presented.

DETAILED DESCRIPTION OF THE INVENTION

Figure 1:
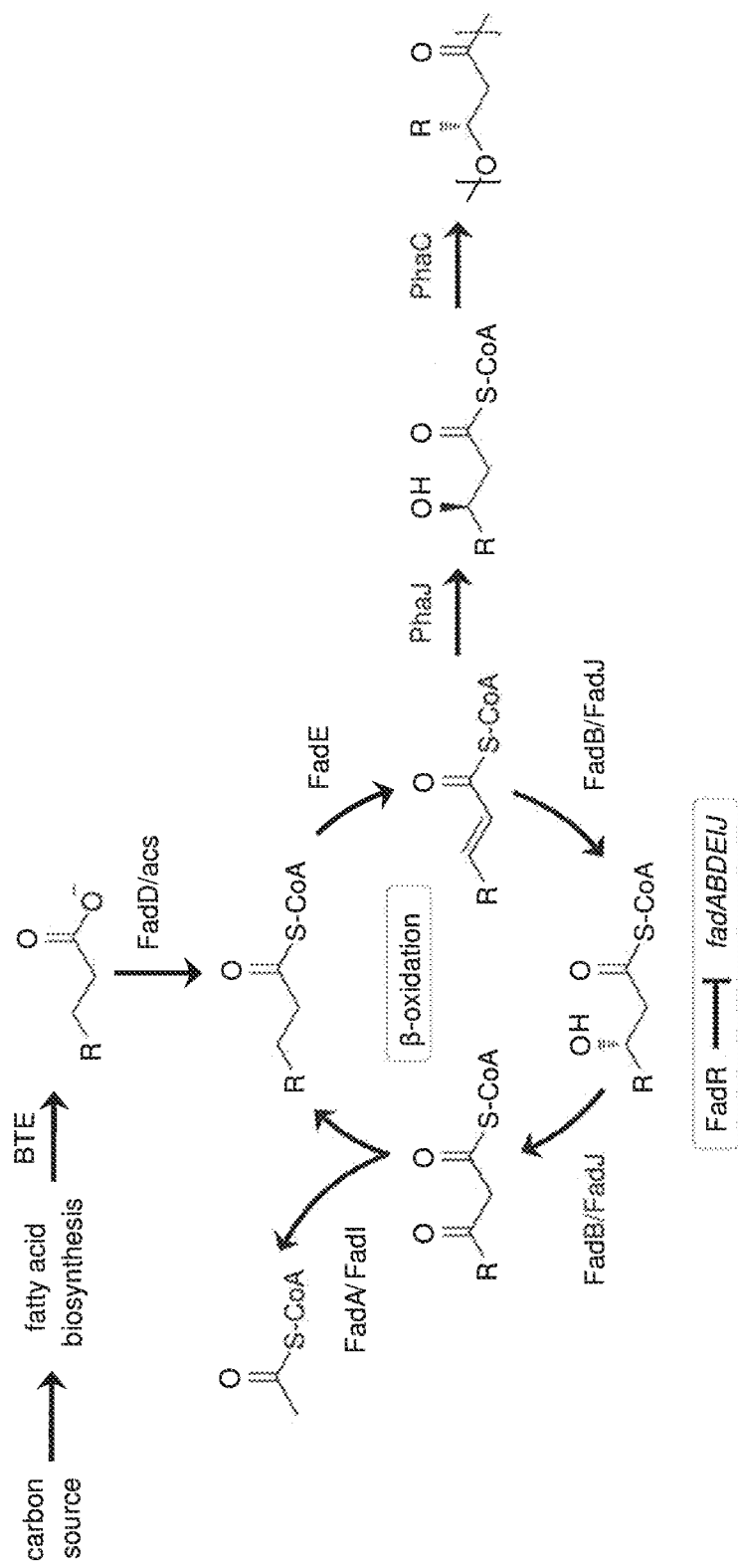
FIG. 1 depicts a schematic of a metabolic pathway for mcl-PHA biosynthesis in *E. coli*. A carbon source (i.e., glucose) is catabolized to acetyl-CoA which enters fatty acid biosynthesis for production of fatty acyl-ACPs. $C_{12}$ and $C_{14}$ acyl-ACPs are substrates for the thioesterase. BTE, which catalyzes FFA formation. An acyl-CoA synthetase (e.g., FadD) activates the FFAs for degradation via a partially intact β-oxidation cycle generating enoyl-CoAs which PhaJ hydrates to produce mcl-PHA monomers for polymerization by PhaC. The resulting monomer composition is therefore identical to that of the FFA pool generated by the thioesterase. FadR represses expression of β-oxidation genes in the absence of acyl-CoAs.

The following abbreviations are used herein:
(mcl)-PHA—(medium-chain-length)-polyhydroxyalkanoate;
Acyl-carrier protein—ACP;
BTE—California Bay Laurel (*Umbellularia californica*) Thioesterase;
CDW—Cell Dry Weight;
CoA—Coenzyme A;
$DO_2$—Dissolved oxygen;
EC—Enzyme Commission
ECGSC—*Escherichia coli* Genetic Stock Center—Yale University;
FAME—Fatty Acid Methyl Ester;
GC/MS—Gas Chromatography Mass Spectrometry;
LB—Lysogeny Broth;
PBS—Phosphate Buffered Saline; and
PCR—Polymerase Chain Reaction.

The present invention is directed to cells and methods for producing polyhydroxyalkanoates having a defined monomeric composition at a high yield from an unrelated carbon source. The invention involves genetically modifying cells to feed carbon substrates having a defined carbon length into the early steps of the β-oxidation pathway and then diverting the substrates toward polyhydroxyalkanoate synthesis by shutting down or reducing the efficiency of downstream steps in the β-oxidation pathway.

One aspect of the invention is a recombinant (i.e., genetically modified) cell that is capable of producing polyhydroxyalkanoate. The cell of the present invention may be any type of cell that is capable of producing polyhydroxyalkanoate, either naturally or by virtue of genetic engineering. Examples of suitable cells include but are not limited to bacterial cells, yeast cells, fungal cells, insect cells, mammalian cells, and plant cells. Examples of suitable bacterial cells include gram-positive bacteria such as strains of *Bacillus*, (e.g., *B. brevis* or *B. subtilis*), *Pseudomonas*, or *Streptomyces*, or gram-negative bacteria, such as strains of *E. coli* or *Aeromonas hydrophila*. Particularly desirable cells for expression in this regard include bacteria that do not produce lipopolysaccharide and are endotoxin free. Examples of suitable yeast cells include strains of *Saccharomyces*, such as *S. cerevisiae*; *Schizosaccharomyces*; *Kluyveromyces*; *Pichia*, such as *P. pastoris* or *P. methlanolica*; *Hansenula*, such as *H. Polymorpha*; *Yarrowia*; or *Candida*. Examples of suitable filamentous fungal cells include strains of *Aspergillus*, e.g., *A. oryzae*, *A. niger*, or *A. nidulans*; *Fusarium* or *Trichoderma*. Examples of suitable insect cells include a *Lepidoptora* cell line, such as *Spodoptera frugiperda* (Sf9 or Sf21) or *Trichoplusioa ni* cells ("HIGH FIVE"-brand insect cells, Invitrogen, Carlsbad, Calif.) (U.S. Pat. No. 5,077,214). Examples of suitable mammalian cells include Chinese hamster ovary (CHO) cell lines, e.g., CHO-K1 (ATCC CCL-61); green monkey cell lines, e.g., COS-1 (ATCC CRL-1650) and COS-7 (ATCC CRL-1651); mouse cells, e.g., NS/O; baby hamster kidney (BHK) cell lines, e.g., ATCC CRL-1632 or ATCC CCL-10; and human cells, e.g., HEK 293 (ATCC CRL-1573). Examples of suitable plant cells include those of oilseed crops, including rapeseed, canola, sunflower, soybean, cottonseed, and safflower plants, and cells from other plants such as *Arabidopsis thaliana*. Some of the foregoing cell types are capable of naturally producing polyhydroxyalkanoate, such as certain microorganisms. The other cell types are capable of producing polyhydroxyalkanoate by being genetically modified to express a PHA synthase or other enzymes. See, e.g., U.S. Pat. No. 5,480,794 to Peoples et al. and Zhang et al. *Applied and Environmental Microbiology*, 2006, 72(1):536-543, which are incorporated by reference in their entirety. Preferred cells are microorganisms, such as *E. coli*.

The recombinant cell of the invention preferably has one or more genes in the β-oxidation pathway functionally deleted to inhibit consumption of substrates for polyhydroxyalkanoate production. "Functional deletion" or its grammatical equivalents refers to any modification to a microorganism that ablates, reduces, inhibits, or otherwise disrupts production of a gene product, renders the gene product non-functional, or otherwise reduces or ablates the gene product's activity. "Gene product" refers to a protein or polypeptide encoded and produced by a particular gene. In some versions of the invention, functionally deleting a gene product or homolog thereof means that the gene is mutated to an extent that corresponding gene product is not produced at all.

One of ordinary skill in the art will appreciate that there are many well-known ways to functionally delete a gene product. For example, functional deletion can be accomplished by introducing one or more genetic modifications. As used herein, "genetic modifications" refer to any differences in the nucleic acid composition of a cell, whether in the cell's native chromosome or in endogenous or exogenous non-chromosomal plasmids harbored within the cell. Examples of genetic modifications that may result in a functionally deleted gene product include but are not limited to mutations, partial or complete deletions, insertions, or other variations to a coding sequence or a sequence controlling the transcription or translation of a coding sequence; placing a coding sequence under the control of a less active promoter; and expressing ribozymes or antisense sequences that target the mRNA of the gene of interest, etc. In some versions, a gene or coding sequence can be replaced with a selection marker or screenable marker. Various methods for introducing the genetic modifications described above are well known in the art and include homologous recombination, among other mechanisms. See, e.g., Green et al., *Molecular Cloning: A laboratory manual*, 4$^{th}$ ed., Cold Spring Harbor Laboratory Press (2012) and Sambrook et al., *Molecular Cloning: A Laboratory Manual*, 3$^{rd}$ ed., Cold Spring Harbor Laboratory Press (2001). Various other genetic modifications that functionally delete a gene product are described in the examples below. Functional deletion can also be accomplished by inhibiting the activity of the gene product, for example, by chemically inhibiting a gene product with a small-molecule inhibitor, by expressing a protein that interferes with the activity of the gene product, or by other means.

In certain versions of the invention, the functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the non-functionally deleted gene product.

In certain versions of the invention, a cell with a functionally deleted gene product may have less than about 95%, less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the activity of the gene product compared to a cell with the non-functionally deleted gene product.

In certain versions of the invention, the functionally deleted gene product may be expressed at an amount less than about 95%, less than about 90%, less than about 85% less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 10%, less than about 5%, less than about 1%, or about 0% of the amount of the non-functionally deleted gene product.

In certain versions of the invention, the functionally deleted gene product may result from a genetic modification in which at least 1, at least 2, at least 3, at least 4, at least 5, at least 10, at least 20, at least 30, at least 40, at least 50, or more nonsynonymous substitutions are present in the gene or coding sequence of the gene product.

In certain versions of the invention, the functionally deleted gene product may result from a genetic modification in which at least 1, at least 2, at least 3, at least 4, at least 5, at least 10, at least 20, at least 30, at least 40, at least 50, or more bases are inserted in the gene or coding sequence of the gene product.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of the gene product's gene or coding sequence is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a promoter driving expression of the gene product is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of an enhancer controlling transcription of the gene product's gene is deleted or mutated.

In certain versions of the invention, the functionally deleted gene product may result from a genetic modification in which at least about 1%, at least about 5%, at least about 10%, at least about 15%, at least about 20%, at least about 25%, at least about 30%, at least about 35%, at least about 40%, at least about 50%, at least about 55%, at least about 60%, at least about 65%, at least about 70%, at least about 75%, at least about 80%, at least about 85%, at least about 90%, at least about 95%, or about 100% of a sequence controlling translation of gene product's mRNA is deleted or mutated.

In certain versions of the invention, the decreased activity or expression of the functionally deleted gene product is determined with respect to the activity or expression of the gene product in its unaltered state as found in nature. In certain versions of the invention, the decreased activity or expression of the functionally deleted gene product is determined with respect to the activity or expression of the gene product in its form in a corresponding cell. In certain versions, the genetic modifications giving rise to a functionally deleted gene product are determined with respect to the gene in its unaltered state as found in nature. In certain versions, the genetic modifications giving rise to a functionally deleted gene product are determined with respect to the gene in its form in a corresponding cell. As used herein, "corresponding cell" refers to a cell of the same species having the same or substantially same genetic and proteomic composition as a cell of the invention, with the exception of genetic and proteomic differences resulting from the manipulations described herein for the cells of the invention.

In some versions of the invention, a gene product of an enoyl-CoA hydratase gene in the recombinant cell is functionally deleted. Enoyl-CoA hydratases include enzymes classified under Enzyme Commission (EC) number 4.2.1.17. Enoyl-CoA hydratases catalyze the conversion of trans-2-(or 3)-enoyl-CoA to (3S)-3-hydroxyacyl-CoA in the β-oxidation pathway. The term "enoyl-CoA hydratase" used herein without an indication of stereospecificity refers to the enzymes under EC 4.2.1.17 that produce (3S)-3-hydroxyacyl-CoA. These enzymes are distinct from the enzymes that produce (3R)-3-hydroxyacyl-CoA and are designated under EC 4.2.1.119, which are referred to herein as "R-specific enoyl-CoA hydratases." See below. Examples of enoyl-CoA hydratase genes in bacteria include fadB (SEQ ID NO:1 (coding sequence) and SEQ ID NO:2 (protein); GenBank NC_000913.2 at 4026805-4028994 (complement)) and fadJ (SEQ ID NO:3 (coding sequence) and SEQ ID NO:3 (protein); GenBank NC_000913.2 at 2455037-2457181 (complement)). Examples of enoyl-CoA hydratase genes in yeast include FOX2 (GenBank NC_001143 at 454352-457054 (complement)) or the enzyme encoded by Kyoto Encyclopedia of Genes and Genomes (KEGG) (http://www.genome.jp/kegg/) entry number NCU06488. An example of enoyl-CoA hydratase genes in filamentous fungal cells includes the enzyme encoded by KEGG entry number AN5916.2. An example of an enoyl-CoA hydratase gene in insect cells is Mfe2 (GenBank NM_132881.2). Examples of enoyl-CoA hydratase genes in mammalian cells include ECHS1 (GenBank NM_004092.3), EHHADH (GenBank NM_001966.3), and HADHA (GenBank NM_000182.4). Examples of enoyl-CoA hydratase genes in plants include MFP2 (GenBank NM_111566.3) and AIM1 (GenBank NM_119045.4). Homologs of the above-mentioned enoyl-CoA hydratase genes suitable for use in the present invention can be determined by many known methods, one of which is described below. In preferred versions of the invention, the enoyl-CoA hydratase gene product that is functionally deleted has a sequence comprising SEQ ID NO:2 or a sequence homologous thereto, SEQ ID NO:4 or a sequence homologous thereto, or SEQ ID NO:2 and SEQ ID NO:4 or sequences homologous thereto.

In some versions of the invention, a gene product of a 3-hydroxyacyl-CoA dehydrogenase gene in the recombinant cell is functionally deleted. 3-Hydroxyacyl-CoA dehydrogenases include enzymes classified under EC number 1.1.1.35. 3-Hydroxyacyl-CoA dehydrogenases catalyze the conversion of (3S)-3-hydroxyacyl-CoA to 3-ketoacyl CoA in the β-oxidation pathway. Examples of 3-hydroxyacyl-CoA dehydrogenase genes in bacteria include fadB (SEQ ID NO:1 (coding sequence) and SEQ ID NO:2 (protein); GenBank NC_000913.2 at 4026805-4028994 (complement)) and fadJ (SEQ ID NO:3 (coding sequence) and SEQ ID NO:4 (protein); GenBank NC_000913.2 at 2455037-2457181 (complement)). An example of a 3-hydroxyacyl-CoA dehydrogenase gene in yeast includes FOX2 (GenBank NC_001143 at 454352-457054 (complement)). An example of a 3-hydroxyacyl-CoA dehydrogenase gene in filamentous fungal cells includes the enzyme encoded by KEGG entry number AN7238.2. An example of a 3-hydroxyacyl-CoA dehydrogenase gene in insect cells is Mfe2 (GenBank NM_0.132881.2). Examples of 3-hydroxyacyl-CoA dehydrogenase genes in mammalian cells include EHHADH (GenBank NM_001966.3), HSD17B10 (GenBank NG_008153.1), HADH (GenBank NM_001184705.2), and HSD17B4 (GenBank NG_008182.1). Examples of 3-hydroxyacyl-CoA dehydrogenase genes in plants include MFP2 (GenBank NM_111566.3) and AIM1 (GenBank NM_119045.4). Homologs of the above-mentioned 3-hydroxyacyl-CoA dehydrogenase genes suitable for use in the present invention can be determined by many known methods, one of which is described below. In preferred versions of the invention, the 3-hydroxyacyl-CoA dehydrogenase gene product that is functionally deleted has a sequence comprising SEQ ID NO:2 or a sequence homologous thereto. SEQ ID NO:4 or a sequence homologous thereto, or SEQ ID NO:2 and SEQ ID NO:4 or sequences homologous thereto.

In some versions of the invention, a gene product of a 3-ketoacyl-CoA thiolase gene in the recombinant cell is functionally deleted. 3-Ketoacyl-CoA thiolases include enzymes classified under EC number 2.3.1.16. 3-Ketoacyl-CoA thiolases catalyze the conversion of 3-ketoacyl CoA to acetyl-CoA and a shortened acyl-CoA species in the β-oxidation pathway. Examples of 3-ketoacyl-CoA thiolase genes in bacteria include fadA (SEQ ID NO:5 (coding sequence) and SEQ ID NO:6 (protein); GenBank NC_000913.2 at 4025632-4026795 (complement)) and fadI (SEQ ID NO:7 (coding sequence) and SEQ ID NO:8 (protein); GenBank NC_000913.2 at 2457181-2458491 (complement)). An example of a 3-ketoacyl-CoA thiolase gene in yeast includes FOX3 (GenBank NM_001179508.1). Examples of 3-ketoacyl-CoA thiolase genes in filamentous fungal cells include the enzymes encoded by KEGG entry numbers AN5646.2 and AN5698.2. An example of a 3-ketoacyl-CoA thiolase gene in insect cells is gene yip2 (GenBank NM_078804.3). Examples of 3-ketoacyl-CoA thiolase genes in mammalian cells include ACAA1 (GenBank NR_024024.1), ACAA2 (GenBank NM_006111.2), and HADHB (GenBank NG_007294.1). Examples of 3-ketoacyl-CoA thiolase genes in plants include PKT4 (GenBank NM_100351.4), PKT3 (GenBank NM_128874.3), and PKT2 (GenBank NM_180826.3). Homologs of the above-mentioned 3-ketoacyl-CoA thiolase genes suitable for use in the present invention can be determined by many known methods, one of which is described below. In preferred versions of the invention, 3-ketoacyl-CoA thiolase gene product that is functionally deleted has a sequence comprising SEQ ID NO:6 or a sequence homologous thereto, SEQ ID NO:8 or a sequence homologous thereto, or SEQ ID NO:6 and SEQ ID NO:8 or sequences homologous thereto.

Production of polyhydroxyalkanoates can be enhanced when the β-oxidation pathway is maximally shut down at a particular step. When a cell has more than one enzyme catalyzing a step in the β-oxidation pathway, i.e., enoyl-CoA hydration, (3S)-hydroxyacyl-CoA dehydrogenation, or ketoacyl-CoA thiolation, it is preferred that more than one enzyme catalyzing that step is functionally deleted. It is more preferred that all enzymes catalyzing that step are functionally deleted. In the case of bacteria, for example, it is preferred that products of both fadA and fadI, both fadB and fadJ, or all of fadA, fadB, fadI, and fadJ are functionally deleted.

In some versions of the invention, one or more factors that regulate expression of β-oxidation genes in the cells are functionally deleted. It is thought that such a modification to the cells helps to enhance entry of carbon substrates into the β-oxidation pathway for synthesis of polyhydroxyalkanoates. In preferred bacterial cells such as *Escherichia coli*, this is accomplished by functionally deleting the product of fadR (SEQ ID NO:9 (coding sequence) and SEQ ID NO:10 (protein); GenBank NC_000913.2 at 1234161-1234880). FadR encodes a transcription factor (fadR) that cxoordinately regulates the machinery required for β-oxidation and the expression of a key enzyme in fatty acid biosynthesis. FadR works as a repressor that controls transcription of the whole fad regulon, including fadA, fadB, fadD, fadE, fadI, and fadJ. Binding of fadR is inhibited by fatty acyl-CoA compounds, which de-represses expression of the genes in the fad regulon. Functional deletion of fadR thereby upregulates such genes as fadD and fadE to enhance entry of carbon substrates through the initial steps of the β-oxidation pathway (see FIG. 1). Regulatory proteins that control expression of β-oxidation genes in cells of other organisms are known in the art. The genes encoding these proteins can be similarly functionally deleted to enhance entry of carbon substrates through the initial steps of the β-oxidation pathway for synthesis of polyhydroxyalkanoates. In preferred versions of the invention, the regulatory protein that is functionally deleted has a sequence comprising SEQ ID NO:10 or a sequence homologous thereto.

In a preferred bacterial cell of the invention, the cell comprises a functional deletion of fadR gene product in addition to functional deletion of products of fadA, fadI, fadB, fadJ, fadA and fadI, fadB and fadJ, or fadA, fadB, fadI, and fadJ so that flux through the initial steps β-oxidation pathway is enhanced but flux through the downstream steps (i.e., enoyl-CoA hydration, (3S)-hydroxyacyl-CoA dehydrogenation, and/or ketoacyl-CoA thiolation) is not.

In various versions of the invention, the cell is genetically modified to comprise a recombinant gene. In most cases, the recombinant gene is configured to be expressed or overexpressed in the cell. If a cell endogenously comprises a particular gene, the gene may be modified to exchange or optimize promoters, exchange or optimize enhancers, or exchange or optimize any other genetic element to result in increased expression of the gene. Alternatively, one or more additional copies of the gene or coding sequence thereof may be introduced to the cell for enhanced expression of the gene product. If a cell does not endogenously comprise a particular gene, the gene or coding sequence thereof may be introduced to the cell for expression of the gene product. The gene or coding sequence may be incorporated into the genome of the cell or may be contained on an extrachromosomal plasmid. The gene or coding sequence may be introduced to the cell individually or may be included on an operon. Techniques for genetic manipulation are described in further detail below.

In some versions of the invention, the cells are genetically modified to express or overexpress a recombinant acyl-CoA synthetase gene. This is thought to constitute a mechanism of modifying cells to enhance entry of carbon substrates into the β-oxidation pathway. Suitable acyl-CoA synthetases include enzymes classified under the EC 6.2.1.-, such as EC 6.2.1.3. Acyl-CoA synthetases catalyze the conversion of free fatty acids, coenzyme A, and ATP to fatty acyl CoAs plus AMP (Black et al. 1992, *J. Biol. Chem.* 267:25513-25520). Examples of suitable genes for acyl CoA synthetases include fadD (SEQ ID NO:11 (coding sequence) and SEQ ID NO:12 (protein); GenBank NC_000913.2 at 1886085-1887770 (complement)) from *E. coli* (Black et al. 1992, *J. Biol. Chem.* 267:25513-25520), alkK from *Pseudomonas oleovorans* (GenBank AJ245436.1 at 13182-14822) (van Beilen et al. 1992, *Molecular Microbiology* 6:3121-3136), Pfacs1 from *Plasmodium falciparum* (GenBank AF007828.2) (Matesanz et al. 1999, *J. Mol. Biol.* 291:59-70), and PP_0763 (KEGG) from *P. putida* (SEQ ID NO:13 (coding sequence) and SEQ ID NO:14 (protein)), described herein. Methods and materials for identification of other suitable acyl-CoA synthetases are described in U.S. Pat. No. 7,786,355. Homologs of the above-mentioned acyl-CoA synthetase genes suitable for use in the present invention can be determined by many known methods, one of which is described below. In preferred versions of the invention, the cells express or overexpress an acyl-CoA synthetase gene product that has a sequence comprising SEQ ID NO:12 or a sequence homologous thereto, SEQ ID NO: 14 or a sequence homologous thereto, or SEQ ID NO:12 and SEQ ID NO:14 or sequences homologous thereto.

In some versions of the invention, the cells are genetically modified to express or overexpress a recombinant R-specific enoyl-CoA hydratase gene. R-specific enoyl-CoA hydratase genes include enzymes classified under EC 4.2.1.119. R-specific enoyl-CoA hydratase genes catalyze the conversion of trans-2(or 3)-enoyl-CoA to (3R)-3-hydroxyacyl-CoA. As described above, the term "R-specific enoyl-CoA hydratase," refers only to enzymes which produce (3R)-3-hydroxyacyl-CoA and are distinct from the enzymes referred to herein as "enoyl-CoA hydratase," which produce (3S)-3-hydroxyacyl-CoA and are classified under EC 4.2.1.17. Examples of suitable R-specific enoyl-CoA hydratases include any of the various phaJ genes in such microorganisms as *Aeromonas* spp., including *A. caviae*, *Pseudomonas aeruginosa*, *Ralstonia eutropha*, among others. See the following Examples for methods for amplifying PHA genes phaJ1-4, the sequences of which can be readily obtained using methods known in the art. Homologs of the above-mentioned R-specific enoyl-CoA hydratase genes suitable for the use in the present invention can be determined by many known methods, one of which is described below.

In some versions of the invention, the cells are genetically modified to express or overexpress a recombinant PHA polymerase gene. PHA polymerase genes include enzymes classified under EC 2.3.1.-. PHA polymerase genes catalyze the conversion of (3R)-3-hydroxyacyl-CoA monomers into polyhydroxyalkanoate polymers. Examples of suitable PHA polymerases include any of the various phaC or phbC genes in such microorganisms as *Pseudomonas aeruginosa*, among others. See the following Examples for methods for amplifying PHA genes phaC1-2, the sequences of which can be readily obtained using methods known in the art. See also U.S. Pat. No. 5,250,430 and Tsuge et al. 2003. *International Journal of Biological Macromolecules.* 31:195-205. Homologs of the above-mentioned PHA polymerase genes suitable for the use in the present invention can be determined by many known methods, one of which is described below.

For high production of mcl-PHA containing high yields of $C_{12}$ monomer units, it is preferred that the cell expresses or overexpresses a combination of phaJ3 (SEQ ID NO:15 (coding sequence) and SEQ ID NO:16 (protein)) and phaC2 (SEQ ID NO:17 (coding sequence) and SEQ ID NO: 18 (protein)), as this combination unexpectedly results in a high PHA content with a high $C_{12}$ composition. See, e.g., the examples, particularly at Table 2. Accordingly, cells in preferred versions of the invention express or overexpress gene products having a sequence comprising SEQ ID NO: 16 or a sequence homologous thereto, SEQ ID NO:18 or a sequence homologous thereto, or SEQ ID NO:16 and SEQ ID NO:18 or sequences homologous thereto.

In some versions of the invention, the cells are genetically modified to express or overexpress a recombinant thioesterase gene. Thioesterases include enzymes classified into EC 3.1.2.1 through EC 3.1.2.27 based on their activities on different substrates, with many remaining unclassified (EC 3.1.2.-). Thioesterases hydrolyze thioester bonds between acyl chains and CoA or on acyl chains and ACP. These enzymes terminate fatty acid synthesis by removing the CoA or ACP from the acyl chain.

Expression or overexpression of a recombinant thioesterase gene can be used to engineer to produce a homogeneous population of fatty acid products to feed into the β-oxidation and polyhydroxyalkanoate synthesis pathways, and thereby produce polyhydroxyalkanoates having a defined side chain length. To engineer a cell for the production of a homogeneous population of fatty acid products, one or more thioesterases with a specificity for a particular carbon chain length or chain lengths can be expressed. For example, any of the thioesterases shown in the following table can be expressed individually or in combination to increase production of fatty acid products having specific chain lengths.

| Thioesterases. | | | |
|---|---|---|---|
| Gen Bank Accession Number | Source Organism | Gene | Preferential product produced |
| AAC73596 | *E. coli* | tesA without leader sequence | $C_8$-$C_{18}$ |
| Q41635; V17097; M94159 | *Umbellularia californica* | fatB | $C_{12:0}$ |
| Q39513 | *Cuphea hookeriana* | fatB2 | $C_{8:0}$-$C_{10:0}$ |
| AAC49269 | *Cuphea hookeriana* | fatB3 | $C_{14:0}$-$C_{16:0}$ |
| Q39473 | *Cinnamomum camphorum* | fatB | $C_{14:0}$ |
| CAA85388 | *Arabidopsis thaliana* | fatB[M141T]* | $C_{16:1}$ |
| NP 189147; NP 193041 | *Arabidopsis thaliana* | fatA | $C_{18:1}$ |
| CAC39106 | *Bradyrhizobium japonicum* | fatA | $C_{18:1}$ |
| AAC72883 | *Cuphea hookeriana* | fatA | $C_{18:1}$ |

*Mayer et al., *BMC Plant Biology* 7: 1-11, 2007.

Other thioesterases that can be expressed or overexpressed in the cell include any of the many acyl-acyl carrier protein thioesterases from *Streptococcus pyogenes*, including any having GenBank Accession Numbers AAZ51384.1, AAX71858.1, AAT86926.1, YP_280213.1, YP_060109.1. YP_006932842.1, YP_005411534.1, AFC68003.1, AFC66139.1, YP_006071945.1, YP_600436.1, AEQ24391.1 and ABF37868.1; a palmitoyl-acyl carrier protein thioesterase from *Ricinus communis*, such as those having GenBank Accession Numbers EEF47013.1, XP_002515564.1, EEF51750.1, XP_002511148.1, and EEF36100.1; a myristoyl-acyl carrier protein thioesterase from *Ricinus communis*, such as those having GenBank Accession Numbers EEF44689.1 and XP_002517525.1; an oleoyl-acyl carrier protein thioesterase from *Ricinus communis*, such as those having GenBank Accession Numbers EEF29646.1 and XP_002532744.1; an acyl-acyl carrier protein thioesterase from *Ricinus communis*, such as that having GenBank Accession Number ABV54795.1; an acyl-acyl carrier protein thioesterase from *Jatropha curcus*, such as that described in Zhang, X. et al. (2011) *Metab. Eng.* 13, 713-722; an FabD from *Streptomyces avermitilis*, such as that having GenBank Accession Number NP_826965.1; a FadM acyl-CoA thioesterase from *E. coli*, such as that having GenBank Accession Number NP_414977.1; a TesB thioesterase II (acyl-CoA thioesterase), such as those having GenBank Accession Numbers ZP_12508749.1, EGT66607.1, ZP_030352.15.1, and EDV65664.1; and a fatB-type thioesterase specific for C18:1 and C18:0 derived from *Madhuca latifolia*, such as that having the GenBank Accession Number AY835985. These and additional suitable thioesterases that can be expressed or overexpressed in the cell are described in U.S. 2011/0165637 to Pfleger et al.;

Lu. X. et al. (2008) *Metab. Eng.* 10, 333-339; Liu, T. et al. (2010) *Metab. Eng.* 12, 378-386; Steen, E. J. et al. (2010) *Nature* 463, 559-562; Lennen, R. M. et al. (2010) *Biotechnol. Bioeng.* 106, 193-202; Lennen, R. M. et al. (2011) *Appl. Environ. Microbiol.* 77, 8114-8128; Youngquist, J. T. et al. (2012) *Biotechnol. Bioeng.* 109, 1518-1527; Jeon, E. et al. (2011) *Enzyme Microb. Technol.* 49, 44-51; Li, M. et al. (2012) *Metab. Eng.* 14, 380-387; Zhang, X. et al. (2012) *Biotechnol. Prog.* 28, 60-65; Zhang, X. et al. (2011) *Metab. Eng.* 13, 713-722; Liu, H. et al. (2012) *Microb. Cell Fact.* 11, 41; Yu, X. et al. (2011) *Proc. Natl. Acad. Sci. U.S.A.* 108, 18643-18648; Dellomonaco, C. et al. (2011) *Nature* 476, 355-359; Zhang, F. et al. (2012) *Nat. Biotechnol.* 30, 354-359; and Lennen et al. (2012) *Trends in Biotechnology* 30(12). 659-667. Yet other suitable thioesterases can be found in the ThYme: Thioester-active Enzymes database at http://www.enzyme.ebirc.iastate.edu/. Homologs of the thioesterases described herein suitable for the use in the present invention can be determined by many known methods, one of which is described below.

In some versions, one or more endogenous thioesterases having a specificity for carbon chain lengths other than the desired product's carbon chain length can be functionally deleted. For example, C10 fatty acid products can be produced by attenuating a thioesterase specific for C18 (for example, accession numbers AAC73596 and POADA1), and expressing a thioesterase specific for C10 (for example, accession number Q39513). This results in a relatively homogeneous population of fatty acid products that have a carbon chain length of 10. In another example, C14 fatty acid products can be produced by attenuating endogenous thioesterases that produce non-C14 fatty acids and expressing the thioesterase with accession number Q39473, which uses C14-acyl carrier protein (ACP) as a substrate. In yet another example, C12 fatty acid products can be produced by expressing thioesterases that use C12-ACP as a substrate (for example, accession number Q41635) and attenuating thioesterases that produce non-C12 fatty acids.

In a preferred version of the invention, the cell comprises a gene expressing a codon-optimized thioesterase derived from California Bay Laurel (*Umbellularia californica*) thioesterase (BTE) having the following nucleic acid coding sequence (SEQ ID NO:19) and amino acid sequence (SEQ ID NO:20):

```
cccgggagga ggattataaa atg act cta gag tgg aaa ccg aaa cca aaa ctg     53
                      Met Thr Leu Glu Trp Lys Pro Lys Pro Lys Leu
                       1               5                      10 cct caa ctg ctg gat gat cac ttc ggt ctg cac ggt ctg gtg ttt cgt      101
Pro Gln Leu Leu Asp Asp His Phe Gly Leu His Gly Leu Val Phe Arg
            15                  20                  25 cgt act ttc gca att cgt tct tat gaa gtg ggt cca gat cgt tct acc      149
Arg Thr Phe Ala Ile Arg Ser Tyr Glu Val Gly Pro Asp Arg Ser Thr
        30                  35                  40 tcc atc ctg gcc gtc atg aac cac atg cag gaa gcc acc ctg aat cac      197
Ser Ile Leu Ala Val Met Asn His Met Gln Glu Ala Thr Leu Asn His
    45                  50                  55 gcg aaa tct gtt ggt atc ctg ggt gat ggt ttc ggc act act ctg gaa      245
Ala Lys Ser Val Gly Ile Leu Gly Asp Gly Phe Gly Thr Thr Leu Glu
60                  65                  70                  75 atg tct aaa cgt gac ctg atg tgg gta gtg cgt cgc acc cac gta gca      293
Met Ser Lys Arg Asp Leu Met Trp Val Val Arg Arg Thr His Val Ala
                80                  85                  90 gta gag cgc tac cct act tgg ggt gac act gtg gaa gtc gag tgt tgg      341
Val Glu Arg Tyr Pro Thr Trp Gly Asp Thr Val Glu Val Glu Cys Trp
            95                 100                 105 att ggc gcg tcc ggt aac aat ggt atg cgt cgc gat ttt ctg gtc cgt      389
Ile Gly Ala Ser Gly Asn Asn Gly Met Arg Arg Asp Phe Leu Val Arg
        110                 115                 120 gac tgt aaa acg ggc gaa atc ctg acg cgt tgc acc tcc ctg agc gtt      437
Asp Cys Lys Thr Gly Glu Ile Leu Thr Arg Cys Thr Ser Leu Ser Val
    125                 130                 135 ctg atg aac acc cgc act cgt cgc ctg tct acc atc ccg gac gaa gtg      485
Leu Met Asn Thr Arg Thr Arg Arg Leu Ser Thr Ile Pro Asp Glu Val
140                 145                 150                 155 cgc ggt gag atc ggt cct gct ttc atc gat aac gtg gca gtt aaa gac      533
Arg Gly Glu Ile Gly Pro Ala Phe Ile Asp Asn Val Ala Val Lys Asp
                160                 165                 170 gac gaa atc aag aaa ctg caa aaa ctg aac gac tcc acc gcg gac tac      581
Asp Glu Ile Lys Lys Leu Gln Lys Leu Asn Asp Ser Thr Ala Asp Tyr
            175                 180                 185 atc cag ggc ggt ctg act ccg cgc tgg aac gac ctg gat gtt aat cag      629
Ile Gln Gly Gly Leu Thr Pro Arg Trp Asn Asp Leu Asp Val Asn Gln
        190                 195                 200
```

-continued

```
cat gtg aac aac ctg aaa tac gtt gct tgg gtc ttc gag act gtg ccg    677
His Val Asn Asn Leu Lys Tyr Val Ala Trp Val Phe Glu Thr Val Pro
    205                 210                 215 gac agc att ttc gaa agc cat cac att tcc tct ttt act ctg gag tac    725
Asp Ser Ile Phe Glu Ser His His Ile Ser Ser Phe Thr Leu Glu Tyr
220                     225                 230                 235 cgt cgc gaa tgt act cgc gac tcc gtt ctg cgc agc ctg acc acc gta    773
Arg Arg Glu Cys Thr Arg Asp Ser Val Leu Arg Ser Leu Thr Thr Val
                240                 245                 250 agc ggc ggt tct agc gag gca ggt ctg gtc tgc gac cat ctg ctg caa    821
Ser Gly Gly Ser Ser Glu Ala Gly Leu Val Cys Asp His Leu Leu Gln
            255                 260                 265 ctg gaa ggc ggc tcc gaa gtc ctg cgt gcg cgt acg gag tgg cgt cca    869
Leu Glu Gly Gly Ser Glu Val Leu Arg Ala Arg Thr Glu Trp Arg Pro
        270                 275                 280 aag ctg acg gat tct ttc cgc ggc atc tcc gta att ccg gcg gaa cct    917
Lys Leu Thr Asp Ser Phe Arg Gly Ile Ser Val Ile Pro Ala Glu Pro
    285                 290                 295
```

See, e.g., U.S. 2011/0165637 to Pfleger et al. Expression of BTE in the cell generates fatty acid substrates in the cell suitable for production of mcl-PHAs. Cells in preferred versions of the invention express or overexpress a gene product having a sequence comprising SEQ ID NO:20 or a sequence homologous thereto.

In some versions of the invention, the cells are genetically modified to express or overexpress a recombinant phasein gene. Examples of suitable phasins include the phasins from *Pseudomonas putida* KT2440 annotated as "Polyhydroxyalkanoate granule-associated proteins" on the UniProKB database (http://www.uniprot.org/) with locus tags of PP_5008 (SEQ ID NO:21 (coding sequence) and SEQ ID NO:22 (protein)) and PP_5007 (SEQ ID NO:23 (coding sequence) and SEQ ID NO:24 (protein)). These phasins have a high degree of homology to other phasin genes phaI and phaF, respectively. Homologs of the above-mentioned phasin genes suitable for the use in the present invention can be determined by many known methods, one of which is described below. Cells in preferred versions of the invention express or overexpress gene products having a sequence comprising SEQ ID NO:22 or a sequence homologous thereto, SEQ ID NO:24 or a sequence homologous thereto, or SEQ ID NO:22 and SEQ ID NO:24 or sequences homologous thereto.

Polyhydroxyalkanoates can be produced with the cells described herein by culturing the cells in the presence of a carbon source. The carbon source preferably includes a carbohydrate or non-lipid based carbon source, such as a fermentable sugar, a short-chain organic acid, an amino acid, or other organic molecules. Examples of suitable fermentable sugars include adonitol, arabinose, arabitol, ascorbic acid, chitin, cellubiose, dulcitol, erythrulose, fructose, fucose, galactose, glucose, gluconate, inositol, lactose, lactulose, lyxose, maltitol, maltose, maltotriose, mannitol, mannose, melezitose, melibiose, palatinose, pentaerythritol, raffinose, rhamnose, ribose, sorbitol, sorbose, starch, sucrose, trehalose, xylitol, xylose, and hydrates thereof. Examples of short-chain organic acids include acetate, propionate, lactate, pyruvate, levulinate, and succinate. Examples of amino acids include histidine, alanine, isoleucine, arginine, leucine, asparagine, lysine, aspartic acid, methionine, cysteine, phenylalanine, glutamic acid, threonine, glutamine, tryptophan, glycine, valine, ornithine, proline, serine, and tyrosine.

The carbon sources may also include an exogenous supply of fatty acids. However, in the preferred version of the invention, the culturing is performed in a medium substantially devoid of a fatty acid source, such as free fatty acids or fatty-acid containing lipids, and/or exogenous lipids in general. In various versions of the invention, the growth medium preferably includes no more than about 1 g $L^{-1}$ free fatty acid or salt thereof, no more than about 0.5 g $L^{-1}$ free fatty acid or salt thereof, no more than about 0.25 g $L^{-1}$ free fatty acid or salt thereof, no more than about 0.1 g $L^{-1}$ free fatty acid or salt thereof, no more than about 0.05 g $L^{-1}$ free fatty acid or salt thereof, no more than about 0.01 g $L^{-1}$ free fatty acid or salt thereof, no more than about 0.005 g $L^{-1}$ free fatty acid or salt thereof, or no more than about 0.001 g $L^{-1}$ free fatty acid or salt thereof.

In a preferred version of the invention, the culturing is performed in aerobic conditions. To maintain such aerobic conditions, it is preferred that the $DO_2$ content of the medium does not decrease below about 35% saturation, about 40% saturation, or about 50% saturation (Becker et al., 1997; Tseng et al., 1996).

In various versions of the invention, the culturing is performed until the cell reaches an amount of polyhydroxyalkanoate of at least about 7.5% cell dry weight, at least about 10% cell dry weight, at least about 15% cell dry weight, at least about 20% cell dry weight, at least about 25% cell dry weight, at least about 30% cell dry weight, at least about 35% cell dry weight, at least about 40% cell dry weight, at least about 45% cell dry weight, at least about 50% cell dry weight, at least about 55% cell dry weight, at least about 60% cell dry weight, at least about 65% cell dry weight, at least about 70% cell dry weight, or at least about 75% cell dry weight. Accordingly the cells of the invention are capable of producing an amount of polyhydroxyalkanoate of at least about 7.5% cell dry weight, at least about 10% cell dry weight, at least about 15% cell dry weight, at least about 20% cell dry weight, at least about 25% cell dry weight, at least about 30% cell dry weight, at least about 35% cell dry weight, at least about 40% cell dry weight, at least about 45% cell dry weight, at least about 50% cell dry weight, at least about 55% cell dry weight, at least about 60% cell dry weight, at least about 65% cell dry weight, at least about 70% cell dry weight, or at least about 75% cell dry weight.

In preferred versions of the invention, the cell produces polyhydroxyalkanoate comprised of hydroxyalkanoate monomers, wherein a large, proportion of the hydroxyalkanoate monomers comprise hydrocarbon chains comprising the same number of carbons. The number of carbons may be 7, 8, 9, 10, 11, 12, 13, 14, 15, 16, or 18 carbons. In various versions, greater than about 50%, about 55%, about 60%, about 65%, about 70%, about 75%, about 80%, or about 85% of the hydroxyalkanoate monomers comprise hydrocarbon chains comprising same number of carbons. The cell preferably produces such polyhydroxyalkanoate in the absence of exogenously supplied fatty acids.

The cells of the invention may be genetically altered to functionally delete, express, or overexpress homologs of any of the specific genes or gene products explicitly described herein. Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. Nucleic acid or gene product (amino acid) sequences of any known gene, including the genes or gene products described herein, can be determined by searching any sequence databases known the art using the gene name or accession number as a search term. Common sequence databases include GenBank (http://www.ncbi.nlm.nih.gov/genbank/), ExPASy (http://expasy.org/), KEGG (www.genome.ip/kegg/), among others. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity (e.g., identity) over 50, 100, 150 or more residues (nucleotides or amino acids) is routinely used to establish homology (e.g., over the full length of the two sequences to be compared). Higher levels of sequence similarity (e.g., identity), e.g., 30%, 35% 40%, 45% 50%, 55%, 60%, 65%, 70%, 75%, 80%, 85%, 90%, 95%, or 99% or more, can also be used to establish homology. Accordingly, homologs of the genes or gene products described herein include genes or gene products having at least about 30%, 35%, 40%, 45%, 50%, 55%, 60%, 65%, 70%, 75%, 80%, 85%, 90%, 95%, or 99% identity to the genes or gene products described herein. Methods for determining sequence similarity percentages (e.g., BLASTP and BLASTN using default parameters) are described herein and are generally available. The homologous proteins should demonstrate comparable activities and, if an enzyme, participate in the same or analogous pathways. "Orthologs" are genes in different species that evolved from a common ancestral gene by speciation. Normally, orthologs retain the same or similar function in the course of evolution. As used herein "orthologs" are included in the term "homologs".

For sequence comparison and homology determination, one sequence typically acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence based on the designated program parameters. A typical reference sequence of the invention is a nucleic acid or amino acid sequence corresponding to acsA or other genes or products described herein.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see Current Protocols in Molecular Biology, F. M. Ausubel et al., eds., Current Protocols, a joint venture between Greene Publishing Associates, Inc. and John Wiley & Sons, Inc., (supplemented through 2008)).

One example of an algorithm that is suitable for determining percent sequence identity and sequence similarity for purposes of defining homologs is the BLAST algorithm, which is described in Altschul et al., J. Mol. Biol. 215:403-410 (1990). Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001. The above-described techniques are useful in identifying homologous sequences for use in the methods described herein.

The terms "identical" or "percent identity", in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described above (or other algorithms available to persons of skill) or by visual inspection.

The phrase "substantially identical" in the context of two nucleic acids or polypeptides refers to two or more sequences or subsequences that have at least about 60%, about 65%, about 70%, about 75%, about 80%, about 85%, about 90, about 95%, about 98%, or about 99% or more nucleotide or amino acid residue identity, when compared and aligned for maximum correspondence, as measured using a sequence comparison algorithm or by visual inspection. Such "substantially identical" sequences are typically considered to be "homologous", without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, at least about 250 residues, or over the full length of the two sequences to be compared.

Terms used herein pertaining to genetic manipulation are defined as follows.

Accession numbers: The accession numbers throughout this description are derived from the NCBI database (National Center for Biotechnology Information, i.e., "GenBank"), maintained by the National Institute of Health, USA, or the KEGG (Kyoto Encyclopedia of Genes and Genomics) database, maintained by the Kyoto Encyclopedia of Genes and Genomics and sponsored in part by the University of Tokyo.

Deletion: The removal of one or more nucleotides from a nucleic acid molecule or one or more amino acids from a protein, the regions on either side being joined together.

Derived: When used with reference to a nucleic acid or protein, "derived" means that the nucleic acid or polypeptide is isolated from a described source or is at least 70%, 80%, 90%, 95%, 99%, or more identical to a nucleic acid or polypeptide included in the described source.

Endogenous: As used herein with reference to a nucleic acid molecule and a particular cell, "endogenous" refers to a nucleic acid sequence or polypeptide that is in the cell and was not introduced into the cell using recombinant engineering techniques. For example, an endogenous gene is a gene that was present in a cell when the cell was originally isolated from nature.

Exogenous: As used herein with reference to a nucleic acid molecule or polypeptide in a particular cell, "exogenous" refers to any nucleic acid molecule or polypeptide that does not originate from that particular cell as found in nature. Thus, a non-naturally-occurring nucleic acid molecule or protein is considered to be exogenous to a cell once introduced into the cell. A nucleic acid molecule or protein that is naturally-occurring also can be exogenous to a particular cell. For example, an entire coding sequence isolated from cell X is an exogenous nucleic acid with respect to cell Y once that coding sequence is introduced into cell Y, even if X and Y are the same cell type. The term "heterologous" is used herein interchangeably with "exogenous."

Expression: The process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

Introduce: When used with reference to genetic material, such as a nucleic acid, and a cell, "introduce" refers to the delivery of the genetic material to the cell in a manner such that the genetic material is capable of being expressed within the cell. Introduction of genetic material includes both transformation and transfection. Transformation encompasses techniques by which a nucleic acid molecule can be introduced into cells such as prokaryotic cells or non-animal eukaryotic cells. Transfection encompasses techniques by which a nucleic acid molecule can be introduced into cells such as animal cells. These techniques include but are not limited to introduction of a nucleic acid via conjugation, electroporation, lipofection, infection, and particle gun acceleration.

Isolated: An "isolated" biological component (such as a nucleic acid molecule, polypeptide, or cell) has been substantially separated or purified away from other biological components in which the component naturally occurs, such as other chromosomal and extrachromosomal DNA and RNA and proteins. Nucleic acid molecules and polypeptides that have been "isolated" include nucleic acid molecules and polypeptides purified by standard purification methods. The term also includes nucleic acid molecules and polypeptides prepared by recombinant expression in a cell as well as chemically synthesized nucleic acid molecules and polypeptides. In one example, "isolated" refers to a naturally-occurring nucleic acid molecule that is not immediately contiguous with both of the sequences with which it is immediately contiguous (one on the 5' end and one on the 3' end) in the naturally-occurring genome of the organism from which it is derived.

Medium chain: When used with reference to medium chain fatty acids or medium chain polyhydroxyalkanoates refers to a carbon chain length of from 7 to 18 carbons, and such as a carbon chain length of from 7 to 11 carbons.

Nucleic acid: Encompasses both RNA and DNA molecules including, without limitation, cDNA, genomic DNA, and mRNA. Nucleic acids also include synthetic nucleic acid molecules, such as those that are chemically synthesized or recombinantly produced. The nucleic acid can be double-stranded or single-stranded. Where single-stranded, the nucleic acid molecule can be the sense strand, the antisense strand, or both. In addition, the nucleic acid can be circular or linear.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. An origin of replication is operably linked to a coding sequence if the origin of replication controls the replication or copy number of the nucleic acid in the cell. Operably linked nucleic acids may or may not be contiguous.

Operon: Configurations of separate genes that are transcribed in tandem as a single messenger RNA are denoted as operons. Thus, a set of in-frame genes in close proximity under the transcriptional regulation of a single promoter constitutes an operon. Operons may be synthetically generated using the methods described herein.

Overexpress: When a gene is caused to be transcribed at an elevated rate compared to the endogenous or basal transcription rate for that gene. In some examples, overexpression additionally includes an elevated rate of translation of the gene compared to the endogenous translation rate for that gene. Methods of testing for overexpression are well known in the art, for example transcribed RNA levels can be assessed using rtPCR and protein levels can be assessed using SDS page gel analysis.

Recombinant: A recombinant nucleic acid molecule or polypeptide is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or polypeptides, such as genetic engineering techniques. "Recombinant" is also used to describe nucleic acid molecules that have been artificially manipulated but contain the same regulatory sequences and coding regions that are found in the organism from which the nucleic acid was isolated. A recombinant cell or microorganism is one that contains an exogenous nucleic acid molecule, such as a recombinant nucleic acid molecule.

Recombinant cell: A cell that comprises a recombinant nucleic acid.

Vector or expression vector: An entity comprising a nucleic acid molecule that is capable of introducing the nucleic acid, or being introduced with the nucleic acid, into a cell for expression of the nucleic acid. A vector can include nucleic acid sequences that permit it to replicate in the cell, such as an origin of replication. A vector can also include one or more selectable marker genes and other genetic elements known in the art. Examples of suitable vectors are found below.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below.

Exogenous nucleic acids encoding enzymes involved in a metabolic pathway for producing polyhydroxyalkanoates can be introduced stably or transiently into a cell using techniques well known in the art, including electroporation, calcium phosphate precipitation, DEAE-dextran mediated transfection, liposome-mediated transfection, conjugation, transduction, and the like. For stable transformation, a nucleic acid can further include a selectable marker. Suitable selectable markers include antibiotic resistance genes that confer, for example, resistance to neomycin, tetracycline, chloramphenicol, or kanamycin, genes that complement auxotrophic deficiencies, and the like. (See below for more detail.)

Various embodiments of the invention use an expression vector that includes a heterologous nucleic acid encoding a protein involved in a metabolic or biosynthetic pathway. Suitable expression vectors include, but are not limited to viral vectors, such as baculovirus vectors or those based on vaccinia virus, polio virus, adenovirus, adeno-associated virus, SV40, herpes simplex virus, and the like; phage vectors, such as bacteriophage vectors; plasmids; phagemids; cosmids; fosmids; bacterial artificial chromosomes; P1-based artificial chromosomes; yeast plasmids; yeast artificial chromosomes; and any other vectors specific for cells of interest.

Useful vectors can include one or more selectable marker genes to provide a phenotypic trait for selection of transformed cells. The selectable marker gene encodes a protein necessary for the survival or growth of transformed cells grown in a selective culture medium. Cells not transformed with the vector containing the selectable marker gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. In alternative embodiments, the selectable marker gene is one that encodes dihydrofolate reductase or confers neomycin resistance (for use in eukaryotic cell culture), or one that confers tetracycline or ampicillin resistance (for use in a prokaryotic cell, such as E. coli).

The coding sequence in the expression vector is operably linked to an appropriate expression control sequence (promoters, enhancers, and the like) to direct synthesis of the encoded gene product. Such promoters can be derived from microbial or viral sources, including CMV and SV40. Depending on the cell/vector system utilized, any of a number of suitable transcription and translation control elements, including constitutive and inducible promoters, transcription enhancer elements, transcription terminators, etc. can be used in the expression vector (see e.g., Bitter et al. (1987) *Methods in Enzymology*, 153:516-544).

Suitable promoters for use in prokaryotic cells include but are not limited to: promoters capable of recognizing the T4, T3, Sp6, and T7 polymerases; the $P_R$ and $P_L$ promoters of bacteriophage lambda; the trp, recA, heat shock, and lacZ promoters of *E. coli*; the alpha-amylase and the sigma-specific promoters of *B. subtilis*; the promoters of the bacteriophages of *Bacillus; Streptomyces* promoters; the int promoter of bacteriophage lambda; the bla promoter of the beta-lactamase gene of pBR322; and the CAT promoter of the chloramphenicol acetyl transferase gene. Prokaryotic promoters are reviewed by Glick, *J. Ind. Microbiol.* 1:277 (1987); Watson et al, Molecular Biology of the Gene, 4th Ed., Benjamin Cummins (1987); and Sambrook et al., In: *Molecular Cloning: A Laboratory Manual*, $3^{rd}$ ed., Cold Spring Harbor Laboratory Press (2001).

Non-limiting examples of suitable promoters for use within a eukaryotic cell are typically viral in origin and include the promoter of the mouse metallothionein I gene (Hamer et al. (1982) *J. Mol. Appl. Gen.* 1:273); the TK promoter of Herpes virus (McKnight (1982) *Cell* 31:355); the SV40 early promoter (Benoist et al. (1981) *Nature* (London) 290:304); the Rous sarcoma virus promoter; the cytomegalovirus promoter (Foecking et al. (1980) *Gene* 45:101); the yeast gal4 gene promoter (Johnston et al. (1982) *PNAS* (USA) 79:6971; Silver et al. (1984) *PNAS* (USA) 81:5951); and the IgG promoter (Orlandi et al. (1989) *PNAS* (USA) 86:3833).

Coding sequences can be operably linked to an inducible promoter. Inducible promoters are those wherein addition of an effector induces expression. Suitable effectors include proteins, metabolites, chemicals, or culture conditions capable of inducing expression. Suitable inducible promoters include but are not limited to the lac promoter (regulated by IPTG or analogs thereof), the lacUV5 promoter (regulated by IPTG or analogs thereof), the tac promoter (regulated by IPTG or analogs thereof), the trc promoter (regulated by IPTG or analogs thereof), the araBAD promoter (regulated by L-arabinose), the phoA promoter (regulated by phosphate starvation), the recA promoter (regulated by nalidixic acid), the proU promoter (regulated by osmolarity changes), the cst-1 promoter (regulated by glucose starvation), the tetA promoter (regulated by tetracycline), the cadA promoter (regulated by pH), the nar promoter (regulated by anaerobic conditions), the $p_L$ promoter (regulated by thermal shift), the cspA promoter (regulated by thermal shift), the T7 promoter (regulated by thermal shift), the T7-lac promoter (regulated by IPTG), the T3-lac promoter (regulated by IPTG), the T5-lac promoter (regulated by IPTG), the T4 gene 32 promoter (regulated by T4 infection), the nprM-lac promoter (regulated by IPTG), the VHb promoter (regulated by oxygen), the metallothionein promoter (regulated by heavy metals), the MMTV promoter (regulated by steroids such as dexamethasone) and variants thereof.

Alternatively, a coding sequence can be operably linked to a repressible promoter. Repressible promoters are those wherein addition of an effector represses expression. Examples of repressible promoters include but are not limited to the trp promoter (regulated by tryptophan); tetracycline-repressible promoters, such as those employed in the "TET-OFF"-brand system (Clontech, Mountain View, Calif.); and variants thereof.

In some versions, the cell is genetically modified with a heterologous nucleic acid encoding a biosynthetic pathway gene product that is operably linked to a constitutive promoter. Suitable constitutive promoters are known in the art and include constitutive adenovirus major late promoter, a constitutive MPSV promoter, and a constitutive CMV promoter.

The relative strengths of the promoters described herein are well-known in the art.

In some versions, the cell is genetically modified with an exogenous nucleic acid encoding a single protein. In other embodiments, a modified cell is one that is genetically modified with exogenous nucleic acids encoding two or more proteins. Where the cell is genetically modified to express two or more proteins, those nucleic acids can each be contained in a single or in separate expression vectors. When the nucleic acids are contained in a single expression vector, the nucleotide sequences may be operably linked to a common control element (e.g., a promoter), that is, the common control element controls expression of all of the coding sequences in the single expression vector.

When the cell is genetically modified with heterologous nucleic acids encoding two or more proteins, one of the nucleic acids can be operably linked to an inducible promoter, and one or more of the nucleic acids can be operably linked to a constitutive promoter. Alternatively, all can be operably linked to inducible promoters or all can be operably linked to constitutive promoters.

Nucleic acids encoding enzymes desired to be expressed in a cell may be codon-optimized for that particular type of cell. Codon optimization can be performed for any nucleic acid by "OPTIMUMGENE"-brand gene design system by GenScript (Piscataway, N.J.).

The introduction of a vector into a bacterial cell may be performed by protoplast transformation (Chang and Cohen (1979) *Molecular General Genetics*, 168:111-115), using competent cells (Young and Spizizen (1961) *Journal of Bacteriology*, 81:823-829; Dubnau and Davidoff-Abelson (1971) *Journal of Molecular Biology*, 56: 209-221), electroporation (Shigekawa and Dower (1988) *Biotechniques*, 6:742-751), or conjugation (Koehler and Thorne (1987) *Journal of Bacteriology*, 169:5771-5278). Commercially available vectors for expressing heterologous proteins in bacterial cells include but are not limited to pZERO, pTrc99A, pUC19, pUC18, pKK223-3, pEX1, pCAL, pET, pSPUTK, pTrxFus, pFastBac, pThioHis, pTrcHis, pTrcHis2, and pLEx, in addition to those described in the following Examples.

Methods for transforming yeast cells with heterologous DNA and producing heterologous polypeptides therefrom are disclosed by Clontech Laboratories, Inc., Palo Alto, Calif., USA (in the product protocol for the "YEAST-MAKER"-brand yeast transformation system kit); Reeves et al. (1992) *FEMS Microbiology Letters* 99:193-198; Manivasakam and Schiestl (1993) *Nucleic Acids Research* 21(18): 4414-5; and Ganeva et al. (1994) *FEMS Microbiology Letters* 121:159-64. Expression and transformation vectors for transformation into many yeast strains are available. For example, expression vectors have been developed for the following yeasts: *Candida albicans* (Kurtz, et al. (1986) *Mol. Cell. Biol.* 6:142); *Candida maltosa* (Kunze et al. (1985) *J. Basic Microbiol.* 25:141); *Hansenula polymorpha* (Gleeson et al. (1986) *J. Gen. Microbiol.* 132:3459) and Roggenkamp et al. (1986) *Mol. Gen. Genet.* 202:302); *Kluyveromyces fragilis* (Das et al. (1984) *J. Bacteriol.* 158:1165); *Kluyveromyces lactis* (De Louvencourt et al. (1983) *J. Bacteriol.* 154:737) and Van den Berg et al. (1990) *Bio/Technology* 8:135); *Pichia quillerimondii* (Kunze et al. (1985) *J. Basic Microbiol.* 25:141); *Pichia pastoris* (Cregg et al. (1985) *Mol. Cell. Biol.* 5:3376; U.S. Pat. No. 4,837, 148; and U.S. Pat. No. 4,929,555); *Saccharomyces cerevisiae* (Hinnen et al. (1978) *Proc. Natl. Acad. Sci. USA* 75:1929 and Ito et al. (1983) *J. Bacteriol.* 153:163); *Schizosaccharomyces pombe* (Beach et al. (1981) *Nature* 300: 706); and *Yarrowia lipolytica* (Davidow et al. (1985) *Curr. Genet.* 10:380-471 and Gaillardin et al. (1985) *Curr. Genet.* 10:49).

Suitable procedures for transformation of *Aspergillus* cells are described in EP 238 023 and U.S. Pat. No. 5,679, 543. Suitable methods for transforming *Fusarium* species are described by Malardier et al., *Gene,* 1989, 78:147-56 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al. (1983) *Journal of Bacteriology,* 153: 163; and Hinnen et al. (1978) *PNAS USA,* 75:1920.

The elements and method steps described herein can be used in any combination whether explicitly described or not.

All combinations of method steps as used herein can be performed in any order, unless otherwise specified or clearly implied to the contrary by the context in which the referenced combination is made.

As used herein, the singular forms "a," "an," and "the" include plural referents unless the content clearly dictates otherwise.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All patents, patent publications, and peer-reviewed publications (i.e., "references") cited herein are expressly incorporated by reference to the same extent as if each individual reference were specifically and individually indicated as being incorporated by reference. In case of conflict between the present disclosure and the incorporated references, the present disclosure controls.

It is understood that the invention is not confined to the particular construction and arrangement of parts herein illustrated and described, but embraces such modified forms thereof as come within the scope of the claims.

EXAMPLES

Summary

The following Examples present a rational approach for producing mcl-PHA homopolymer from an unrelated carbon source (i.e., glucose) in *E. coli*. A characterization of a panel of mutant *E. coli* strains to determine the impact of β-oxidation enzymes on fatty acid consumption and mcl-PHA synthesis is presented. A characterization of two PHA synthases (PhaC) and four enoyl-CoA hydratases (PhaJ) for producing mcl-PHA in *E. coli*, thereby identifying a suitable combination for making mcl-PHA, is also presented. An examination of the impact of different modes of regulating acyl-CoA synthetases on PHA titer is shown. Finally, engineering of a strain of *E. coli* to produce mcl-PHA with a composition matching the product profile of the expressed thioesterase is shown. The strategy involves constructing a strain of *E. coli* in which key genes in fatty acid β-oxidation are deleted and BTE, phaJ3 and phaC2 from *Pseudomonas aeruginosa* PAO1, and PP_0763 from *P. putida* KT2440 are overexpressed. The resulting strain is shown to produce over 15% cell dry weight (CDW) mcl-PHA when grown in minimal glucose-based media.

Materials and Methods

Bacterial Strains, Reagents, Media, and Growth Conditions

All strains used in this study are listed in Table 1. *E. coli* DH5α was used to construct and propagate plasmids. *E. coli* K-12 MG1655 ΔaraBAD was used as the base strain for studying β-oxidation and PHA production. Chemicals and reagents were purchased from Fisher Scientific (Pittsburgh, Pa.) unless otherwise specified. Enzymes used for cloning were purchased from New England Biolabs (Ipswich, Mass.). Oligonucleotides were purchased from Integrated DNA Technologies, Inc. (Coralville, Iowa) and sequences are listed in Table 2. For all growth experiments, single colonies were used to inoculate 5 mL starter cultures that were grown overnight prior to inoculation of experimental cultures. All growth experiments were performed at 37° C. in a rotary shaker (250 rpm). Where necessary, cultures were supplemented with 100 μg mL$^{-1}$ ampicillin and/or 34 μg mL$^{-1}$ chloramphenicol.

TABLE 1

Strains and plasmids used in this study.

| Strain/Plasmid | Relevant Genotype/Property | Source or Reference |
|---|---|---|
| Strains | | |
| *E. coli* K-12 MG1655 | F$^-$ λ$^-$ ilvG$^-$ rfb-50 rph-1 | ECGSC |
| *E. coli* LS5218 | F$^+$ fadR601 atoC512(Const) | ECGSC |
| *E. coli* DH10B | F$^-$ mcrA Δ(mrr-hsdRMS-mcrBC) Φ80lacZΔM15 ΔlacX74 recA1 endA1 araD139 Δ(ara, leu)7697 galU galK λ$^-$ rpsL nupG | Invitrogen |
| *E. coli* DH5α | F Φ80lacZΔM15 Δ(lacZYA-argF) U169 recA1 endA1 hsdR17 (r$_k$-, m$_k$+) phoA supE44 λ$^-$ thi$^-$1 gyrA96 relA1 | Invitrogen |
| *E. coli* DY330 | F$^-$ λ$^-$ rph-1 INV(rrnD, rrnE) ΔlacU169 gal490 pglΔ8 λcI857 Δ(cro-bioA) | (Yu et al., 2000) |
| *Pseudomonas aeruginosa* PAO1 | Source for phaC1-2, phaJ1-4 | ATCC BAA-47 ™ |
| *Pseudomonas putida* KT2440 | Source for PP_0763 | ATCC 47054 ™ |
| NRD204 | MG1655 ΔaraBAD::cat | (De Lay and Cronan, 2007) |
| araBAD | MG1655 ΔaraBAD | This work |
| A | MG1655 ΔaraBAD ΔfadA | This work |
| B | MG1655 ΔaraBAD ΔfadB | This work |
| E | MG1655 ΔaraBAD ΔfadE | This work |
| I | MG1655 ΔaraBAD ΔfadI | This work |
| J | MG1655 ΔaraBAD ΔfadJ | This work |
| R | MG1655 ΔaraBAD ΔfadR | This work |
| RA | MG1655 ΔaraBAD ΔfadR ΔfadA | This work |
| RB | MG1655 ΔaraBAD ΔfadR ΔfadB | This work |
| RE | MG1655 ΔaraBAD ΔfadR ΔfadE | This work |
| RI | MG1655 ΔaraBAD ΔfadR ΔfadI | This work |
| RJ | MG1655 ΔaraBAD ΔfadR ΔfadJ | This work |
| AI | MG1655 ΔaraBAD ΔfadA ΔfadI | This work |
| BJ | MG1655 ΔaraBAD ΔfadB ΔfadJ | This work |
| AB | MG1655 ΔaraBAD ΔfadAB | This work |
| IJ | MG1655 ΔaraBAD ΔfadIJ | This work |
| RAI | MG1655 ΔaraBAD ΔfadR ΔfadA ΔfadI | This work |
| RBJ | MG1655 ΔaraBAD ΔfadR ΔfadB ΔfadJ | This work |
| RAB | MG1655 ΔaraBAD ΔfadR ΔfadA ΔfadB | This work |
| RIJ | MG1655 ΔaraBAD ΔfadR ΔfadIJ | This work |
| ABIJ | MG1655 ΔaraBAD ΔfadAB ΔfadIJ | This work |
| RABIJ | MG1655 ΔaraBAD ΔfadR ΔfadAB ΔfadIJ | This work |
| Φ(P$_{trc}$-fadD) | MG1655 ΔaraBAD Φ(P$_{trc}$-fadD) | This work |
| SA01 | MG1655 ΔaraBAD ΔfadR ΔfadIJ fadBA::Φ(P$_{trc}$-BTE) | This work |

TABLE 1-continued

Strains and plasmids used in this study.

| Strain/Plasmid | Relevant Genotype/Property | Source or Reference |
| --- | --- | --- |
| Plasmids | | |
| pCP20 | FLP+, λ cI857+, λ $p_R$ Rep$^{ts}$, Ap$^R$, Cm$^R$ | (Cherepanov and Wackernagel, 1995) |
| pKD13 | Template plasmid for gene disruption. Kan$^R$ cassette flanked by FRT sites. Amp$^R$ | (Datsenko and Wanner, 2000) |
| pTrc99A | $P_{trc}$ promoter, pBR322 origin, Amp$^R$ | (Amann et al., 1988) |
| pTrc99A-fadD | fadD cloned as a Kpn I-Xba I fragment into pTrc99a | This work |
| pTrc99A-BTE | pTrc99A carrying BTE under Ptrc control, Amp$^R$ | (Hoover et al., 2011) |
| pMSB6 | pTrc99A with altered MCS | This work |
| pMSB6-J1 | pMSB6 containing phaJ1 gene (*P. aeruginosa*) | This work |
| pMSB6-J2 | pMSB6 containing phaJ2 gene (*P. aeruginosa*) | This work |
| pMSB6-J3 | pMSB6 containing phaJ3 gene (*P. aeruginosa*) | This work |
| pMSB6-J4 | pMSB6 containing phaJ4 gene (*P. aeruginosa*) | This work |
| pBAD33 | $P_{BAD}$ promoter, pACYC origin, Cm$^R$ | (Guzman et al., 1995) |
| pBAD33-C280* | pBAD33 araE C280* Δ281-292 | (Lee et al., 2007) |
| pBAD33*-C1 | pBAD33-C280* containing phaC1 gene (*P. aeruginosa*) | This work |
| pBAD33*-C2 | pBAD33-C280* containing phaC2 gene (*P. aeruginosa*) | This work |
| pDA-JC | pMSB6 containing phaJ3 and phaC2 genes (*P. aeruginosa*) | This work |
| pDA-JAC | pDA-JC with PP_0763 cloned between phaJ3 and phaC2 | This work |
| pBTE-int | pTrc99A containing BTE with cat-FRT cassette from pKD3 (Datsenko and Wanner, 2000) inserted 5' of lacI$^Q$ | (Youngquist et al., 2012) |

TABLE 2

Oligonucleotides used in this study.

| Primer Name | Sequence | Restriction Enzyme |
| --- | --- | --- |
| phaJ1-F | GACGATGAATTCAGGAGGTATTAATAATGAGCCAGGTCCAGAACATTC (SEQ ID NO: 25) | EcoRI |
| phaJ1-R | GACGATGGATCCGGCCCGACGGTAGGGAAA (SEQ ID NO: 26) | BamHI |
| phaJ2-F | GACGATGAATTCAGGAGGTATTAATAATGGCGCTCGATCCTGAGGTGC (SEQ ID NO: 27) | EcoRI |
| phaJ2-R | GACGATGGATCCCTTCGCTTCAGTCCGGCCGCT (SEQ ID NO: 28) | BamHI |
| phaJ3-F | GACGATGAATTCAGGAGGTATTAATAATGCCCACCGCCTGGCTCGAC (SEQ ID NO: 29) | EcoRI |
| phaJ3-R | GACGAAGGATCCTCAGCCCTGTAGCCGGCTCCA (SEQ ID NO: 30) | BamHI |
| phaJ4-F | GACGATGAATTCAGGAGGTATTAATAATGCCATTCGTACCCGTAGCAG (SEQ ID NO: 31) | EcoRI |
| phaJ4-R | GACGATGGATCCTCAGACGAAGCAGAGGCTGAG (SEQ ID NO: 32) | BamHI |
| phaC1-F | GGGGAGCTCAGGAGGTATAATTAATGAGTCAGAAGAACAATAACGAG (SEQ ID NO: 33) | SacI |
| phaC1-R | GGGGGTACCTCATCGTTCATGCACGTAGGT (SEQ ID NO: 34) | KpnI |
| phaC2-F | GGGGAGCTCAGGAGGTATAATTAATGCGAGAAAAGCAGGAATCGGG (SEQ ID NO: 35) | SacI |
| phaC2-R | GGGGGTACCTCAGCGTATATGCACGTAGGTGC (SEQ ID NO: 36) | KpnI |

TABLE 2-continued

Oligonucleotides used in this study.

| Primer Name | Sequence | Restriction Enzyme |
|---|---|---|
| phaC2-F2 | GGGTCTAGAAGGAGGTATAATTAATGCGAGAAAAGCAGGAATCGGG (SEQ ID NO: 37) | XbaI |
| phaC2-R2 | GGGAAGCTTTCAGCGTATATGCACGTAGGTGC (SEQ ID NO: 38) | HindIII |
| acs-F | GGGGGTACCAGGAGGTATAATTAATGTTGCAGACACGCATCATC (SEQ ID NO: 39) | KpnI |
| acs-R | GGGTCTAGATTACAACGTGGAAAGGAACGC (SEQ ID NO: 40) | XbaI |
| IJ::BTE-F | GGTCAGACCACTTTATTTATTTTTTTACAGGGGAGTGTTAGCGGCATGCGTTCCTATTCC (SEQ ID NO: 41) | n/a |
| IJ::BTE-R | CTCCGCCATTCAGCGCGGATTCATATAGCTTTGACCTTCTTAAACACGAGGTTCCGCCGG (SEQ ID NO: 42) | n/a |
| R::BTE-F | GAGTCCAACTTTGTTTTGCTGTGTTATGGAAATCTCACTAGCGGCATGCGTTCCTATTCC (SEQ ID NO: 43) | n/a |
| R::BTE-R | ACCCCTCGTTTGAGGGGTTTGCTCTTTAAACGGAAGGGATTAAACACGAGGTTCCGCCGG (SEQ ID NO: 44) | n/a |
| C280*-F | GGGCTCGAGTTAACCGGCACGGAACTCGCTCG (SEQ ID NO: 45) | XhoI |
| C280*-R | GGGCTCGAGTTGGTAACGAATCAGACAATTGACGGC (SEQ ID NO: 46) | XhoI |
| PfadD-kan-F | TGAATAATTGCTTGTTTTTAAAGAAAAAGAAACAGCGGCTGGTCCGCTGTGTGTAGGCTGGAGCTGCTTC (SEQ ID NO: 47) | n/a |
| PfadD-kan-R | TCGATGGTGTCAACGTAAATGATTCCGGGGATCCGTCGACC (SEQ ID NO: 48) | n/a |
| PfadD-Trc-F | CATTTACGTTGACACCATCGA (SEQ ID NO: 49) | n/a |
| PfadD-Trc-R | TCAGGCTTTATTGTCCACTTTG (SEQ ID NO: 50) | n/a |
| fadIJ::Cm-F | CAGGTCAGACCACTTTATTTATTTTTTTACAGGGGAGTGTGAAGCGGCATGCGTTCCTATTCC (SEQ ID NO: 51) | n/a |
| fadIJ::Cm-R | TTGCAGGTCAGTTGCAGTTGTTTTCCAAAAACTTTCCCCAGTGTAGGCTGGAGCTGCTTC (SEQ ID NO: 52) | n/a |
| fadR::Cm-F | TCTGGTACGACCAGATCACCTTGCGGATTCAGGAGACTGAGAAGCGGCATGCGTTCCTATTCC (SEQ ID NO: 53) | n/a |
| fadR::Cm-R | AACCCGCTCAAACACCGTCGCAATACCCTGACCCAGACCGGTGTAGGCTGGAGCTGCTTC (SEQ ID NO: 54) | n/a |

For dodecanoic acid catabolism experiments (FIGS. 2A and 3), each strain was cultured in 25 mL of LB to an optical density at 600 nm ($OD_{600}$) of 1.0. Cultures were centrifuged (1,000×g for 20 min) and resuspended in 50 mL of M9 minimal media supplemented with 0.25 g $L^{-1}$ sodium dodecanoate from a 5 g $L^{-1}$ sodium dodecanoate aqueous stock solution. This amount was chosen because higher levels impaired growth of E. coli MG1655 ΔaraBAD (data not shown). Under these conditions, soluble dodecanoic acid existed in equilibrium with a solid precipitate. After transfer, cultures were incubated at 37° C. with shaking and 2.5 mL culture samples were taken at 24 and 48 h for FAME analysis. In the case of fadD overexpression constructs, 1 mM isopropyl β-D-thiogalactopyranoside (IPTG) was added at an $OD_{600}$ of 0.02 and again after resuspension in minimal media.

For dodecanoic acid production experiments (FIG. 2B), each strain was inoculated to $OD_{600}$ of 0.05 in 5 mL of LB+0.4% (D)-glucose and induced with 1 mM IPTG at an $OD_{600}$ of 0.2. After induction, cultures were incubated for 48 h at 37° C. with shaking at which point, cultures were harvested for PHA and FAME analysis.

For shake flask experiments summarized by Table 3, 35 mL of LB was inoculated to $OD_{600}$ 0.05 and incubated with shaking until cultures reached $OD_{600}$ 1.0. Cultures were centrifuged (1,000×g for 20 min) and the cell pellet resuspended in 50 mL M9 minimal media supplemented with 2.5 g L$^{-1}$ dodecanoic acid and inducer(s) (1 mM IPTG; 0.2% (L)-arabinose). Cultures were harvested at 96 h for PHA and FAME analysis.

Figure 4A:
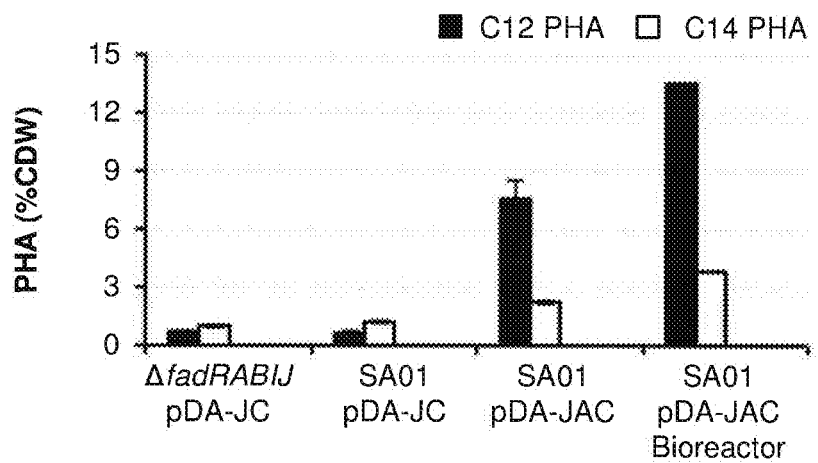
FIG. 4A shows the titer of PHA as a percentage of dry cell weight (CDW) for mcl-PHA produced in *E. coli* in the presence of exogenously fed dodecanoic acid or endogenously produced FFA. Strain ΔfadRABIJ was cultured in the presence of dodecanoic acid while SA01 (expressing BTE) was capable of endogenous FFA production in glucose minimal media. CDW was determined by quantifying 3-hydroxy fatty acid methyl esters from a PHA extraction. See Table 5 for individual CDW and PHA titer values
Figure 4B:
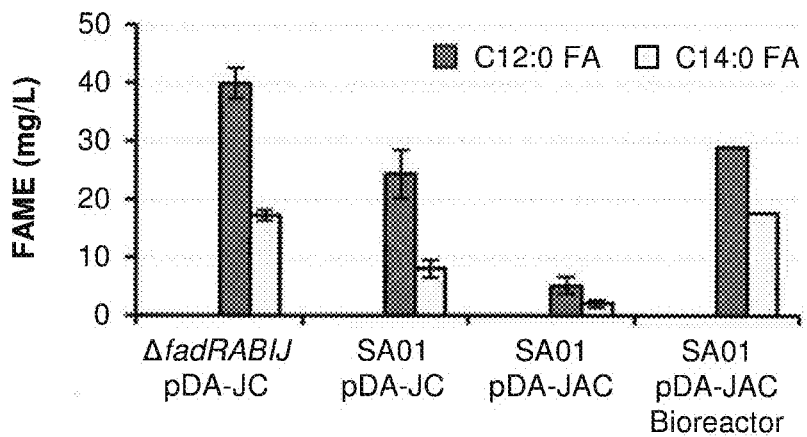
FIG. 4B shows the titer of fatty acids in *E. coli* producing mcl-PHA in the presence of exogenously fed dodecanoic acid or endogenously produced FFA. Strain ΔfadRABIJ was cultured in the presence of dodecanoic acid while SA01 (expressing BTE) was capable of endogenous FFA production in glucose minimal media. The titer of fatty acids was determined by quantifying fatty acid methyl esters (FAME) from a total lipid extraction.

For PHA production experiments detailed in Table 4 and FIG. 4, 50 mL of MOPS+1% (D)-glucose was inoculated to $OD_{600}$ of 0.05 and induced with 1 mM IPTG at an $OD_{600}$ of 0.2. After induction, cultures were incubated for 96 h at 37° C. with shaking at which point, cultures were harvested for PHA and FAME analysis. For strains lacking chromosomal expression of BTE, 0.25 g L$^{-1}$ sodium dodecanoate from a 5 g L$^{-1}$ sodium dodecanoate aqueous stock solution was added at the time of induction.

Bioreactor experiments were performed in a 3 L stirred bioreactor (Applikon Biotechnology, Inc., Schiedam, Netherlands) using a 1.0 L working volume. Temperature was maintained at 37° C. using an electric heat blanket and temperature, pH, and dissolved oxygen ($DO_2$) were monitored using specific probes. Vessel pH was maintained at 7.00±0.05 by addition of 1M NaOH or 1M HCl solutions. Agitation was provided by a single impeller with the stirrer speed set to 700 rpm. Stirrer speed was occasionally increased to ensure the $DO_2$ content did not decrease below 40% saturation in order to maintain an aerobic environment (Becker et al., 1997; Tseng et al., 1996). Air inflow was maintained at 1.5 L min$^{-1}$.

Bioreactor experiments were inoculated at an $OD_{600}$ of 0.05 with a culture of strain SA01 harboring plasmid pDA-JAC grown to an $OD_{600}$ of ≥2.5 in MOPS minimal media supplemented with 1% glucose. Induction with 1 mM IPTG occurred when the $OD_{600}$ of the bioreactor reached 0.2. The reactor was operated in batch mode with one addition of 10 g of glucose (50 mL of a 20% (w/v) glucose solution) at 24 h post-induction. The $OD_{600}$ of the culture was monitored periodically and 15 mL of culture taken every 24 h for FAME and PHA analysis. The contents of the bioreactor were harvested at 96 h post-induction for PHA and FAME analysis.

Plasmid Construction

All plasmids used in this study are listed in Table 1. Plasmid pBAD33-C280* (Lee et al., 2007) was constructed by PCR amplification of plasmid pBAD33 with primers C280*–F/R (Table 2) (Guzman et al., 1995). The PCR product was treated with Dpn I and Xho I digestion and circularized by ligation with T4 DNA ligase. Genomic DNA was isolated from *P. putida* KT2440 and *P. aeruginosa* PAO1 with a Wizard® Genomic DNA Purification Kit (Promega). PHA genes phaJ1-4 and phaC1-2 were amplified by PCR from a *P. aeruginosa* PAO1 genomic DNA template with the respective phaC and phaJ primers (Table 2). PP_0763 was amplified by PCR from a *P. putida* KT2440 genomic DNA template with primers acs-F/R (Table 2). All constructs were confirmed by DNA sequence analysis. Annotated sequence files for relevant constructs were deposited in GenBank.

Chromosome Engineering

Chromosomal gene deletions were created in *E. coli* K12 MG1655 ΔaraBAD by P1 transduction (Thomason et al., 2007) using phage lysates generated from members of the KEIO collection (Baba et al., 2006). Deletions of fadBA and fadIJ were generated as described previously using pKD13 as template (Datsenko and Wanner, 2000). Chromosomal integration of a Φ($P_{trc}$-BTE) expression cassette (a fusion of the IPTG inducible trc promoter with BTE) was constructed as described previously (Youngquist et al., 2012). Briefly, an insertion template was generated by PCR amplification of a fragment comprising lacI$^Q$-$P_{trc}$-BTE-FRT-Cm$^R$-FRT from plasmid pBTE-int. Primers contained 40 base pairs of sequence homology to regions of the *E. coli* chromosome flanking the fadBA locus (Table 2) to guide λ red mediated recombination. To construct the fadD promoter replacement, Φ($P_{trc}$-fadD), the region consisting of lacI$^Q$-$P_{trc}$-fadD was PCR amplified off of plasmid pTrc-fadD. A region of pKD13 comprising the kanamycin resistance cassette flanked by FRT sites was PCR amplified separately. The two PCR products were stitched together in a third PCR, generating a linear DNA that was integrated onto the chromosome of *E. coli* DY330 via λ red mediated recombination. For each mutant strain, resistance markers were removed by inducing FLP recombinase encoded on plasmid pCP20 which was subsequently cured by growth at a non-permissive temperature (Datsenko and Wanner, 2000). All chromosomal mutations were verified by colony PCR.

Fatty Acid and PHA Extraction and Characterization

FAME analysis was performed on 2.5 mL of culture or supernatant as described previously (Lennen et al., 2010). For PHA analysis, cells were harvested by centrifugation (3000×g for 25 min), washed with 25 mL 1× phosphate buffered saline (PBS), and lyophilized overnight. PHA content was analyzed by GC/MS based on the method of Kato et al. (Kato et al., 1996). PHA was converted to the corresponding monomer-esters by combining 2 mL of chloroform and 2 mL of 3% $H_2SO_4$ in methanol (v/v) with 10 mg of lyophilized cells in a 10 mL disposable glass centrifuge tube. 50 µL of 10 mg mL$^{-1}$ pentadecanoic acid in ethanol was added as an internal standard. The mixture was heated at 105° C. in a heat block for 24 hours followed by addition of 5 mL of 100 mg mL$^{-1}$ $NaHCO_3$ in water. The mixture was vortexed and centrifuged (1,000×g for 10 min) and the aqueous layer was removed by aspiration. The organic (chloroform) phase (1 µL) was analyzed using a Shimadzu GCMS QP2010S gas chromatograph mass spectrometer equipped with an AOC-20i auto-injector and a Restek Rxi®-5 ms column (catalog #13423). The temperature program used was as follows: 60° C. hold for 1 minute, ramp from 60° C. to 230° C. at 10° C. per minute and a final hold at 230° C. for 10 minutes. The MS was operated in scanning mode between 35 and 500 m/z.

PHA Purification and Nuclear Magnetic-Resonance Spectroscopy

PHA was extracted for analysis by nuclear magnetic-resonance (NMR) as described previously (Jiang et al., 2006) and modified based on communications with Chris Nomura (State University of New York). Briefly, lyophilized cells were washed with methanol to remove fatty acids and other impurities followed by a second lyophilization step. The material was extracted with 120 mL refluxing chloroform in a Soxhlet apparatus followed by evaporation of the chloroform to recover the purified PHA. 10-15 mg of product was dissolved in 1 mL deuterated chloroform and analyzed at room temperature on a Bruker AC-300 spectrometer for $^1$H NMR and on a Varian Mercury-300 spectrometer for $^{13}$C NMR.

Results

Effect of Fad Deletions on Dodecanoic Acid Catabolism

β-oxidation of fatty acids occurs in three stages. First, FFA are imported across the outer membrane via FadL and activated as CoA thioesters by FadD in the inner membrane. The acyl-CoA thioesters are a key regulatory signal which abrogates the DNA binding ability of FadR. In the absence of acyl-CoAs, FadR represses expression of enzymes involved in β-oxidation. Once activated, acyl-CoAs are catabolized to acetyl-CoA via an iterative pathway comprised of four enzymatic reactions (FIG. 1)—acyl-CoA dehydrogenation (FadE), enoyl-CoA hydration (FadB), (3S)-hydroxyacyl-CoA dehydrogenation (FadB), and ketoacyl-CoA thiolation (FadA). Three additional fad genes—fadK, fadI and fadJ have strong sequence homology to fadD, fadA and fadB, respectively and have been shown to be critical for anaerobic beta-oxidation (Campbell et al., 2003). Each cycle ends when FadA (or FadI) cleaves a ketoacyl-CoA to generate an acetyl-CoA and an acyl-CoA reduced in length by two carbons that is the substrate for the next round. Finally, E. coli possesses additional β-oxidation capacity in the ato genes which are responsible for processing short-chain FFAs.

The metabolic engineering strategy for producing mcl-PHA from endogenously synthesized fatty acids described herein involves the disruption of β-oxidation such that (R)-3-hydroxyacyl-CoA thioesters can be polymerized but not catabolized to acetyl-CoA. The ability of strains harboring various deletions in β-oxidation (fad) genes to catabolize dodecanoic acid after 24 and 48 h of shake flask cultivation (FIG. 2A) was therefore tested. The base strain, K12 MG1655 ΔaraBAD, was observed not to completely catabolize all of the dodecanoic acid until 48 h, while a fadR mutant was able to consume all of the dodecanoic acid within 24 h. A fadB deletion, which based on previous reports was expected to greatly impair dodecanoic acid catabolism under aerobic conditions, consumed 20% of the dodecanoic acid. A ΔfadB, ΔfadJ double knockout strain completely blocked dodecanoic acid consumption over the course of 48 h. Similarly, a ΔfadA strain consumed ~20% of the dodecanoic acid, while a ΔfadA, ΔfadI double mutant demonstrated negligible dodecanoic acid consumption. The performance of other fad strains and the effect of a fadR deletion combined with these strains, which generally improved the rate of dodecanoic acid metabolism, are shown in FIG. 2A.

To determine if metabolism of exogenously fed dodecanoic acid correlated with metabolism of endogenously produced FFAs, β-oxidation deletion strains were transformed with pTrc99a-BTE and grown for 48 h on LB supplemented with glucose (FIG. 2B). Final fatty acid concentrations and especially saturated dodecanoic acid concentrations correlated with exogenous consumption data (FIG. 2A). Specifically, strains capable of complete consumption of exogenous dodecanoic acid after 48 h accumulated little to no endogenous dodecanoic acid while strains that were the most impaired in exogenous $C_{12}$ consumption yielded the largest concentrations of endogenous $C_{12}$ FFA. While FFA uptake has been well studied (DiRusso and Black, 2004), the mechanism of FFA secretion is poorly understood. It should be noted that the data presented in FIG. 2B does not distinguish rates of FFA secretion and reuptake from catabolism of intracellular FFA.

Effect of fadD Regulation on Dodecanoic Acid Catabolism

Figure 3:
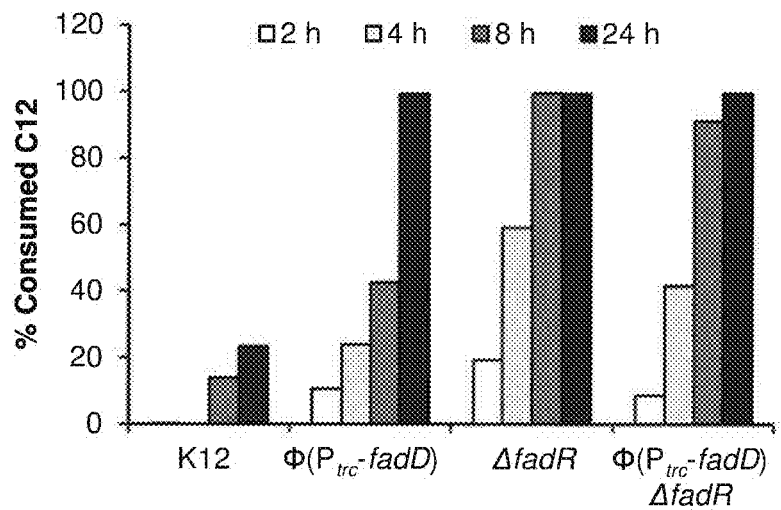
FIG. 3 shows a comparison of the effect of a fadR deletion with fadD overexpression via a chromosomal fusion of the trc promoter ($\Phi(P_{trc}$-fadD)) on exogenous dodecanoic acid metabolism in *E. coli* over a 24 h period. Data is presented as a percent of the initial fatty acid concentration.

The proposed mcl-PHA pathway involves the activation of FFA and oxidation by FadE to yield enoyl-CoA thioesters. These genes could be upregulated by increasing the rate of acyl-CoA synthesis (e.g. replacing $P_{fadD}$ with a stronger promoter), removing repression via FadR, or both. Therefore, a fadD overexpression strain was constructed by replacing the native fadD promoter with the strong, IPTG inducible trc promoter (Brosius et al., 1985). Dodecanoic acid consumption in this strain was compared with the base strain, ΔfadR, and $\Phi(P_{trc}$-fadD) ΔfadR combination strains (FIG. 3). Interestingly, the ΔfadR strain completely consumed the dodecanoic acid after 8 h while complete consumption was not observed for the $\Phi(P_{trc}$-fadD) overexpression strain until 24 h. Surprisingly, a $\Phi(P_{trc}$-fadD) ΔfadR combination strain consumed dodecanoic acid at a rate in between the $\Phi(P_{trc}$-fadD) overexpression and ΔfadR strains. Deletion of fadR may provide the additional benefit of upregulating fadE expression, which is involved in the production of enoyl-CoA thioesters in the preferred mcl-PHA strategy described herein.

Production of mcl-PHA in Fad Strains in the Presence of Exogenous Dodecanoic Acid Two PHA biosynthetic enzymes confer E. coli with the ability to synthesize mcl-PHA from enoyl-CoA thioesters, a PHA polymerase (PhaC) and an (R)-specific enoyl-CoA hydratase (PhaJ). P. aeruginosa DSM1707 phaJ1-4 have been previously characterized in E. coli LS5218 (Tsuge et al., 2003). Here, genes from P. aeruginosa PAO1 were selected based on sequence identity with DSM1707 and the ability of this strain to accumulate mcl-PHA. Individual phaJ and phaC clones were co-expressed from plasmids pMSB-6 and pBAD33-C280* respectively in LS5218 grown in the presence of exogenous dodecanoic acid as a sole carbon source. All phaJ-phaC combinations yielded mcl-PHA identified as methyl esters of 3-hydroxyacyl-chains after processing (Table 3). The observed acyl-chains ranged in length from $C_6$ to $C_{14}$ corresponding to mcl-PHA monomers ($C_6$-$C_{12}$) and components of lipid A ($C_{14}$). The combination of phaJ3 and phaC2 was selected based on the ability to produce mcl-PHA containing $C_{12}$ monomer units at yields greater than other combinations tested (Table 3).

P. aeruginosa phaC2 was cloned downstream of phaJ3 into pMSB-6 yielding pDA-JC and the plasmid was transformed into a selection of fad deletions strains for mcl-PHA production. Table 4 shows the ability of a ΔfadR, ΔfadRB. ΔfadRBJ and ΔfadRABIJ strains to accumulate mcl-PHA as well as the monomer composition of the resulting polymer. Most notably, ΔfadR and ΔfadRB strains both produced mcl-PHA with a heterogeneous monomer composition, although the fraction of $C_{12}$ monomers in the ΔfadRB strain was greatly increased over that of the ΔfadR strain. The ΔfadRBJ and ΔfadRABIJ strains were both capable of producing mcl-PHA homopolymer consisting entirely of $C_{12}$ monomers with the yield of PHA in the ΔfadRABIJ strain slightly improved over that of the ΔfadRBJ strain. This result was consistent with the relative rates of endogenous FFA production (FIG. 2B).

TABLE 3

GC/MS analysis of the composition of mcl-PHA produced in E. coli LS5218 expressing combinations of two phaC and four phaJ from P. aeruginosa PAO1 after culturing in the presence of exogenous dodecanoic acid.

| Genotype | Cell Dry Weight (g $L^{-1}$) | PHA content (wt. %) | PHA composition (wt. %) | | | |
|---|---|---|---|---|---|---|
| | | | $C_6$ | $C_8$ | $C_{10}$ | $C_{12}$ |
| phaC1 phaJ1 | 1.0 | 0.3 | 8.4 | 90.7 | 0.0 | 0.9 |
| phaC1 phaJ2 | 1.2 | 4.4 | 4.8 | 49.6 | 28.9 | 16.8 |
| phaC1 phaJ3 | 1.4 | 10.8 | 3.9 | 43.5 | 33.0 | 19.6 |
| phaC1 phaJ4 | 1.0 | 2.8 | 5.2 | 52.3 | 25.6 | 16.9 |
| phaC1 | 1.1 | 0.6 | 4.7 | 65.1 | 22.0 | 8.3 |
| phaC2 phaJ1 | 1.0 | 2.2 | 34.0 | 54.8 | 6.7 | 4.5 |

TABLE 3-continued

GC/MS analysis of the composition of mcl-PHA produced in
E. coli LS5218 expressing combinations of two phaC and
four phaJ from P. aeruginosa PAO1 after culturing
in the presence of exogenous dodecanoic acid.

| Genotype | Cell Dry Weight (g $L^{-1}$) | PHA content (wt. %) | PHA composition (wt. %) | | | |
|---|---|---|---|---|---|---|
| | | | $C_6$ | $C_8$ | $C_{10}$ | $C_{12}$ |
| phaC2 phaJ2 | 1.1 | 13.9 | 11.1 | 35.9 | 28.8 | 24.2 |
| phaC2 phaJ3 | 1.1 | 19.1 | 8.2 | 32.3 | 32.2 | 27.3 |
| phaC2 phaJ4 | 0.9 | 9.4 | 9.6 | 35.0 | 29.3 | 26.1 |
| phaC2 | 1.1 | 1.8 | 6.9 | 48.5 | 26.7 | 17.9 |

Note:
$C_6$: 3-hydroxyhexanoate;
$C_8$: 3-hydroxyoctanoate;
$C_{10}$: 3-hydroxydecanoate;
$C_{12}$: 3-hydroxydodecanoate.

TABLE 4

GC/MS analysis of the composition of mcl-PHA produced in a series
of E. coli β-oxidation deletion strains containing plasmid
pDA-JC after culturing in the presence of exogenous dodecanoic acid.

| Relevant genotype | Cell Dry Weight (g $L^{-1}$) | PHA content (wt. %) | PHA composition (wt. %) | | | |
|---|---|---|---|---|---|---|
| | | | $C_6$ | $C_8$ | $C_{10}$ | $C_{12}$ |
| ΔfadR | 0.97 ± .09 | 1.71 ± .18 | 4.0 | 30.3 | 34.0 | 31.8 |
| ΔfadRB | 0.96 ± .08 | 0.39 ± .13 | n.d. | 8.3 | 42.4 | 49.3 |
| ΔfadRBJ | 1.10 ± .19 | 0.38 ± .15 | n.d. | n.d. | n.d. | 100.0 |
| ΔfadRABIJ | 0.93 ± .02 | 0.75 ± .03 | n.d. | n.d. | n.d. | 100.0 |

Note:
$C_6$: 3-hydroxyhexanoate;
$C_8$: 3-hydroxyoctanoate;
$C_{10}$: 3-hydroxydecanoate;
$C_{12}$: 3-hydroxydodecanoate.

Accumulation of mcl-PHA in a ΔfadRABIJ Strain with Endogenous Dodecanoic Acid Production Expression of the California Bay Laurel (*Umbellularia californica*) thioesterase (BTE) in *E. coli* results in the accumulation of FFAs composed predominantly (≥80%) of saturated $C_{12}$ and unsaturated $C_{12:1}$ species with the remainder comprised mainly of $C_{14}$ and unsaturated $C_{14:1}$ FFAs (Voelker and Davies, 1994). A codon optimized version of BTE (Lennen et al., 2010) was integrated into the chromosome of *E. coli* K-12 MG1655 ΔaraBAD ΔfadR ΔfadIJ into the fadBA locus, resulting in a ΔfadRABIJ strain with one copy of the Φ($P_{trc}$-BTE) cassette. This strain (SA01) when transformed with pDA-JC and grown in MOPS minimal media supplemented with 1% glucose accumulated mcl-PHA at a % CDW on par with a ΔfadRABIJ strain cultured with exogenous dodecanoic acid (FIG. 4). A significant amount of residual dodecanoic and tetradecanoic acid was also observed indicating that there is room for further pathway optimization.

Figure 5A:
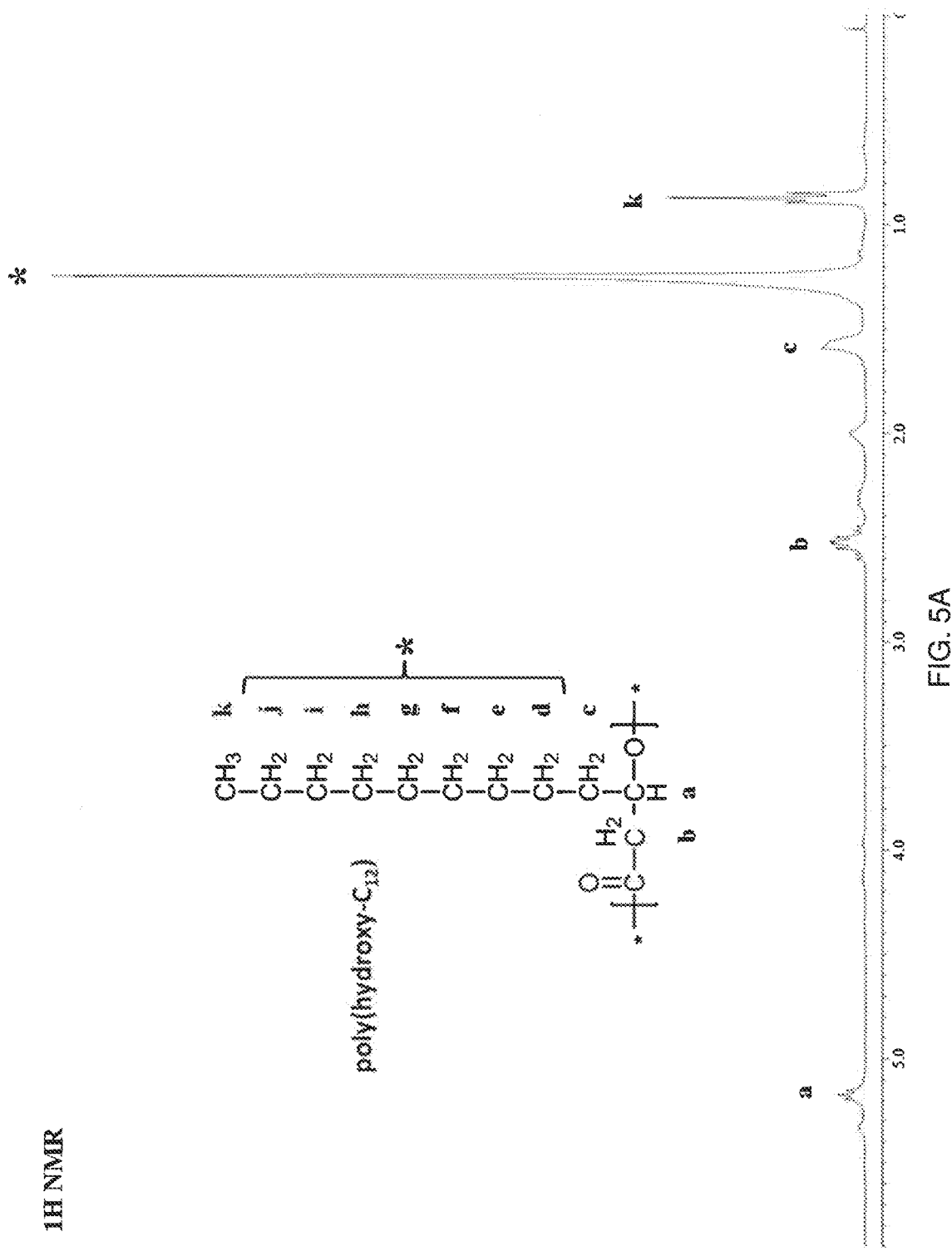
FIG. 5A shows results from $^1$H NMR of purified $C_{12}$-$C_{14}$ mcl-PHA.
Figure 5B:
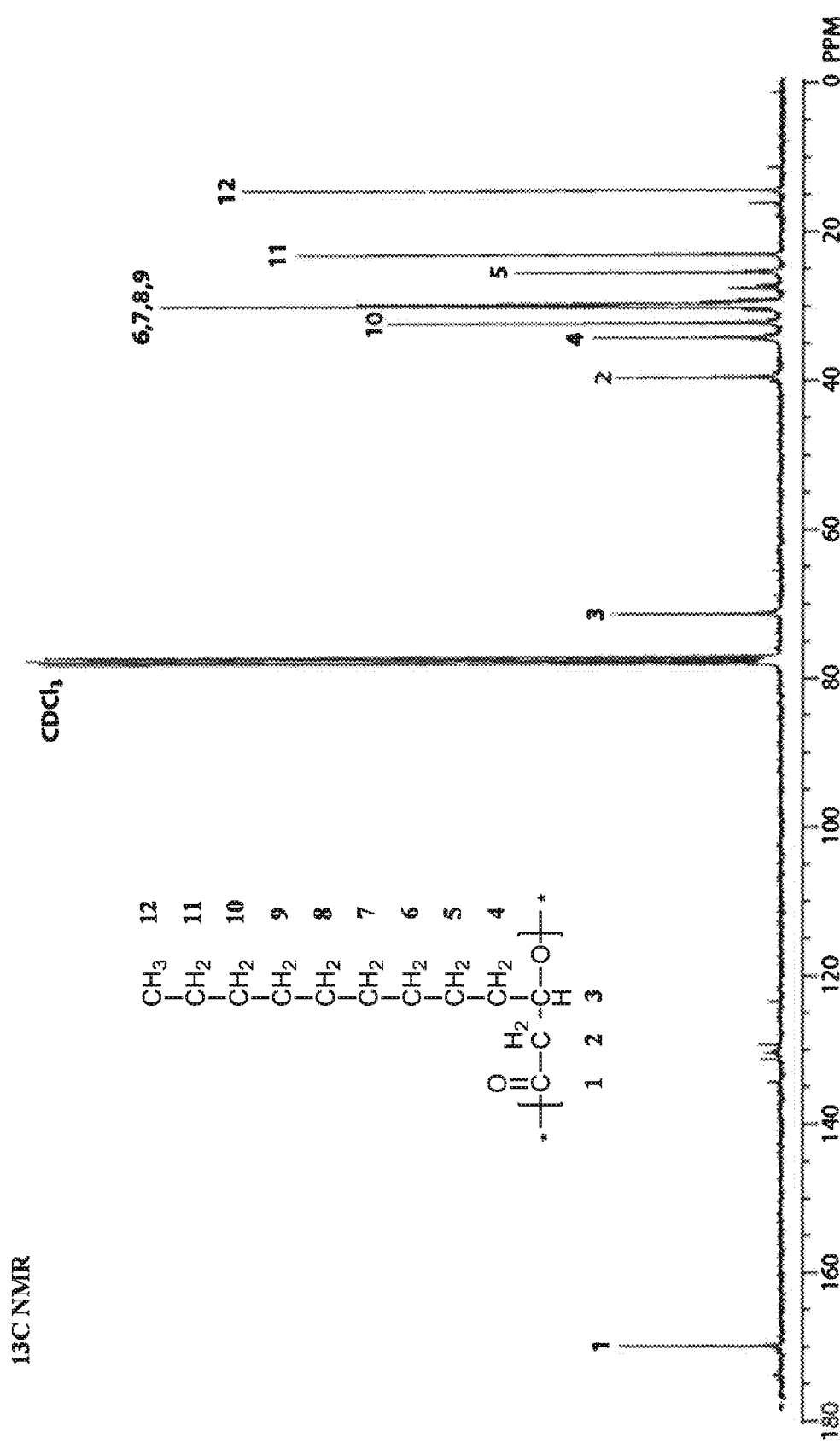
FIG. 5B shows results from $^{13}$C NMR of purified $C_{12}$-$C_{14}$ mcl-PHA.

Effect of Overexpression of PP_0763 on mcl-PHA Accumulation in a ΔfadRABIJ Strain with Endogenous Dodecanoic Acid Production Given the presence of excess FFA, it was hypothesized that the rate of fatty acyl-CoA production was not balanced with FFA synthesis. Therefore, the predicted acyl-CoA synthetase, PP_0763 from *P. putida* KT2440 was cloned between phaJ3 and phaC2 in pDA-JC resulting in pDA-JAC. Strain SA01 was transformed with pDA-JAC which resulted in the production of 9.8% CDW mcl-PHA, a 5-fold increase compared to the same strain without PP_0763 (FIG. 4, Table 5). When cultured in a 1 L bioreactor, mcl-PHA accumulation increased to 17.3% CDW after 96 h. The identity of the purified product was confirmed to be predominantly polyhydroxydodecanoate by $^1$H and $^{13}$C NMR (FIGS. 5A and 5B).

TABLE 5

Results from PHA Production Studies Shown in FIG. 4

| Genotype | Cell Dry Weight (g $L^{-1}$) | PHA content (g $L^{-1}$) | PHA content (% CDW) | PHA composition (wt. %) | | | | |
|---|---|---|---|---|---|---|---|---|
| | | | | $C_6$ | $C_8$ | $C_{10}$ | $C_{12}$ | $C_{14}$ |
| ΔfadRABIJ | 0.9 ± .02 | 0.02 | 1.7 | n.d. | n.d. | n.d. | 43.3 | 56.7 |
| SA01 | 1.2 ± .07 | 0.02 | 1.9 | n.d. | n.d. | n.d. | 34.9 | 65.1 |
| SA01-acs | 0.9 ± .04 | 0.09 | 9.8 | n.d. | n.d. | n.d. | 77.0 | 23.0 |
| Bioreactor | 1.3 | 0.23 | 17.3 | n.d. | n.d. | n.d. | 77.9 | 22.0 |

Note:
All Strains harbored plasmids expressing phaJ3 and phaC2.
ΔfadRABIJ strain was fed exogenous dodecanoic acid.
PHA values could include hydroxy-acids extracted from lipid A.
Abbreviations:
$C_6$, 3-hydroxyhexanoate;
$C_8$, 3-hydroxyoctanoate;
$C_{10}$, 3-hydroxydecanoate;
$C_{12}$, 3-hydroxydodecanoate;
$C_{14}$, 3-hydroxytetradecanoate.

Cloning and Expression of Phasin Genes

Figure 6:
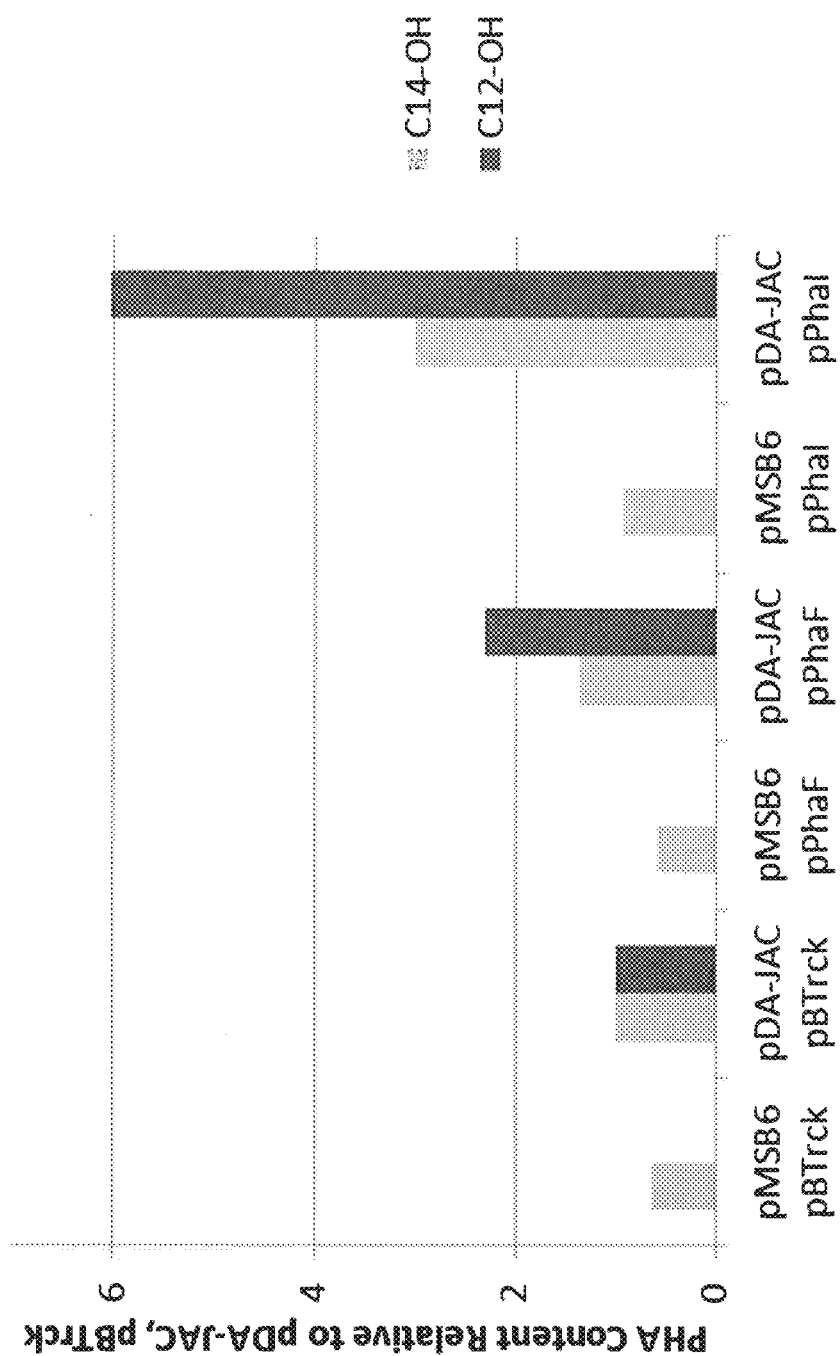
FIG. 6 shows PHA content in phasin-expressing *E. coli* strains relative to base strains. The concentration of 3-OH-fatty acid methyl esters derived from SA01 *E. coli* strains comprising various plasmids is presented relative to the concentration in SA01 *E. coli* strains comprising the pDA-JAC and pBTrck plasmids. pMSB6 and pBTrck are medium and low copy vectors, respectively, harboring IPTG inducible TRC promoters operably linked to no genes. Vector pDA-JAC is a variant of pMSB6 harboring phaJ, acs, and phaC under the control of the TRC promoter. Vector pPhaF is a variant of pBTrck harboring gene PP_5007 (UniProtKB database), which encodes a putative phasin having homology to phaF. Vector pPhaI is a variant of pBTrck harboring gene PP_5008 (UniProtKB database), which encodes a putative phasin having homology to phaI. Note: *E. coli* SA01 produces small amounts of hydroxylated C14 fatty acids (components of lipid A) that are also picked up in the PHA extraction/derivatization. The data show that expression of phasins in engineered mcl-PHA-producing *E. coli* increases PHA content relative to base strains.

Phasin genes annotated as "Polyhydroxyalkanoate granule-associated proteins" on the UniProKB database (http://www.uniprot.org/) and having locus tags PP_5008 and PP_5007 were cloned from *Pseudomonas putida* KT2440. The PP_5008 gene is homologous to phaI, and PP_5007 is homologous to phaF. Each phasin gene was expressed in the SA01 *E. coli* strain with and without the pDA-JAC vector and cultured in MOPS+1% glucose in the absence of supplemented fatty acids. As shown in FIG. 6, expression of the phasin genes drastically increased C12 and C14 polyhydroxyalkanoate production. Expression of PP_5008 in particular resulted in an unexpectedly large increase in C12 and C14 polyhydroxyalkanoate production.

DISCUSSION

Effect of Fad Deletions on Dodecanoic Acid Metabolism

Previous work has demonstrated that the ability to use fatty acids ≥$C_{12}$ as a sole carbon source is lost in the case of deletions in fadB (Dirusso, 1990), however, a fadB(A) phaC+ strain was still capable of aerobic production of mcl-PHA heteropolymer, indicating that *E. coli* can complement fadB activity (Langenbach et al., 1997; Prieto et al., 1999; Qi et al., 1997; Ren et al., 2000; Snell et al., 2002). Furthermore, a fadA insertion mutant was capable of aerobic growth on oleic acid ($C_{18:1}$) as a sole carbon source after extended incubation (<5 days) on solid media (Campbell et al., 2003), further indicating that additional β-oxidation activity is present. The data indicate both *E. coli* ΔfadA and ΔfadB mutants are capable of dodecanoic acid metabolism after 24 h, although with reduced capability compared to WT. Conversely, *E. coli* ΔfadR ΔfadA catabolized dodecanoic acid more efficiently than WT with nearly complete consumption of the dodecanoic acid after 48 h. As fadR is a negative regulator for fadIJ, it is likely that fadIJ is capable of complementing fadBA and restoring β-oxidation activity to that of WT. However, a ΔfadR ΔfadB strain did not show increased dodecanoic acid catabolism over the 48 h period. Therefore, fadJ may not be able to complement a fadB deletion as effectively as in the case of fadI with fadA.

Deletions of fadI or fadJ had a minor negative effect on dodecanoic acid metabolism compared to WT which is expected if fadBA function as the major contributor to aerobic β-oxidation. Similarly, ΔfadR ΔfadI and ΔfadR ΔfadJ strains were comparable to a ΔfadR strain. An unexpected result was the reduced rate of dodecanoic acid consumption in both a ΔfadBA and ΔfadIJ double knockout compared to WT. These data indicate that functional expression of fadBA is not essential for dodecanoic acid metabolism under the conditions tested. It is important to note that dodecanoic acid metabolism was still active in a ΔfadIJ strain which is in line with previous work that demonstrated both aerobic and anaerobic growth for a ΔfadIJ (yfcYX) strain on oleic acid (Campbell et al., 2003).

Based on the behavior of the aforementioned deletions, it was anticipated that a ΔfadA ΔfadI or ΔfadB ΔfadJ strain would be incapable of C12 metabolism. This result was confirmed for these strains, a ΔfadBA ΔfadIJ strain and for each of the strains when combined with a fadR deletion.

Comparison of fadD Overexpression and fadR Deletion on Dodecanoic Acid Metabolism Due to the ability of a fadR deletion to improve the initial rate of $C_{12}$ metabolism, it was hypothesized that overexpression of fadD would result in a similar phenotype. A chromosomal trc promoter fusion with fadD, Φ($P_{trc}$-fadD), individually and in combination with a ΔfadR strain, was therefore tested. Over a 24 h period, it was noted that Φ($P_{trc}$-fadD) was capable of improved $C_{12}$ consumption compared with WT but was not as efficient as a ΔfadR or Φ($P_{trc}$-fadD) ΔfadR combination strain. Overexpression of fadD increases the cytoplasmic acyl-CoA pool faster than in WT resulting in faster de-repression of all β-oxidation genes regulated by fadR, while in a ΔfadR strain, there is no repression of β-oxidation genes allowing for faster initial turnover of exogenous fatty acids.

Effect of Soluble Vs. Membrane Associated CoA-Synthetases

Although mcl-PHA production in strain SA01 expressing pDA-JC was achieved with a defined composition from a non-fatty acid feedstock, a large amount of endogenously produced FFA remained in the culture broth. Therefore, it was hypothesized that the limiting step in PHA biosynthesis was CoA ligation. Or put another way, it was hypothesized that intracellular FFAs were leaving the cell at a faster rate than FadD ligation with CoA, the product of which (acyl-CoA) is not exportable. Two models of the CoA synthetase reaction can be envisioned (DiRusso and Black, 2004). First, cytoplasmic FFA, freshly produced by BTE, could be directly bound by a cytosolic FadD and converted to CoA thioesters. Alternatively, cytoplasmic FFA could begin to traverse the inner cell membrane, periplasm, and outer membrane and be re-imported for FadD activation. The import of extracellular fatty acids across the outer membrane is facilitated by FadL. Once across the outer membrane, FFA traverse the periplasm and intercalate into the inner membrane. FFA then bind to the FadD active site and become phosphorylated from an ATP donor. The final CoA ligation, disassociation of FadD from the inner membrane and association of the fatty acyl-CoA with the cytoplasm likely takes place in one concerted event. If the rate of re-import is inferior to continued export (which would be down the concentration gradient) dodecanoic acid could accumulate extracellularly as was observed in the BTE expressing strains. The predicted soluble CoA-synthetase encoded by *P. putida* gene PP_0763 (acs), a medium-chain-length acyl-CoA synthetase, was therefore co-expressed. Co-expressing acs with PHA biosynthesis genes in SA01 resulted in a 5-fold increase in mcl-PHA accumulation in shake flasks and a 7.5-fold increase in 3-OH—$C_{12}$ content. This data supports the conclusion that balancing FFA production and CoA activation will be critical to maximizing mcl-PHA yields.

Bioreactor Scale-Up of mcl-PHA Production from Glucose

The PHA production strategy described herein is the first to produce a defined mcl-PHA from an unrelated carbon source. The highest mcl-PHA production (17.3% CDW) was achieved by cultivating strain SA01 pDA-JAC in a 1 L bioreactor using a fed-batch strategy. For comparison, prior studies achieved ~6% CDW of an undefined mcl-PHA in *E. coli* when grown on gluconate (Rehm and Steinbuchel, 2001) and 11.6% CDW of undefined heteropolymer in *E. coli* grown on glucose (Wang et al., 2012). Finally, recent work in both *P. putida* and *E. coli* demonstrated production of mcl-PHA homopolymer in the case of feeding exogenous fatty acids (Liu et al., 2011; Tappel et al., 2012). In *putida*, an 85% $C_{12}$-co-15% $C_{10}$ PHA was produced at 9% CDW, and in *E. coli*, a $C_{12}$ homopolymer was produced at 28.6% CDW. Based on maximum theoretical yield calculations, *E. coli* is capable of producing 0.38 g (R)-3-hydroxydodecanoic acid per g glucose fed. Thus, further optimization of the described pathway for mcl-PHA biosynthesis should lead to additional improvements in the yield on glucose as a sole carbon source. For example, improvements in PHA biosynthesis could be achieved through expression of alternative polymerases or hydratases with a higher activity for $C_{12}$ units. Besides fadJ (yfcX), there exist at least five additional genes with homology to fadB on the *E. coli* chromosome (Park and Lee, 2004). When these genes were overexpressed in *E. coli* ΔfadB in the presence of a PHA polymerase and LB+0.2% decanoic acid ($C_{10}$), a 1.3- to 2.0-fold improvement in PHA accumulation (% CDW) was achieved over an empty vector control. Along with fadJ, overexpression of ydbU, paaF and paaG resulted in the greatest improvement. By contrast, no PHA accumulation was detected in *E. coli* fadB$^+$ under the same conditions. Therefore, these gene products may have a role in both $C_{12}$ metabolism and PHA biosynthesis in *E. coli* and overexpression of these genes in addition to or in place of phaJ could improve PHA accumulation.

CONCLUSIONS

The foregoing Examples present a scheme for producing mcl-PHA homopolymer from a non-fatty acid related carbon source at up to 17.3% CDW. Examination of a series of β-oxidation deletion strains provided an understanding of knockouts suitable to completely inhibit iterative degradation of both exogenously fed and endogenously produced fatty acids. Specifically, disruption of both the aerobic and anaerobic pathways (i.e., fadBA or fadIJ) proved suitable for the proposed mcl-PHA biosynthesis pathway. Co-expression of phaJ3 and phaC2 from *P. aeruginosa* PAO1 in *E. coli* ΔfadRABIJ yielded polyhydroxydodecanoate in the presence of dodecanoic acid feeding. When the plant acyl-ACP thioesterase, BTE, was expressed in this strain, PHA comprised primarily of hydroxydodecanoate monomers was observed. Finally, expression of an additional, soluble CoA-synthetase improved production 5-fold resulting in the highest reported production of mcl-PHA for a scheme involving a thioesterase.

This strategy can be generalized to produce a variety of mcl-PHA homo- and heteropolymers, where the resulting monomer composition can be tailored based on the known fatty acid production profile of a particular acyl-ACP thioesterase. If integrated with pathways for converting renewable substrates to acetyl-CoA, processes for synthesizing designer mcl-PHA can be developed. The use of inexpensive feedstocks will ultimately allow renewable, biodegradable PHAs to compete on a cost-basis with analogous, petroleum derived plastics.

REFERENCES

Amann, E., Ochs, B., Abel, K. J., 1988. Tightly regulated tac promoter vectors useful for the expression of unfused and fused proteins in *Escherichia coli*. *Gene*. 69, 301-315.

Baba, T., Ara, T., Hasegawa, M., Takai, Y., Okumura, Y., Baba, M., Datsenko, K. A., Tomita, M., Wanner, B. L., Mori. H., 2006. Construction of *Escherichia coli* K-12 in-frame, single-gene knockout mutants: the Keio collection. *Molecular Systems Biology*. 2, 11.

Becker, S., Vlad, D., Schuster, S., Pfeiffer, P., Unden, G., 1997. Regulatory O-2 tensions for the synthesis of fermentation products in *Escherichia coli* and relation to aerobic respiration. *Archives of Microbiology*. 168, 290-296.

Brosius. J., Erfle, M., Storella, J., 1985. Spacing of the −10 and −35 regions in the tac promoter: effect on its in vivo activity. *Journal of Biological Chemistry*. 260, 3539-3541.

Campbell, J. W., Morgan-Kiss, R. M., Cronan, J. E., 2003. A new *Escherichia coli* metabolic competency: growth on fatty acids by a novel anaerobic beta-oxidation pathway. *Molecular Microbiology*. 47, 793-805.

Chen, G. Q., Wu, Q., 2005. The application of polyhydroxyalkanoates as tissue engineering materials. *Biomaterials*. 26, 6565-6578.

Cherepanov, P. P., Wackernagel, W., 1995. Gene disruption in *Escherichia coli*: TcR and KmR cassettes with the option of Flp-catalyzed excision of the antibiotic-resistance determinant. *Gene*. 158, 9-14.

Chung, A., Liu, Q., Ouyang, S. P., Wu, Q., Chen, G. Q., 2009. Microbial production of 3-hydroxydodecanoic acid by pha operon and fadBA knockout mutant of *Pseudomonas putida* KT2442 harboring tesB gene. *Applied Microbiology and Biotechnology*. 83, 513-519.

Datsenko, K. A., Wanner, B. L., 2000. One-step inactivation of chromosomal genes in *Escherichia coli* K-12 using PCR products. *Proceedings of the National Academy of Sciences of the United States of America*. 97, 6640-6645.

De Lay, N. R., Cronan, J. E., 2007. In vivo functional analyses of the type II Acyl carrier proteins of fatty acid biosynthesis. *Journal of Biological Chemistry*. 282, 20319-20328.

Dirusso, C. C., 1990. Primary sequence of the *Escherichia-coli* fadBA operon, encoding the fatty acid-oxidizing multienzyme complex, indicates a high degree of homology to eukaryotic enzymes. *Journal of Bacteriology*. 172, 6459-6468.

DiRusso, C. C., Black, P. N., 2004. Bacterial long chain fatty acid transport: Gateway to a fatty acid-responsive signaling system. *Journal of Biological Chemistry*. 279, 49563-49566.

Guzman, L. M., Belin, D., Carson, M. J., Beckwith, J., 1995. Tight Regulation, Modulation, and High-Level Expression by Vectors Containing the Arabinose PBAD Promoter. *Journal of Bacteriology*. 177, 4121-4130.

Hoover, S. W., Marner, W. D., Brownson, A. K., Lennen, R. M., Wittkopp, T. M., Yoshitani, J., Zulkifly, S., Graham, L. E., Chaston, S. D., McMahon, K. D., Pfleger, B. F., 2011. Bacterial production of free fatty acids from freshwater macroalgal cellulose. *Applied Microbiology and Biotechnology*. 91, 435-446.

Jiang, X., Ramsay, J. A., Ramsay, B. A., 2006. Acetone extraction of mcl-PHA from *Pseudomonas putida* KT2440. *Journal of Microbiological Methods*. 67, 212-219.

Kato, M., Bao, H. J., Kang, C. K., Fukui, T., Doi, Y., 1996. Production of a novel copolyester of 3-hydroxybutyric acid and medium chain length 3-hydroxyalkanaic acids by *Pseudomonas* sp 61-3 from sugars. *Applied Microbiology and Biotechnology*. 45, 363-370.

Khanna, S., Srivastava, A. K., 2005. Recent advances in microbial polyhydroxyalkanoates. *Process Biochemistry*. 40, 607-619.

Langenbach, S., Rehm, B. H. A., Steinbuchel, A., 1997. Functional expression of the PHA synthase gene PhaC1 from *Pseudomonas aeruginosa* in *Escherichia coli* results in poly(3-hydroxyalkanoate) synthesis. *Fems Microbiology Letters*. 150, 303-309.

Lee, S. K., Chou, H. H., Pfleger, B. F., Newman, J. D., Yoshikuni, Y., Keasling, J. D., 2007. Directed evolution of AraC for improved compatibility of arabinose- and lactose-inducible promoters. *Applied and Environmental Microbiology*. 73, 5711-5715.

Lennen, R. M., Braden, D. J., West, R. M., Dumesic, J. A., Pfleger, B. F., 2010. A Process for Microbial Hydrocarbon Synthesis: Overproduction of Fatty Acids in *Escherichia coli* and Catalytic Conversion to Alkanes. *Biotechnology and Bioengineering.* 106, 193-202.

Li, Z.-J., Shi, Z.-Y., Jian, J., Guo, Y.-Y., Wu, Q., Chen, G.-Q., 2010. Production of poly(3-hydroxybutyrate-co-4-hydroxybutyrate) from unrelated carbon sources by metabolically engineered *Escherichia coli*. *Metabolic Engineering.* 12, 352-359.

Liu, Q., Luo, G., Zhou, X. R., Chen, G.-Q., 2011. Biosynthesis of poly(3-hydroxydecanoate) and 3-hydroxydodecanoate dominating polyhydroxyalkanoates by beta-oxidation pathway inhibited *Pseudonmas putida*. *Metabolic Engineering.* 13, 11-17.

Meng, D.-C., Shi, Z.-Y., Wu, L.-P., Zhou, Q., Wu, Q., Chen, J.-C., Chen, G.-Q., 2012. Production and characterization of poly(3-hydroxypropionate-co-4-hydroxybutyrate) with fully controllable structures by recombinant *Escherichia coli* containing an engineered pathway. *Metabolic Engineering.* 14, 317-324.

Park, S. J., Lee, S. Y., 2004. New fadB homologous enzymes and their use in enhanced biosynthesis of medium-chain-length polyhydroxyalkanoates in fadB mutant *Escherichia coli*. *Biotechnology and Bioengineering.* 86, 681-686.

Prieto, M. A., Kellerhals, M. B., Bozzato, G. B., Radnovic, D., Witholt, B., Kessler, B., 1999. Engineering of stable recombinant bacteria for production of chiral medium-chain-length poly-3-hydroxyalkanoates. *Applied and Environmental Microbiology.* 65, 3265-3271.

Qi, Q. S., Rehm, B. H. A., Steinbuchel, A., 1997. Synthesis of poly(3-hydroxyalkanoates) in *Escherichia coli* expressing the PHA synthase gene phaC2 from *Pseudomonas aeruginosa*: comparison of PhaC1 and PhaC2. *Fems Microbiology Letters.* 157, 155-162.

Qiu, Y. Z., Han, J., Guo, J. J., Chen, G. Q., 2005. Production of Poly(3-hydroxybutyrate-co-3-hydroxyhexanoate) from gluconate and glucose by recombinant *Aeromonas hydrophila* and *Pseudomonas putida*. *Biotechnology Letters.* 27, 1381-1386.

Rehm, B. H. A., Steinbuchel, A., 2001. Heterologous expression of the acyl-acyl carrier protein thioesterase gene from the plant *Umbellularia californica* mediates polyhydroxyalkanoate biosynthesis in recombinant *Escherichia coli*. *Applied Microbiology and Biotechnology.* 55, 205-209.

Ren, Q., Sierro, N., Kellerhals, M., Kessler, B., Witholt, B., 2000. Properties of engineered poly-3-hydroxyalkanoates produced in recombinant *Escherichia coli* strains. *Applied and Environmental Microbiology.* 66, 1311-1320.

Snell, K. D., Feng, F., Zhong, L., Martin, D., Madison, L. L., 2002. YfcX enables medium-chain-length poly(3-hydroxyalkanoate) formation from fatty acids in recombinant *Escherichia coli* fadB strains. *Journal of Bacteriology.* 184, 5696-5705.

Steinbuchel, A., Valentin, H. E., 1995. Diversity of Bacterial Polyhydroxyalkanoic Acids. *Fems Microbiology Letters.* 128, 219-228.

Tappel, R. C., Wang, Q., Nomura, C. T., 2012. Precise control of repeating unit composition in biodegradable poly(3-hydroxyalkanoate) polymers synthesized by *Escherichia coli*. *Journal of bioscience and bioengineering.* 113, 480-6.

Theodorou, E. C., Theodorou, M. C., Kyriakidis, D. A., 2012. Involvement of the AtoSCDAEB regulon in the high molecular weight poly-(R)-3-hydroxybutyrate biosynthesis in phaCAB+*Escherichia coli*. *Metabolic Engineering.* 14, 354-365.

Thomason, L. C., Costantino, N., Court, D. L., 2007. *E. coli* genome manipulation by P1 transduction. Current protocols in molecular biology/edited by Frederick M. Ausubel . . . [et al.]. Chapter 1, Unit 1.17.

Tseng, C. P., Albrecht. J., Gunsalus, R. P., 1996. Effect of microaerophilic cell growth conditions on expression of the aerobic (cyoABCDE and cydAB) and anaerobic (narGHJI, frdABCD, and dmsABC) respiratory pathway genes in *Escherichia coli*. *Journal of Bacteriology.* 178, 1094-1098.

Tsuge, T., Taguchi, K., Taguchi, S., Doi, Y., 2003. Molecular characterization and properties of (R)-specific enoyl-CoA hydratases from *Pseudomonas aeruginosa*: metabolic toxols for synthesis of polyhydroxyalkanoates via fatty acid beta-oxidation. *International Journal of Biological Macromolecules.* 31, 195-205.

Voelker, T. A., Davies, H. M., 1994. Alteration of the specificity and regulation of fatty-acid synthesis of *Escherichia-coli* by expression of a plant medium-chain acyl-acyl carrier protein thioesterase. *Journal of Bacteriology.* 176, 7320-7327.

Wang, H. H., Zhou, X. R., Liu, Q. A., Chen, G. Q., 2011. Biosynthesis of polyhydroxyalkanoate homopolymers by *Pseudomonas putida*. *Applied Microbiology and Biotechnology.* 89, 1497-1507.

Wang, Q., Tappel, R. C., Zhu, C. J., Nomura, C. T., 2012. Development of a New Strategy for Production of Medium-Chain-Length Polyhydroxyalkanoates by Recombinant *Escherichia coli* via Inexpensive Non-Fatty Acid Feedstocks. *Applied and Environmental Microbiology.* 78, 519-527.

Youngquist, J. T., Lennen, R. M., Ranatunga, D. R., Bothfeld, W. H., II, W. D. M., Pfleger, B. F., 2012. Kinetic modeling of free fatty acid production in *Escherichia coli* based on continuous cultivation of a plasmid free strain. *Biotechnology and Bioengineering.* 109, 1518-1527.

Yu, D. G., Ellis, H. M., Lee, E. C., Jenkins, N. A., Copeland, N. G., Court, D. L., 2000. An efficient recombination system for chromosome engineering in *Escherichia coli*. *Proceedings of the National Academy of Sciences of the United States of America.* 97, 5978-5983.

Zhou, Q., Shi, Z.-Y., Meng, D.-C., Wu, Q., Chen, J.-C., Chen, G.-Q., 2011. Production of 3-hydroxypropionate homopolymer and poly(3-hydroxypropionate-co-4-hydroxybutyrate) copolymer by recombinant *Escherichia coli*. *Metabolic Engineering.* 13, 777-785.

What is claimed is:

1. A recombinant cell for producing polyhydroxyalkanoate comprising a recombinant R-specific enoyl-CoA hydratase gene, a recombinant PHA polymerase gene, and a recombinant acyl-CoA-synthetase gene, wherein:
   the recombinant cell is an *E. coli;*
   gene products of genes fadR, fadA, and fadI; fadR, fadB, and fadJ; or fadR, fadA, fadI, fadB, and fadJ are functionally deleted due to genetic modifications of the genes;
   the R-specific enoyl-CoA hydratase gene is a phaJ gene;
   the PHA polymerase gene is a phaC gene; and
   the recombinant cell is capable of producing polyhydroxyalkanoate.

2. The recombinant cell of claim 1 wherein gene products of genes fadR, fadA, and fadI are functionally deleted.

3. The recombinant cell of claim 1 wherein gene products of genes fadR, fadB, and fadJ are functionally deleted.

4. The recombinant cell of claim 1 wherein gene products of genes fadR, fadA, fadI, fadB and fadJ are functionally deleted.

5. The recombinant cell of claim 1 wherein the R-specific enoyl-CoA hydratase gene is phaJ3 and the PHA polymerase gene is phaC2.

6. The recombinant cell of claim 1 further comprising a recombinant thioesterase gene encoding an amino acid sequence at least about 80% identical to SEQ ID NO:20.

7. The recombinant cell of claim 1 wherein the recombinant acyl-CoA-synthetase gene encodes an amino acid sequence at least about 95% identical to SEQ ID NO:14.

8. The recombinant cell of claim 1 further comprising a recombinant phasin gene.

9. The recombinant cell of claim 1 further comprising a recombinant thioesterase gene, wherein the recombinant cell is capable of producing polyhydroxyalkanoate from carbohydrate in a medium devoid of a fatty acid source.

10. A method of producing polyhydroxyalkanoate comprising culturing a recombinant cell as recited in claim 1.

11. The method of claim 10 comprising culturing the recombinant cell in aerobic conditions.

12. The method of claim 10 comprising culturing the recombinant cell in a medium comprising a carbohydrate and substantially devoid of a fatty acid source.

13. The method of claim 10 wherein the culturing produces polyhydroxyalkanoate to at least about 7.5% cell dry weight.

14. The method of claim 10 wherein the culturing produces polyhydroxyalkanoate comprised of hydroxyalkanoate monomers, wherein greater than about 50% of the hydroxyalkanoate monomers comprise hydrocarbon chains comprising same number of carbons.

* * * * *

SEQUENCE LISTING

```
<160> NUMBER OF SEQ ID NOS: 54

<210> SEQ ID NO 1
<211> LENGTH: 2190
<212> TYPE: DNA
<213> ORGANISM: Escherichia coli
```

<400> SEQUENCE: 1

| | | | | | | |
|---|---|---|---|---|---|---|
| atgctttaca | aaggcgacac | cctgtacctt | gactggctgg | aagatggcat | tgccgaactg | 60 |
| gtatttgatg | ccccaggttc | agttaataaa | ctcgacactg | cgaccgtcgc | cagcctcggc | 120 |
| gaggccatcg | gcgtgctgga | cagcaatca | gatctaaaag | gctgctgct | gcgttcgaac | 180 |
| aaagcagcct | ttatcgtcgg | tgctgatatc | accgaatttt | tgtccctgtt | cctcgttcct | 240 |
| gaagaacagt | taagtcagtg | gctgcacttt | gccaatagcg | tgtttaatcg | cctggaagat | 300 |
| ctgccggtgc | cgaccattgc | tgccgtcaat | ggctatgcgc | tgggcggtgg | ctgcgaatgc | 360 |
| gtgctggcga | ccgattatcg | tctggcgacg | ccggatctgc | gcatcggtct | gccggaaacc | 420 |
| aaactgggca | tcatgcctgg | ctttggcggt | tctgtacgta | tgccacgtat | gctgggcgct | 480 |
| gacagtgcgc | tggaaatcat | tgccgccggt | aaagatgtcg | gcgcggatca | ggcgctgaaa | 540 |
| atcggtctgg | tggatggcgt | agtcaaagca | gaaaaactgg | ttgaaggcgc | aaaggcggtt | 600 |
| ttacgccagg | ccattaacgg | cgacctcgac | tggaaagcaa | aacgtcagcc | gaagctggaa | 660 |
| ccactaaaac | tgagcaagat | tgaagccacc | atgagcttca | ccatcgctaa | agggatggtc | 720 |
| gcacaaacag | cggggaaaca | ttatccggcc | cccatcaccg | cagtaaaaac | cattgaagct | 780 |
| gcggcccgtt | ttggtcgtga | agaagcctta | aacctggaaa | acaaaagttt | tgtcccgctg | 840 |
| gcgcatacca | cgaagcccg | cgcactggtc | ggcattttcc | ttaacgatca | atatgtaaaa | 900 |
| ggcaaagcga | agaaactcac | caaagacgtt | gaaaccccga | acaggccgc | ggtgctgggt | 960 |
| gcaggcatta | tgggcggcgg | catcgcttac | cagtctgcgt | ggaaaggcgt | gccggttgtc | 1020 |
| atgaaagata | tcaacgacaa | gtcgttaacc | ctcggcatga | ccgaagccgc | gaaactgctg | 1080 |
| aacaagcagc | ttgagcgcgg | caagatcgat | ggtctgaaaa | ctggctggcgt | gatctccaca | 1140 |
| atccacccaa | cgctcgacta | cgccggatttt | gaccgcgtgg | atattgtggt | agaagcggtt | 1200 |
| gttgaaaacc | cgaaagtgaa | aaaagccgta | ctggcagaaa | ccgaacaaaa | agtacgccag | 1260 |
| gataccgtgc | tggcgtctaa | cacttcaacc | attcctatca | gcgaactggc | caacgcgctg | 1320 |
| gaacgcccgg | aaaacttctg | cgggatgcac | ttctttaacc | cggtccaccg | aatgccgttg | 1380 |
| gtagaaatta | ttcgcggcga | gaaaagctcc | gacgaaacca | tcgcgaaagt | tgtcgcctgg | 1440 |
| gcgagcaaga | tgggcaagac | gccgattgtg | gttaacgact | gccccggctt | ctttgttaac | 1500 |
| cgcgtgctgt | tcccgtattt | cgccggtttc | agccagctgc | tgcgcgacgg | cgcggatttc | 1560 |
| cgcaagatcg | acaaagtgat | ggaaaaacag | tttggctggc | cgatgggccc | ggcatatctg | 1620 |
| ctggacgttg | tgggcattga | taccgcgcat | cacgctcagg | ctgtcatggc | agcaggcttc | 1680 |
| ccgcagcgga | tgcagaaaga | ttaccgcgat | gccatcgacg | cgctgtttga | tgccaaccgc | 1740 |
| tttggtcaga | gaacggcct | cggtttctgg | cgttataaag | aagacagcaa | aggtaagccg | 1800 |
| aagaaagaag | aagacgccgc | cgttgaagac | ctgctggcag | aagtgagcca | gccgaagcgc | 1860 |
| gatttcagcg | aagaagagat | tatcgcccgc | atgatgatcc | cgatggtcaa | cgaagtggtg | 1920 |
| cgctgtctgg | aggaaggcat | tatcgccact | ccggcggaag | cggatatggc | gctggtctac | 1980 |
| ggcctgggct | tccctccgtt | ccacggcggc | gcgttccgct | ggctggacac | cctcggtagc | 2040 |
| gcaaaatacc | tcgatatggc | acagcaatat | cagcacctcg | gcccgctgta | tgaagtgccg | 2100 |
| gaaggtctgc | gtaataaagc | gcgtcataac | gaaccgtact | atcctccggt | tgagccagcc | 2160 |
| cgtccggttg | gcgacctgaa | aacggcttaa | | | | 2190 |

<210> SEQ ID NO 2

<211> LENGTH: 729
<212> TYPE: PRT
<213> ORGANISM: Escherichia coli

<400> SEQUENCE: 2

| Met | Leu | Tyr | Lys | Gly | Asp | Thr | Leu | Tyr | Leu | Asp | Trp | Leu | Glu | Asp | Gly |
|---|---|---|---|---|---|---|---|---|---|---|---|---|---|---|---|
| 1 | | | | 5 | | | | | 10 | | | | | 15 | |

| Ile | Ala | Glu | Leu | Val | Phe | Asp | Ala | Pro | Gly | Ser | Val | Asn | Lys | Leu | Asp |
|---|---|---|---|---|---|---|---|---|---|---|---|---|---|---|---|
| | | | 20 | | | | | 25 | | | | | 30 | | |

| Thr | Ala | Thr | Val | Ala | Ser | Leu | Gly | Glu | Ala | Ile | Gly | Val | Leu | Glu | Gln |
|---|---|---|---|---|---|---|---|---|---|---|---|---|---|---|---|
| | | 35 | | | | | 40 | | | | | 45 | | | |

| Gln | Ser | Asp | Leu | Lys | Gly | Leu | Leu | Arg | Ser | Asn | Lys | Ala | Ala | Phe |
|---|---|---|---|---|---|---|---|---|---|---|---|---|---|---|
| | 50 | | | | | 55 | | | | | 60 | | | |

| Ile | Val | Gly | Ala | Asp | Ile | Thr | Glu | Phe | Leu | Ser | Leu | Phe | Leu | Val | Pro |
|---|---|---|---|---|---|---|---|---|---|---|---|---|---|---|---|
| 65 | | | | | 70 | | | | | 75 | | | | | 80 |

| Glu | Glu | Gln | Leu | Ser | Gln | Trp | Leu | His | Phe | Ala | Asn | Ser | Val | Phe | Asn |
|---|---|---|---|---|---|---|---|---|---|---|---|---|---|---|---|
| | | | | 85 | | | | | 90 | | | | | 95 | |

| Arg | Leu | Glu | Asp | Leu | Pro | Val | Pro | Thr | Ile | Ala | Ala | Val | Asn | Gly | Tyr |
|---|---|---|---|---|---|---|---|---|---|---|---|---|---|---|---|
| | | | 100 | | | | | 105 | | | | | 110 | | |

| Ala | Leu | Gly | Gly | Gly | Cys | Glu | Cys | Val | Leu | Ala | Thr | Asp | Tyr | Arg | Leu |
|---|---|---|---|---|---|---|---|---|---|---|---|---|---|---|---|
| | 115 | | | | | 120 | | | | | 125 | | | | |

| Ala | Thr | Pro | Asp | Leu | Arg | Ile | Gly | Leu | Pro | Glu | Thr | Lys | Leu | Gly | Ile |
|---|---|---|---|---|---|---|---|---|---|---|---|---|---|---|---|
| | 130 | | | | | 135 | | | | | 140 | | | | |

| Met | Pro | Gly | Phe | Gly | Gly | Ser | Val | Arg | Met | Pro | Arg | Met | Leu | Gly | Ala |
|---|---|---|---|---|---|---|---|---|---|---|---|---|---|---|---|
| 145 | | | | | 150 | | | | | 155 | | | | | 160 |

| Asp | Ser | Ala | Leu | Glu | Ile | Ile | Ala | Ala | Gly | Lys | Asp | Val | Gly | Ala | Asp |
|---|---|---|---|---|---|---|---|---|---|---|---|---|---|---|---|
| | | | | 165 | | | | | 170 | | | | | 175 | |

| Gln | Ala | Leu | Lys | Ile | Gly | Leu | Val | Asp | Gly | Val | Val | Lys | Ala | Glu | Lys |
|---|---|---|---|---|---|---|---|---|---|---|---|---|---|---|---|
| | | | 180 | | | | | 185 | | | | | 190 | | |

| Leu | Val | Glu | Gly | Ala | Lys | Ala | Val | Leu | Arg | Gln | Ala | Ile | Asn | Gly | Asp |
|---|---|---|---|---|---|---|---|---|---|---|---|---|---|---|---|
| | | 195 | | | | | 200 | | | | | 205 | | | |

| Leu | Asp | Trp | Lys | Ala | Lys | Arg | Gln | Pro | Lys | Leu | Glu | Pro | Leu | Lys | Leu |
|---|---|---|---|---|---|---|---|---|---|---|---|---|---|---|---|
| | 210 | | | | | 215 | | | | | 220 | | | | |

| Ser | Lys | Ile | Glu | Ala | Thr | Met | Ser | Phe | Thr | Ile | Ala | Lys | Gly | Met | Val |
|---|---|---|---|---|---|---|---|---|---|---|---|---|---|---|---|
| 225 | | | | | 230 | | | | | 235 | | | | | 240 |

| Ala | Gln | Thr | Ala | Gly | Lys | His | Tyr | Pro | Ala | Pro | Ile | Thr | Ala | Val | Lys |
|---|---|---|---|---|---|---|---|---|---|---|---|---|---|---|---|
| | | | | 245 | | | | | 250 | | | | | 255 | |

| Thr | Ile | Glu | Ala | Ala | Ala | Arg | Phe | Gly | Arg | Glu | Glu | Ala | Leu | Asn | Leu |
|---|---|---|---|---|---|---|---|---|---|---|---|---|---|---|---|
| | | | 260 | | | | | 265 | | | | | 270 | | |

| Glu | Asn | Lys | Ser | Phe | Val | Pro | Leu | Ala | His | Thr | Asn | Glu | Ala | Arg | Ala |
|---|---|---|---|---|---|---|---|---|---|---|---|---|---|---|---|
| | | 275 | | | | | 280 | | | | | 285 | | | |

| Leu | Val | Gly | Ile | Phe | Leu | Asn | Asp | Gln | Tyr | Val | Lys | Gly | Lys | Ala | Lys |
|---|---|---|---|---|---|---|---|---|---|---|---|---|---|---|---|
| | 290 | | | | | 295 | | | | | 300 | | | | |

| Lys | Leu | Thr | Lys | Asp | Val | Glu | Thr | Pro | Lys | Gln | Ala | Ala | Val | Leu | Gly |
|---|---|---|---|---|---|---|---|---|---|---|---|---|---|---|---|
| 305 | | | | | 310 | | | | | 315 | | | | | 320 |

| Ala | Gly | Ile | Met | Gly | Gly | Gly | Ile | Ala | Tyr | Gln | Ser | Ala | Trp | Lys | Gly |
|---|---|---|---|---|---|---|---|---|---|---|---|---|---|---|---|
| | | | | 325 | | | | | 330 | | | | | 335 | |

| Val | Pro | Val | Val | Met | Lys | Asp | Ile | Asn | Asp | Lys | Ser | Leu | Thr | Leu | Gly |
|---|---|---|---|---|---|---|---|---|---|---|---|---|---|---|---|
| | | | 340 | | | | | 345 | | | | | 350 | | |

| Met | Thr | Glu | Ala | Ala | Lys | Leu | Leu | Asn | Lys | Gln | Leu | Glu | Arg | Gly | Lys |
|---|---|---|---|---|---|---|---|---|---|---|---|---|---|---|---|
| | | 355 | | | | | 360 | | | | | 365 | | | |

| Ile | Asp | Gly | Leu | Lys | Leu | Ala | Gly | Val | Ile | Ser | Thr | Ile | His | Pro | Thr |
|---|---|---|---|---|---|---|---|---|---|---|---|---|---|---|---|
| | 370 | | | | | 375 | | | | | 380 | | | | |

| Leu | Asp | Tyr | Ala | Gly | Phe | Asp | Arg | Val | Asp | Ile | Val | Val | Glu | Ala | Val |

| | | | | | | | 385 | | | | | 390 | | | | | 395 | | | | | 400 | |
|---|---|---|---|---|---|---|---|---|---|---|---|---|---|---|---|---|---|---|---|---|---|---|---|

Val Glu Asn Pro Lys Val Lys Ala Val Leu Ala Glu Thr Glu Gln
            405                 410                 415

Lys Val Arg Gln Asp Thr Val Leu Ala Ser Asn Thr Ser Thr Ile Pro
                420                 425                 430

Ile Ser Glu Leu Ala Asn Ala Leu Glu Arg Pro Glu Asn Phe Cys Gly
            435                 440                 445

Met His Phe Phe Asn Pro Val His Arg Met Pro Leu Val Glu Ile Ile
450                 455                 460

Arg Gly Glu Lys Ser Ser Asp Glu Thr Ile Ala Lys Val Val Ala Trp
465                 470                 475                 480

Ala Ser Lys Met Gly Lys Thr Pro Ile Val Val Asn Asp Cys Pro Gly
                485                 490                 495

Phe Phe Val Asn Arg Val Leu Phe Pro Tyr Phe Ala Gly Phe Ser Gln
            500                 505                 510

Leu Leu Arg Asp Gly Ala Asp Phe Arg Lys Ile Asp Lys Val Met Glu
            515                 520                 525

Lys Gln Phe Gly Trp Pro Met Gly Pro Ala Tyr Leu Leu Asp Val Val
530                 535                 540

Gly Ile Asp Thr Ala His His Ala Gln Ala Val Met Ala Ala Gly Phe
545                 550                 555                 560

Pro Gln Arg Met Gln Lys Asp Tyr Arg Asp Ala Ile Asp Ala Leu Phe
                565                 570                 575

Asp Ala Asn Arg Phe Gly Gln Lys Asn Gly Leu Gly Phe Trp Arg Tyr
            580                 585                 590

Lys Glu Asp Ser Lys Gly Lys Pro Lys Lys Glu Glu Asp Ala Ala Val
            595                 600                 605

Glu Asp Leu Leu Ala Glu Val Ser Gln Pro Lys Arg Asp Phe Ser Glu
        610                 615                 620

Glu Glu Ile Ile Ala Arg Met Met Ile Pro Met Val Asn Glu Val Val
625                 630                 635                 640

Arg Cys Leu Glu Glu Gly Ile Ile Ala Thr Pro Ala Glu Ala Asp Met
                645                 650                 655

Ala Leu Val Tyr Gly Leu Gly Phe Pro Pro Phe His Gly Gly Ala Phe
            660                 665                 670

Arg Trp Leu Asp Thr Leu Gly Ser Ala Lys Tyr Leu Asp Met Ala Gln
            675                 680                 685

Gln Tyr Gln His Leu Gly Pro Leu Tyr Glu Val Pro Glu Gly Leu Arg
        690                 695                 700

Asn Lys Ala Arg His Asn Glu Pro Tyr Tyr Pro Val Glu Pro Ala
705                 710                 715                 720

Arg Pro Val Gly Asp Leu Lys Thr Ala
                725

<210> SEQ ID NO 3
<211> LENGTH: 2145
<212> TYPE: DNA
<213> ORGANISM: Escherichia coli

<400> SEQUENCE: 3
atggaaatga catcagcgtt taccottaat gttcgtctgg acaacattgc cgttatcacc      60
atcgacgtac cgggtgagaa aatgaatacc ctgaaggcgg agtttgcctc gcaggtgcgc     120
gccattatta agcaactccg tgaaaacaaa gagttgcgag gcgtggtgtt tgtctccgct     180

| | | |
|---|---|---|
| aaaccggaca acttcattgc tggcgcagac atcaacatga tcggcaactg caaaacggcg | 240 | |
| caagaagcgg aagctctggc gcggcagggc aacagttga tggcggagat tcatgctttg | 300 | |
| cccattcagg ttatcgcggc tattcatggc gcttgcctgg gtggtgggct ggagttggcg | 360 | |
| ctggcgtgcc acggtcgcgt ttgtactgac gatcctaaaa cggtgctcgg tttgcctgaa | 420 | |
| gtacaacttg gattgttacc cggttcaggc ggcacccagc gtttaccgcg tctgataggc | 480 | |
| gtcagcacag cattagagat gatcctcacc ggaaaacaac ttcgggcgaa acaggcatta | 540 | |
| aagctggggc tggtggatga cgttgttccg cactccattc tgctggaagc cgctgttgag | 600 | |
| ctggcaaaga aggagcgccc atcttcccgc cctctacctg tacgcgagcg tattctggcg | 660 | |
| gggccgttag gtcgtgcgct gctgttcaaa atggtcggca gaaaacaga acacaaaact | 720 | |
| caaggcaatt atccggcgac agaacgcatc ctggaggttg ttgaaacggg attagcgcag | 780 | |
| ggcaccagca gcggttatga cgccgaagct cgggcgtttg cgaactggc gatgacgcca | 840 | |
| caatcgcagg cgctgcgtag tatctttttt gccagtacgg acgtgaagaa agatcccggc | 900 | |
| agtgatgcgc cgcctgcgcc attaaacagc gtggggattt aggtggtgg cttgatgggc | 960 | |
| ggcggtattg cttatgtcac tgcttgtaaa gcggggattc cggtcagaat taaagatatc | 1020 | |
| aacccgcagg gcataaatca tgcgctgaag tacagttggg atcagctgga gggcaaagtt | 1080 | |
| cgccgtcgtc atctcaaagc cagcgaacgt gacaaacagc tggcattaat ctccggaacg | 1140 | |
| acggactatc gcggctttgc ccatcgcgat ctgattattg aagcggtgtt tgaaaatctc | 1200 | |
| gaattgaaac aacagatggt ggcggaagtt gagcaaaatt gcgccgctca taccatcttt | 1260 | |
| gcttcgaata cgtcatcttt accgattggt gatatcgccg ctcacgccac gcgacctgag | 1320 | |
| caagttatcg gcctgcattt cttcagtccg gtggaaaaaa tgccgctggt ggagattatt | 1380 | |
| cctcatgcgg ggacatcggc gcaaaccatc gctaccacag taaaactggc gaaaaaacag | 1440 | |
| ggtaaaacgc caattgtcgt gcgtgacaaa gccggttttt acgtcaatcg catcttagcg | 1500 | |
| ccttacatta tgaagctat ccgcatgttg acccaaggtg aacgggtaga gcacattgat | 1560 | |
| gccgcgctag tgaaatttgg ttttccggta ggcccaatcc aacttttgga tgaggtagga | 1620 | |
| atcgacaccg ggactaaaat tattcctgta ctggaagccg cttatggaga acgttttagc | 1680 | |
| gcgcctgcaa atgttgtttc ttcaattttg aacgacgatc gcaaaggcag aaaaaatggc | 1740 | |
| cggggttttct atctttatgg tcagaaaggg cgtaaaagca aaaaacaggt cgatcccgcc | 1800 | |
| atttacccgc tgattggcac acaagggcag gggcgaatct ccgcaccgca ggttgctgaa | 1860 | |
| cggtgtgtga tgttgatgct gaatgaagca gtacgttgtg ttgatgagca ggttatccgt | 1920 | |
| agcgtgcgtg acggggatat tggcgcggta tttggcattg gttttccgcc atttctcggt | 1980 | |
| ggaccgttcc gctatatcga ttctctcggc gcgggcgaag tggttgcaat aatgcaacga | 2040 | |
| cttgccacgc agtatggttc ccgttttacc ccttgcgagc gtttggtcga gatgggcgcg | 2100 | |
| cgtggggaaa gttttggaa acaactgca actgacctgc aataa | 2145 | |

<210> SEQ ID NO 4
<211> LENGTH: 714
<212> TYPE: PRT
<213> ORGANISM: Escherichia coli

<400> SEQUENCE: 4

Met Glu Met Thr Ser Ala Phe Thr Leu Asn Val Arg Leu Asp Asn Ile
1               5                   10                  15

Ala Val Ile Thr Ile Asp Val Pro Gly Glu Lys Met Asn Thr Leu Lys
            20                  25                  30

-continued

```
Ala Glu Phe Ala Ser Gln Val Arg Ala Ile Ile Lys Gln Leu Arg Glu
             35                  40                  45

Asn Lys Glu Leu Arg Gly Val Val Phe Val Ser Ala Lys Pro Asp Asn
 50                  55                  60

Phe Ile Ala Gly Ala Asp Ile Asn Met Ile Gly Asn Cys Lys Thr Ala
 65                  70                  75                  80

Gln Glu Ala Glu Ala Leu Ala Arg Gln Gly Gln Gln Leu Met Ala Glu
                     85                  90                  95

Ile His Ala Leu Pro Ile Gln Val Ile Ala Ala Ile His Gly Ala Cys
                100                 105                 110

Leu Gly Gly Gly Leu Glu Leu Ala Leu Ala Cys His Gly Arg Val Cys
                115                 120                 125

Thr Asp Asp Pro Lys Thr Val Leu Gly Leu Pro Glu Val Gln Leu Gly
130                 135                 140

Leu Leu Pro Gly Ser Gly Gly Thr Gln Arg Leu Pro Arg Leu Ile Gly
145                 150                 155                 160

Val Ser Thr Ala Leu Glu Met Ile Leu Thr Gly Lys Gln Leu Arg Ala
                165                 170                 175

Lys Gln Ala Leu Lys Leu Gly Leu Val Asp Asp Val Val Pro His Ser
                180                 185                 190

Ile Leu Leu Glu Ala Ala Val Glu Leu Ala Lys Lys Glu Arg Pro Ser
                195                 200                 205

Ser Arg Pro Leu Pro Val Arg Glu Arg Ile Leu Ala Gly Pro Leu Gly
        210                 215                 220

Arg Ala Leu Leu Phe Lys Met Val Gly Lys Lys Thr Glu His Lys Thr
225                 230                 235                 240

Gln Gly Asn Tyr Pro Ala Thr Glu Arg Ile Leu Glu Val Val Glu Thr
                245                 250                 255

Gly Leu Ala Gln Gly Thr Ser Ser Gly Tyr Asp Ala Glu Ala Arg Ala
                260                 265                 270

Phe Gly Glu Leu Ala Met Thr Pro Gln Ser Gln Ala Leu Arg Ser Ile
                275                 280                 285

Phe Phe Ala Ser Thr Asp Val Lys Lys Asp Pro Gly Ser Asp Ala Pro
            290                 295                 300

Pro Ala Pro Leu Asn Ser Val Gly Ile Leu Gly Gly Gly Leu Met Gly
305                 310                 315                 320

Gly Gly Ile Ala Tyr Val Thr Ala Cys Lys Ala Gly Ile Pro Val Arg
                325                 330                 335

Ile Lys Asp Ile Asn Pro Gln Gly Ile Asn His Ala Leu Lys Tyr Ser
                340                 345                 350

Trp Asp Gln Leu Glu Gly Lys Val Arg Arg Arg His Leu Lys Ala Ser
                355                 360                 365

Glu Arg Asp Lys Gln Leu Ala Leu Ile Ser Gly Thr Thr Asp Tyr Arg
        370                 375                 380

Gly Phe Ala His Arg Asp Leu Ile Ile Glu Ala Val Phe Glu Asn Leu
385                 390                 395                 400

Glu Leu Lys Gln Gln Met Val Ala Glu Val Glu Gln Asn Cys Ala Ala
                405                 410                 415

His Thr Ile Phe Ala Ser Asn Thr Ser Ser Leu Pro Ile Gly Asp Ile
                420                 425                 430

Ala Ala His Ala Thr Arg Pro Glu Gln Val Ile Gly Leu His Phe Phe
                435                 440                 445
```

| | | | | | | | | | | | |
|---|---|---|---|---|---|---|---|---|---|---|---|
|Ser|Pro|Val|Glu|Lys|Met|Pro|Leu|Val|Glu|Ile|Ile|Pro|His|Ala|Gly|
| |450| | | |455| | | |460| | | | | | |

Ser Pro Val Glu Lys Met Pro Leu Val Glu Ile Ile Pro His Ala Gly
    450             455             460

Thr Ser Gln Thr Ile Ala Thr Thr Val Lys Leu Ala Lys Lys Gln
465             470             475             480

Gly Lys Thr Pro Ile Val Val Arg Asp Lys Ala Gly Phe Tyr Val Asn
                485             490                 495

Arg Ile Leu Ala Pro Tyr Ile Asn Glu Ala Ile Arg Met Leu Thr Gln
            500             505             510

Gly Glu Arg Val Glu His Ile Asp Ala Ala Leu Val Lys Phe Gly Phe
            515             520             525

Pro Val Gly Pro Ile Gln Leu Leu Asp Glu Val Gly Ile Asp Thr Gly
    530             535             540

Thr Lys Ile Ile Pro Val Leu Glu Ala Ala Tyr Gly Glu Arg Phe Ser
545             550             555             560

Ala Pro Ala Asn Val Val Ser Ser Ile Leu Asn Asp Asp Arg Lys Gly
                565             570             575

Arg Lys Asn Gly Arg Gly Phe Tyr Leu Tyr Gly Gln Lys Gly Arg Lys
            580             585             590

Ser Lys Lys Gln Val Asp Pro Ala Ile Tyr Pro Leu Ile Gly Thr Gln
            595             600             605

Gly Gln Gly Arg Ile Ser Ala Pro Gln Val Ala Glu Arg Cys Val Met
            610             615             620

Leu Met Leu Asn Glu Ala Val Arg Cys Val Asp Glu Gln Val Ile Arg
625             630             635             640

Ser Val Arg Asp Gly Asp Ile Gly Ala Val Phe Gly Ile Gly Phe Pro
                645             650             655

Pro Phe Leu Gly Gly Pro Phe Arg Tyr Ile Asp Ser Leu Gly Ala Gly
            660             665             670

Glu Val Val Ala Ile Met Gln Arg Leu Ala Thr Gln Tyr Gly Ser Arg
            675             680             685

Phe Thr Pro Cys Glu Arg Leu Val Glu Met Gly Ala Arg Gly Glu Ser
            690             695             700

Phe Trp Lys Thr Thr Ala Thr Asp Leu Gln
705             710

<210> SEQ ID NO 5
<211> LENGTH: 1164
<212> TYPE: DNA
<213> ORGANISM: Escherichia coli

<400> SEQUENCE: 5

```
atggaacagg ttgtcattgt cgatgcaatt cgcaccccga tgggccgttc gaagggcggt      60
gcttttcgta acgtgcgtgc agaagatctc tccgctcatt aatgcgtag cctgctggcg     120 cgtaacccgg cgctggaagc ggcggccctc gacgatattt actggggttg tgtgcagcag    180
acgctggagc agggttttaa tatcgcccgt aacgcggcgc tgctggcaga agtaccacac    240
tctgtcccgg cggttaccgt taatcgcttg tgtggttcat ccatgcaggc actgcatgac    300
gcagcacgaa tgatcatgac tggcgatgcg caggcatgtc tggttggcgg cgtggagcat    360
atgggccatg tgccgatgag tcacggcgtc gattttcacc ccggcctgag ccgcaatgtc    420
gccaaagcgg cgggcatgat gggcttaacg gcagaaatgc tggcgcgtat gcacggtatc    480
agccgtgaaa tgcaggatgc ctttgccgcg cggtcacacg cccgcgcctg ggccgccacg    540
cagtcggccg catttaaaaa tgaaatcatc ccgaccggtg gtcacgatgc cgacggcgtc    600
```

-continued

```
ctgaagcagt taattacga cgaagtgatt cgcccggaaa ccaccgtgga agccctcgcc    660
acgctgcgtc cggcgtttga tccagtaaac ggtatggtaa cggcgggcac atcttctgca    720
ctttccgatg gcgcagctgc catgctggtg atgagtgaaa gccgcgccca tgaattaggt    780
cttaagccgc gcgctcgtgt gcgttcgatg gcggtcgttg gttgtgaccc atcgattatg    840
ggttacggcc cggttccggc ctcgaaactg gcgctgaaaa aagcggggct ttctgccagc    900
gatatcggcg tgtttgaaat gaacgaagcc tttgccgcgc agatcctgcc atgtattaaa    960
gatctgggac taattgagca gattgacgag aagatcaacc tcaacggtgg cgcgatcgcg   1020
ctgggtcatc cgctgggttg ttccggtgcg cgtatcagca ccacgctgct gaatctgatg   1080
gaacgcaaag acgttcagtt tggtctggcg acgatgtgta tcggtctggg tcagggtatt   1140
gcgacggtgt tgagcgggt ttaa                                           1164
```

<210> SEQ ID NO 6
<211> LENGTH: 387
<212> TYPE: PRT
<213> ORGANISM: Escherichia coli

<400> SEQUENCE: 6

```
Met Glu Gln Val Val Ile Val Asp Ala Ile Arg Thr Pro Met Gly Arg
1               5                   10                  15

Ser Lys Gly Gly Ala Phe Arg Asn Val Arg Ala Glu Asp Leu Ser Ala
            20                  25                  30

His Leu Met Arg Ser Leu Leu Ala Arg Asn Pro Ala Leu Glu Ala Ala
        35                  40                  45

Ala Leu Asp Asp Ile Tyr Trp Gly Cys Val Gln Gln Thr Leu Glu Gln
    50                  55                  60

Gly Phe Asn Ile Ala Arg Asn Ala Ala Leu Leu Ala Glu Val Pro His
65                  70                  75                  80

Ser Val Pro Ala Val Thr Val Asn Arg Leu Cys Gly Ser Ser Met Gln
                85                  90                  95

Ala Leu His Asp Ala Ala Arg Met Ile Met Thr Gly Asp Ala Gln Ala
            100                 105                 110

Cys Leu Val Gly Gly Val Glu His Met Gly His Val Pro Met Ser His
        115                 120                 125

Gly Val Asp Phe His Pro Gly Leu Ser Arg Asn Val Ala Lys Ala Ala
    130                 135                 140

Gly Met Met Gly Leu Thr Ala Glu Met Leu Ala Arg Met His Gly Ile
145                 150                 155                 160

Ser Arg Glu Met Gln Asp Ala Phe Ala Ala Arg Ser His Ala Arg Ala
                165                 170                 175

Trp Ala Ala Thr Gln Ser Ala Ala Phe Lys Asn Glu Ile Ile Pro Thr
            180                 185                 190

Gly Gly His Asp Ala Asp Gly Val Leu Lys Gln Phe Asn Tyr Asp Glu
        195                 200                 205

Val Ile Arg Pro Glu Thr Thr Val Glu Ala Leu Ala Thr Leu Arg Pro
    210                 215                 220

Ala Phe Asp Pro Val Asn Gly Met Val Thr Ala Gly Thr Ser Ser Ala
225                 230                 235                 240

Leu Ser Asp Gly Ala Ala Ala Met Leu Val Met Ser Glu Ser Arg Ala
                245                 250                 255

His Glu Leu Gly Leu Lys Pro Arg Ala Arg Val Arg Ser Met Ala Val
            260                 265                 270
```

```
Val Gly Cys Asp Pro Ser Ile Met Gly Tyr Gly Pro Val Pro Ala Ser
            275                 280                 285

Lys Leu Ala Leu Lys Lys Ala Gly Leu Ser Ala Ser Asp Ile Gly Val
        290                 295                 300

Phe Glu Met Asn Glu Ala Phe Ala Ala Gln Ile Leu Pro Cys Ile Lys
305                 310                 315                 320

Asp Leu Gly Leu Ile Glu Gln Ile Asp Glu Lys Ile Asn Leu Asn Gly
                325                 330                 335

Gly Ala Ile Ala Leu Gly His Pro Leu Gly Cys Ser Gly Ala Arg Ile
            340                 345                 350

Ser Thr Thr Leu Leu Asn Leu Met Glu Arg Lys Asp Val Gln Phe Gly
        355                 360                 365

Leu Ala Thr Met Cys Ile Gly Leu Gly Gln Gly Ile Ala Thr Val Phe
370                 375                 380

Glu Arg Val
385

<210> SEQ ID NO 7
<211> LENGTH: 1311
<212> TYPE: DNA
<213> ORGANISM: Escherichia coli

<400> SEQUENCE: 7
atgggtcagg tttaccgct ggttacccgc cagggcgatc gtatcgccat tgttagcggt        60
ttacgtacgc ctttgcccg tcaggcgacg gcttttcatg cattcccgc ggttgattta       120 gggaagatgg tggtaggcga actgctggca cgcagcgaga tccccgccga agtgattgaa       180
caactggtct ttggtcaggt cgtacaaatg cctgaagccc caacattgc gcgtgaaatt       240 gttctcggta cggaatgaa tgtacatacc gatgcttaca cgtcagccg cgcttgcgct       300 accagtttcc aggcagttgc aaacgtcgca gaaagcctga tggcgggaac tattcgagcg       360
gggattgccg tggggcaga ttcctcttcg gtattgccaa ttggcgtcag taaaaaactg       420
gcgcgcgtgc tggttgatgt caacaaagct cgtaccatga ccagcgact gaaactcttc       480 tctcgcctgc gtttgcgcga cttaatgccc gtaccacctg cggtagcaga atattctacc       540
ggcttgcgga tgggcgacac cgcagagcaa atggcgaaaa cctacggcat caccccgagaa       600 cagcaagatg cattagcgca ccgttcgcat cagcgtgccg ctcaggcatg gtcagacgga       660
aaactcaaag aagaggtgat gactgccttt atccctcctt ataaacaacc gcttgtcgaa       720
gacaacaata ttcgcggtaa ttcctcgctt gccgattacg caaagctgcg cccggcgttt       780
gatcgcaaac acggaacggt aacggcggca acagtacgc cgctgaccga tggcgcggca       840
gcggtgatcc tgatgactga atcccgggcg aaagaattag gctggtgcc gctggggtat       900 ctgcgcagct acgcatttac tgcgattgat gtctggcagg acatgttgct cggtccagcc       960
tggtcaacac cgctggcgct ggagcgtgcc ggtttgacga tgagcgatct gacattgatc      1020
gatatgcacg aagcctttgc agctcagacg ctggcgaata ttcagttgct gggtagtgaa      1080
cgttttgctc gtgaagcact ggggcgtgca catgccactg gcgaagtgga cgatagcaaa      1140
tttaacgtgc ttggcggttc gattgcttac gggcatccct tcgcggcgac cggcgcgcgg      1200
atgattaccc agacattgca tgaacttcgc cgtcgcggcg gtggatttgg tttagttacc      1260
gcctgtgctg ccggtgggct tggcgcggca atggttctgg aggcggaata a               1311

<210> SEQ ID NO 8
<211> LENGTH: 436
```

```
<212> TYPE: PRT
<213> ORGANISM: Escherichia coli

<400> SEQUENCE: 8

Met Gly Gln Val Leu Pro Leu Val Thr Arg Gln Gly Asp Arg Ile Ala
1               5                   10                  15

Ile Val Ser Gly Leu Arg Thr Pro Phe Ala Arg Gln Ala Thr Ala Phe
            20                  25                  30

His Gly Ile Pro Ala Val Asp Leu Gly Lys Met Val Val Gly Glu Leu
        35                  40                  45

Leu Ala Arg Ser Glu Ile Pro Ala Glu Val Ile Glu Gln Leu Val Phe
    50                  55                  60

Gly Gln Val Val Gln Met Pro Glu Ala Pro Asn Ile Ala Arg Glu Ile
65                  70                  75                  80

Val Leu Gly Thr Gly Met Asn Val His Thr Asp Ala Tyr Ser Val Ser
                85                  90                  95

Arg Ala Cys Ala Thr Ser Phe Gln Ala Val Ala Asn Val Ala Glu Ser
            100                 105                 110

Leu Met Ala Gly Thr Ile Arg Ala Gly Ile Ala Gly Gly Ala Asp Ser
        115                 120                 125

Ser Ser Val Leu Pro Ile Gly Val Ser Lys Lys Leu Ala Arg Val Leu
    130                 135                 140

Val Asp Val Asn Lys Ala Arg Thr Met Ser Gln Arg Leu Lys Leu Phe
145                 150                 155                 160

Ser Arg Leu Arg Leu Arg Asp Leu Met Pro Val Pro Pro Ala Val Ala
                165                 170                 175

Glu Tyr Ser Thr Gly Leu Arg Met Gly Asp Thr Ala Glu Gln Met Ala
            180                 185                 190

Lys Thr Tyr Gly Ile Thr Arg Glu Gln Gln Asp Ala Leu Ala His Arg
        195                 200                 205

Ser His Gln Arg Ala Ala Gln Ala Trp Ser Asp Gly Lys Leu Lys Glu
    210                 215                 220

Glu Val Met Thr Ala Phe Ile Pro Pro Tyr Lys Gln Pro Leu Val Glu
225                 230                 235                 240

Asp Asn Asn Ile Arg Gly Asn Ser Ser Leu Ala Asp Tyr Ala Lys Leu
                245                 250                 255

Arg Pro Ala Phe Asp Arg Lys His Gly Thr Val Thr Ala Ala Asn Ser
            260                 265                 270

Thr Pro Leu Thr Asp Gly Ala Ala Val Ile Leu Met Thr Glu Ser
        275                 280                 285

Arg Ala Lys Glu Leu Gly Leu Val Pro Leu Gly Tyr Leu Arg Ser Tyr
    290                 295                 300

Ala Phe Thr Ala Ile Asp Val Trp Gln Asp Met Leu Leu Gly Pro Ala
305                 310                 315                 320

Trp Ser Thr Pro Leu Ala Leu Glu Arg Ala Gly Leu Thr Met Ser Asp
                325                 330                 335

Leu Thr Leu Ile Asp Met His Glu Ala Phe Ala Ala Gln Thr Leu Ala
            340                 345                 350

Asn Ile Gln Leu Leu Gly Ser Glu Arg Phe Ala Arg Glu Ala Leu Gly
        355                 360                 365

Arg Ala His Ala Thr Gly Glu Val Asp Asp Ser Lys Phe Asn Val Leu
    370                 375                 380

Gly Gly Ser Ile Ala Tyr Gly His Pro Phe Ala Ala Thr Gly Ala Arg
385                 390                 395                 400
```

```
Met Ile Thr Gln Thr Leu His Glu Leu Arg Arg Gly Gly Gly Phe
            405                 410                 415

Gly Leu Val Thr Ala Cys Ala Ala Gly Leu Gly Ala Ala Met Val
            420                 425                 430

Leu Glu Ala Glu
        435

<210> SEQ ID NO 9
<211> LENGTH: 720
<212> TYPE: DNA
<213> ORGANISM: Escherichia coli

<400> SEQUENCE: 9
atggtcatta aggcgcaaag cccggcgggt ttcgcggaag agtacattat tgaaagtatc      60
tggaataacc gcttccctcc cgggactatt ttgcccgcag aacgtgaact ttcagaatta    120
attggcgtaa cgcgtactac gttacgtgaa gtgttacagc gtctggcacg agatggctgg    180
ttgaccattc aacatggcaa gccgacgaag gtgaataatt tctgggaaac ttccggttta    240
aatatccttg aaacactggc gcgactggat cacgaaagtg tgccgcagct tattgataat    300
ttgctgtcgg tgcgtaccaa tatttccact attttattc gcaccgcgtt tcgtcagcat    360
cccgataaag cgcaggaagt gctggctacc gctaatgaag tggccgatca cgccgatgcc    420
tttgccgagc tggattacaa catattccgc ggcctggcgt ttgcttccgg caacccgatt    480
tacggtctga ttcttaacgg gatgaaaggg ctgtatacgc gtattggtcg tcactatttc    540
gccaatccga agcgcgcag tctggcgctg ggcttctacc acaaactgtc ggcgttgtgc    600
agtgaaggcg cgcacgatca ggtgtacgaa acagtgcgtc gctatgggca tgagagtggc    660
gagatttggc accggatgca gaaaaatctg ccgggtgatt tagccattca ggggcgataa    720

<210> SEQ ID NO 10
<211> LENGTH: 239
<212> TYPE: PRT
<213> ORGANISM: Escherichia coli

<400> SEQUENCE: 10

Met Val Ile Lys Ala Gln Ser Pro Ala Gly Phe Ala Glu Glu Tyr Ile
1               5                   10                  15

Ile Glu Ser Ile Trp Asn Asn Arg Phe Pro Pro Gly Thr Ile Leu Pro
            20                  25                  30

Ala Glu Arg Glu Leu Ser Glu Leu Ile Gly Val Thr Arg Thr Thr Leu
        35                  40                  45

Arg Glu Val Leu Gln Arg Leu Ala Arg Asp Gly Trp Leu Thr Ile Gln
    50                  55                  60

His Gly Lys Pro Thr Lys Val Asn Asn Phe Trp Glu Thr Ser Gly Leu
65                  70                  75                  80

Asn Ile Leu Glu Thr Leu Ala Arg Leu Asp His Glu Ser Val Pro Gln
                85                  90                  95

Leu Ile Asp Asn Leu Leu Ser Val Arg Thr Asn Ile Ser Thr Ile Phe
            100                 105                 110

Ile Arg Thr Ala Phe Arg Gln His Pro Asp Lys Ala Gln Glu Val Leu
        115                 120                 125

Ala Thr Ala Asn Glu Val Ala Asp His Ala Asp Ala Phe Ala Glu Leu
    130                 135                 140

Asp Tyr Asn Ile Phe Arg Gly Leu Ala Phe Ala Ser Gly Asn Pro Ile
145                 150                 155                 160
```

Tyr Gly Leu Ile Leu Asn Gly Met Lys Gly Leu Tyr Thr Arg Ile Gly
            165                 170                 175

Arg His Tyr Phe Ala Asn Pro Glu Ala Arg Ser Leu Ala Leu Gly Phe
        180                 185                 190

Tyr His Lys Leu Ser Ala Leu Cys Ser Glu Gly Ala His Asp Gln Val
    195                 200                 205

Tyr Glu Thr Val Arg Arg Tyr Gly His Glu Ser Gly Glu Ile Trp His
  210                 215                 220

Arg Met Gln Lys Asn Leu Pro Gly Asp Leu Ala Ile Gln Gly Arg
225                 230                 235

<210> SEQ ID NO 11
<211> LENGTH: 1686
<212> TYPE: DNA
<213> ORGANISM: Escherichia coli

<400> SEQUENCE: 11

| | | | | | |
|---|---|---|---|---|---|
| ttgaagaagg | tttggcttaa | ccgttatccc | gcggacgttc | cgacggagat | caaccctgac | 60 |
| cgttatcaat | ctctggtaga | tatgtttgag | cagtcggtcg | cgcgctacgc | cgatcaacct | 120 |
| gcgtttgtga | atatggggga | ggtaatgacc | ttccgcaagc | tggaagaacg | cagtcgcgcg | 180 |
| tttgccgctt | atttgcaaca | agggttgggg | ctgaagaaag | gcgatcgcgt | tgcgttgatg | 240 |
| atgcctaatt | tattgcaata | tccggtggcg | ctgtttggca | ttttgcgtgc | cgggatgatc | 300 |
| gtcgtaaacg | ttaacccgtt | gtataccccg | cgtgagcttg | agcatcagct | taacgatagc | 360 |
| ggcgcatcgg | cgattgttat | cgtgtctaac | tttgctcaca | cactggaaaa | agtggttgat | 420 |
| aaaaccgccg | ttcagcacgt | aattctgacc | cgtatgggcg | atcagctatc | tacggcaaaa | 480 |
| ggcacggtag | tcaatttcgt | tgttaaatac | atcaagcgtt | tggtgccgaa | ataccatctg | 540 |
| ccagatgcca | tttcatttcg | tagcgcactg | cataacggct | accggatgca | gtacgtcaaa | 600 |
| cccgaactgg | tgccggaaga | tttagctttt | ctgcaataca | ccggcggcac | cactggtgtg | 660 |
| gcgaaaggcg | cgatgctgac | tcaccgcaat | atgctggcga | acctggaaca | ggttaacgcg | 720 |
| acctatggtc | cgctgttgca | tccgggcaaa | gagctggtgg | tgacggcgct | gccgctgtat | 780 |
| cacattttg | ccctgaccat | taactgcctg | ctgtttatcg | aactgggtgg | cagaacctg | 840 |
| cttatcacta | acccgcgcga | tattccaggg | ttggtaaaag | agttagcgaa | atatccgttt | 900 |
| accgctatca | cgggcgttaa | caccttgttc | aatgcgttgc | tgaacaataa | agagttccag | 960 |
| cagctggatt | tctccagtct | gcatctttcc | gcaggcggtg | ggatgccagt | gcagcaagtg | 1020 |
| gtggcagagc | gttgggtgaa | actgaccgga | cagtatctgc | tggaaggcta | tggccttacc | 1080 |
| gagtgtgcgc | cgctggtcag | cgttaaccca | tatgatattg | attatcatag | tggtagcatc | 1140 |
| ggtttgccgg | tgccgtcgac | ggaagccaaa | ctggtggatg | atgatgataa | tgaagtacca | 1200 |
| ccaggtcaac | cgggtgagct | tgtgtgtcaaa | ggaccgcagg | tgatgctggg | ttactggcag | 1260 |
| cgtcccgatg | ctaccgatga | aatcatcaaa | aatggctggt | acacaccgg | cgacatcgcg | 1320 |
| gtaatggatg | aagaaggatt | cctgcgcatt | gtcgatcgta | aaaagacat | gattctggtt | 1380 |
| tccggtttta | acgtctatcc | caacgagatt | gaagatgtcg | tcatgcagca | tcctggcgta | 1440 |
| caggaagtcg | cggctgttgg | cgtaccttcc | ggctccagtg | gtgaagcggt | gaaaatcttc | 1500 |
| gtagtgaaaa | aagatccatc | gcttaccgaa | gagtcactgg | tgactttttg | ccgccgtcag | 1560 |
| ctcacgggat | acaaagtacc | gaagctggtg | gagtttcgtg | atgagttacc | gaaatctaac | 1620 |
| gtcggaaaaa | ttttgcgacg | agaattacgt | gacgaagcgc | gcggcaaagt | ggacaataaa | 1680 | gcctga 1686

<210> SEQ ID NO 12
<211> LENGTH: 561
<212> TYPE: PRT
<213> ORGANISM: Escherichia coli

<400> SEQUENCE: 12

Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Gly Met Pro
                325                 330                 335

Val Gln Gln Val Val Ala Glu Arg Trp Val Lys Leu Thr Gly Gln Tyr
            340                 345                 350

Leu Leu Glu Gly Tyr Gly Leu Thr Glu Cys Ala Pro Leu Val Ser Val
        355                 360                 365

```
Asn Pro Tyr Asp Ile Asp Tyr His Ser Gly Ser Ile Gly Leu Pro Val
        370                 375                 380

Pro Ser Thr Glu Ala Lys Leu Val Asp Asp Asp Asn Glu Val Pro
385                 390                 395                 400

Pro Gly Gln Pro Gly Glu Leu Cys Val Lys Gly Pro Gln Val Met Leu
                405                 410                 415

Gly Tyr Trp Gln Arg Pro Asp Ala Thr Asp Glu Ile Ile Lys Asn Gly
                420                 425                 430

Trp Leu His Thr Gly Asp Ile Ala Val Met Asp Glu Glu Gly Phe Leu
            435                 440                 445

Arg Ile Val Asp Arg Lys Lys Asp Met Ile Leu Val Ser Gly Phe Asn
        450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Gly Glu Ala
                485                 490                 495

Val Lys Ile Phe Val Val Lys Lys Asp Pro Ser Leu Thr Glu Glu Ser
                500                 505                 510

Leu Val Thr Phe Cys Arg Arg Gln Leu Thr Gly Tyr Lys Val Pro Lys
            515                 520                 525

Leu Val Glu Phe Arg Asp Glu Leu Pro Lys Ser Asn Val Gly Lys Ile
        530                 535                 540

Leu Arg Arg Glu Leu Arg Asp Glu Ala Arg Gly Lys Val Asp Asn Lys
545                 550                 555                 560

Ala
```

<210> SEQ ID NO 13
<211> LENGTH: 1683
<212> TYPE: DNA
<213> ORGANISM: Pseudomonas putida

<400> SEQUENCE: 13

```
atgttgcaga cacgcatcat caagcccgcc gagggcgcct atgcctatcc attgctgatc    60
aagcgcctgc tgatgtccgg cagccgctat gaaaagaccc gggaaatcgt ctaccgcgac   120
cagatgcggc tgacgtatcc acagctcaac gagcgcattg cccgcctggc aacgtgctg   180
accgaggccg ggtcaaggc cggtgacacc gtggcggtga tggactggga cagccatcgc   240
tacctggaat gcatgttcgc catcccgatg atcggcgctg tggtgcacac catcaacgtg   300
cgcctgtcgc ccgagcagat cctctacacc atgaaccatg ccgaagaccg cgtggtgctg   360
gtcaacagcg acttcgtcgg cctgtaccag gccatcgccg gcagctgac cactgtcgac   420
aagaccctgc tactgaccga tggcccggac aagactgccg aactgccggg tctggtcggc   480
gagtatgagc agctgctggc tgctgccagc ccgcgctacg acttcccgga tttcgacgag   540
aattcggtgg ccactaccct ctacaccact ggcaccaccg gtaaccccaa gggcgtgtat   600
ttcagtcacc gccagctggt gctgcacacc ctggccgagg cctcggtcac cggcagtatc   660
gacagcgtgc gcctgctggg cagcaacgat gtgtacatgc ccatcacccc gatgttccac   720
gtgcatgcct gggcatccc ctacgctgcc accatgctcg gcatgaagca ggtgtaccca   780
gggcgctacg agccggacat gctggtcaag ctttggcgtg aagagaaggt cactttctcc   840
cactgcgtgc cgaccatcct gcagatgctg ctcaactgcc cgaacgccca ggggcaggac   900
ttcggcggct ggaagatcat catcggcggc agctcgctca accgttcgct gtaccaggcc   960
```

```
gccctggcgc gcggcatcca gctgaccgcc gcgtatggca tgtcggaaac ctgcccgctg    1020
atctccgcgg cacacctgaa cgatgaactg caggccggca gcgaggatga gcgcgtcact    1080
taccgtatca aggccggtgt gccggtgccg ttggtcgaag cggccatcgt cgacggcgaa    1140
ggcaacttcc tgcccgccga tgtgaaaacc cagggcgagc tggtactgcg tgcgccgtgg    1200
ctgaccatgg gctacttcaa ggagccggag aagagcgagg agctgtggca gggcggctgg    1260
ctgcacaccg gtgacgtcgc caccctcgac ggcatgggct acatcgacat ccgcgaccgc    1320
atcaaggatg tgatcaagac cggtggcgag tgggtttcct cgctcgacct ggaagacctg    1380
atcagccgcc acccggccgt gcgcgaagtg gcggtggtgg gggtggccga cccgcagtgg    1440
ggtgagcgcc cgtttgccct gctggtggca cgtgacggcc acgatatcga cgccaaggcg    1500
ctgaaggaac acctcaagcc attcgtcgag caaggtcata tcaacaagtg gcgattcca     1560
agccagatcg cccttgttac tgaaattccc aagaccagtg tcggcaagct cgacaagaaa    1620
cgcattcgcc aggacatcgt ccagtggcag gccagcaaca gcgcgttcct ttccacgttg    1680
taa                                                                  1683
```

<210> SEQ ID NO 14
<211> LENGTH: 560
<212> TYPE: PRT
<213> ORGANISM: Pseudomonas putida

<400> SEQUENCE: 14

```
Met Leu Gln Thr Arg Ile Ile Lys Pro Ala Glu Gly Ala Tyr Ala Tyr
1               5                   10                  15

Pro Leu Leu Ile Lys Arg Leu Leu Met Ser Gly Ser Arg Tyr Glu Lys
            20                  25                  30

Thr Arg Glu Ile Val Tyr Arg Asp Gln Met Arg Leu Thr Tyr Pro Gln
        35                  40                  45

Leu Asn Glu Arg Ile Ala Arg Leu Ala Asn Val Leu Thr Glu Ala Gly
    50                  55                  60

Val Lys Ala Gly Asp Thr Val Ala Val Met Asp Trp Asp Ser His Arg
65                  70                  75                  80

Tyr Leu Glu Cys Met Phe Ala Ile Pro Met Ile Gly Ala Val His
                85                  90                  95

Thr Ile Asn Val Arg Leu Ser Pro Glu Gln Ile Leu Tyr Thr Met Asn
            100                 105                 110

His Ala Glu Asp Arg Val Val Leu Val Asn Ser Asp Phe Val Gly Leu
        115                 120                 125

Tyr Gln Ala Ile Ala Gly Gln Leu Thr Thr Val Asp Lys Thr Leu Leu
    130                 135                 140

Leu Thr Asp Gly Pro Asp Lys Thr Ala Glu Leu Pro Gly Leu Val Gly
145                 150                 155                 160

Glu Tyr Glu Gln Leu Leu Ala Ala Ala Ser Pro Arg Tyr Asp Phe Pro
                165                 170                 175

Asp Phe Asp Glu Asn Ser Val Ala Thr Thr Phe Tyr Thr Thr Gly Thr
            180                 185                 190

Thr Gly Asn Pro Lys Gly Val Tyr Phe Ser His Arg Gln Leu Val Leu
        195                 200                 205

His Thr Leu Ala Glu Ala Ser Val Thr Gly Ser Ile Asp Ser Val Arg
    210                 215                 220

Leu Leu Gly Ser Asn Asp Val Tyr Met Pro Ile Thr Pro Met Phe His
225                 230                 235                 240
```

Val His Ala Trp Gly Ile Pro Tyr Ala Ala Thr Met Leu Gly Met Lys
            245                 250                 255

Gln Val Tyr Pro Gly Arg Tyr Glu Pro Asp Met Leu Val Lys Leu Trp
        260                 265                 270

Arg Glu Glu Lys Val Thr Phe Ser His Cys Val Pro Thr Ile Leu Gln
    275                 280                 285

Met Leu Leu Asn Cys Pro Asn Ala Gln Gly Gln Asp Phe Gly Gly Trp
290                 295                 300

Lys Ile Ile Ile Gly Ser Ser Leu Asn Arg Ser Leu Tyr Gln Ala
305                 310                 315                 320

Ala Leu Ala Arg Gly Ile Gln Leu Thr Ala Ala Tyr Gly Met Ser Glu
                325                 330                 335

Thr Cys Pro Leu Ile Ser Ala Ala His Leu Asn Asp Glu Leu Gln Ala
            340                 345                 350

Gly Ser Glu Asp Glu Arg Val Thr Tyr Arg Ile Lys Ala Gly Val Pro
        355                 360                 365

Val Pro Leu Val Glu Ala Ala Ile Val Asp Gly Glu Gly Asn Phe Leu
370                 375                 380

Pro Ala Asp Gly Glu Thr Gln Gly Glu Leu Val Leu Arg Ala Pro Trp
385                 390                 395                 400

Leu Thr Met Gly Tyr Phe Lys Glu Pro Glu Lys Ser Glu Glu Leu Trp
                405                 410                 415

Gln Gly Gly Trp Leu His Thr Gly Asp Val Ala Thr Leu Asp Gly Met
            420                 425                 430

Gly Tyr Ile Asp Ile Arg Asp Arg Ile Lys Asp Val Ile Lys Thr Gly
        435                 440                 445

Gly Glu Trp Val Ser Ser Leu Asp Leu Glu Asp Leu Ile Ser Arg His
    450                 455                 460

Pro Ala Val Arg Glu Val Ala Val Val Gly Val Ala Asp Pro Gln Trp
465                 470                 475                 480

Gly Glu Arg Pro Phe Ala Leu Leu Val Ala Arg Asp Gly His Asp Ile
                485                 490                 495

Asp Ala Lys Ala Leu Lys Glu His Leu Lys Pro Phe Val Glu Gln Gly
            500                 505                 510

His Ile Asn Lys Trp Ala Ile Pro Ser Gln Ile Ala Leu Val Thr Glu
        515                 520                 525

Ile Pro Lys Thr Ser Val Gly Lys Leu Asp Lys Lys Arg Ile Arg Gln
    530                 535                 540

Asp Ile Val Gln Trp Gln Ala Ser Asn Ser Ala Phe Leu Ser Thr Leu
545                 550                 555                 560

<210> SEQ ID NO 15
<211> LENGTH: 858
<212> TYPE: DNA
<213> ORGANISM: Pseudomonas aeruginosa

<400> SEQUENCE: 15
atgcccaccg cctggctcga cctgcccgcc ccacccgccc tgcccggcct gttcctgcgc     60
gccgcactgc gccgcggcat ccgcggcaag gccctgcccg agcgcggcct gcgcagccag    120
gtcacggtgg acccgaagca cctcgagcgc taccgccagg tctgcggctt ccgcgacgac    180
ggcctgctgc cgccgaccta ccgcacatc ctcgccttcc cgctgcagat ggcgctgctc    240
accgacaagc gcttcccctt cccgctgctc ggcctggtcc acctggagaa ccgcatcgac    300
gtgctgcgcg cgctcggcgg cctcggcccg ttcaccgtga gcgtcgcggt ggaaaacctg    360

```
caaccgcacg acaagggcgc caccttcagc atcgtcaccc gcctggaaga ccagcttggc    420
ctgctctggg tcggcgacag caaggtgctc tgccgcggcg tcaaggtgcc cggcgaaatt    480
ccgccgaaag ccgagcagga gccgctgccg ctggagccgg tcgacaactg gaaggcgccc    540
gccgacatcg gccggcgcta tgcccgtgcc gccggcgact acaacccgat ccacctgtcg    600
gcgcccagcg ccaagctgtt cggctttccc cgcgccatcg cccacggcct gtggaacaag    660
gctcgcagcc tggccgccct cggcgagcga ctgccagcct cgggctatcg ggtcgaggtg    720
cgcttccaga agccagtgct gctgccggcc agcctcaccc tcctggccag cgcggcggcg    780
gcggacggcc agttcagcct gcgcggcaag gacgacctgc cgcacatggc cgggcattgg    840
agccggctac agggctga                                                  858
```

```
<210> SEQ ID NO 16
<211> LENGTH: 285
<212> TYPE: PRT
<213> ORGANISM: Pseudomonas aeruginosa

<400> SEQUENCE: 16

Met Pro Thr Ala Trp Leu Asp Leu Pro Ala Pro Ala Leu Pro Gly
1               5                   10                  15

Leu Phe Leu Arg Ala Ala Leu Arg Arg Gly Ile Arg Gly Lys Ala Leu
                20                  25                  30

Pro Glu Arg Gly Leu Arg Ser Gln Val Thr Val Asp Pro Lys His Leu
            35                  40                  45

Glu Arg Tyr Arg Gln Val Cys Gly Phe Arg Asp Asp Gly Leu Leu Pro
        50                  55                  60

Pro Thr Tyr Pro His Ile Leu Ala Phe Pro Leu Gln Met Ala Leu Leu
65                  70                  75                  80

Thr Asp Lys Arg Phe Pro Phe Pro Leu Leu Gly Leu Val His Leu Glu
                85                  90                  95

Asn Arg Ile Asp Val Leu Arg Ala Leu Gly Gly Leu Gly Pro Phe Thr
            100                 105                 110

Val Ser Val Ala Val Glu Asn Leu Gln Pro His Asp Lys Gly Ala Thr
        115                 120                 125

Phe Ser Ile Val Thr Arg Leu Glu Asp Gln Leu Gly Leu Leu Trp Val
    130                 135                 140

Gly Asp Ser Lys Val Leu Cys Arg Gly Val Lys Val Pro Gly Glu Ile
145                 150                 155                 160

Pro Pro Lys Ala Glu Gln Glu Pro Leu Pro Leu Glu Pro Val Asp Asn
                165                 170                 175

Trp Lys Ala Pro Ala Asp Ile Gly Arg Arg Tyr Ala Arg Ala Ala Gly
            180                 185                 190

Asp Tyr Asn Pro Ile His Leu Ser Ala Pro Ser Ala Lys Leu Phe Gly
        195                 200                 205

Phe Pro Arg Ala Ile Ala His Gly Leu Trp Asn Lys Ala Arg Ser Leu
    210                 215                 220

Ala Ala Leu Gly Glu Arg Leu Pro Ala Ser Gly Tyr Arg Val Glu Val
225                 230                 235                 240

Arg Phe Gln Lys Pro Val Leu Leu Pro Ala Ser Leu Thr Leu Leu Ala
                245                 250                 255

Ser Ala Ala Ala Ala Asp Gly Gln Phe Ser Leu Arg Gly Lys Asp Asp
            260                 265                 270

Leu Pro His Met Ala Gly His Trp Ser Arg Leu Gln Gly
        275                 280                 285
```

<210> SEQ ID NO 17
<211> LENGTH: 1683
<212> TYPE: DNA
<213> ORGANISM: Pseudomonas aeruginosa

<400> SEQUENCE: 17

```
atgcgagaaa agcaggaatc gggtagcgtg ccggtgcccg ccgagttcat gagtgcacag      60
agcgccatcg tcggcctgcg cggcaaggac ctgctgacga cggtccgcag cctggctgtc     120
cacggcctgc gccagccgct gcacagtgcg cggcacctgg tcgccttcgg aggccagttg     180
ggcaaggtgc tgctgggcga caccctgcac cagccgaacc cacaggacgc ccgcttccag     240
gatccatcct ggcgcctcaa tcccttctac cggcgcaccc tgcaggccta cctggcgtgg     300
cagaaacaac tgctcgcctg gatcgacgaa agcaacctgg actgcgacga tcgcgcccgc     360
gcccgcttcc tcgtcgcctt gctctccgac gccgtggcac ccagcaacag cctgatcaat     420
ccactggcgt taaaggaact gttcaatacc ggcgggatca gcctgctcaa tggcgtccgc     480
cacctgctcg aagacctggt gcacaacggc ggcatgccca gccaggtgaa caagaccgcc     540
ttcgagatcg tcgcaacct cgccaccacg caaggcgcgg tggtgttccg caacgaggtg     600
ctggagctga tccagtacaa gccgctgggc gagcgccagt acgccaagcc cctgctgatc     660
gtgccgccgc agatcaacaa gtactacatc ttcgacctgt cgccggaaaa gagcttcgtc     720
cagtacgccc tgaagaacaa cctgcaggtc ttcgtcatca gttggcgcaa ccccgacgcc     780
cagcaccgcg aatggggcct gagcacctat gtcgaggccc tcgaccaggc catcgaggtc     840
agccgcgaga tcaccggcag ccgcagcgtg aacctggccg gcgcctgcgc cggcgggctc     900
accgtagccg ccttgctcgg ccacctgcag gtgcgccggc aactgcgcaa ggtcagtagc     960
gtcacctacc tggtcagcct gctcgacagc cagatggaaa gcccggcgat gctcttcgcc    1020
gacgagcaga ccctggagag cagcaagcgc cgctcctacc agcatggcgt gctggacggg    1080
cgcgacatgg ccaaggtgtt cgcctggatg cgccccaacg acctgatctg gaactactgg    1140
gtcaacaact acctgctcgg caggcagccg ccggcgttcg acatcctcta ctggaacaac    1200
gacaacacgc ggctgcccgc ggcgttccac ggcgaactgc tcgacctgtt caagcacaac    1260
ccgctgaccc gccgggcgc gctggaggtc agcgggaccg cggtggacct gggcaaggtg    1320
gcgatcgaca gcttccacgt cgccggcatc accgaccaca tcacgccctg ggacgcggtg    1380
tatcgctcgg ccctcctgct gggcggccag cgccgcttca tcctgtccaa cagcgggcac    1440
atccagagca tcctcaaccc tcccggaaac cccaaggcct gctacttcga aacgacaag    1500
ctgagcagcg atcacgcgc ctggtactac gacgccaagc gcgaagaggg cagctggtgg    1560
ccggtctggc tgggctggct gcaggagcgc tcgggcgagc tgggcaaccc tgacttcaac    1620
cttggcagcg ccgcgcatcc gccccctcgaa gcggccccgg gcacctacgt gcatatacgc    1680
tga                                                                  1683
```

<210> SEQ ID NO 18
<211> LENGTH: 560
<212> TYPE: PRT
<213> ORGANISM: Pseudomonas aeruginosa

<400> SEQUENCE: 18

```
Met Arg Glu Lys Gln Glu Ser Gly Ser Val Pro Val Pro Ala Glu Phe
1               5                   10                  15
```

```
Met Ser Ala Gln Ser Ala Ile Val Gly Leu Arg Gly Lys Asp Leu Leu
             20                  25                  30

Thr Thr Val Arg Ser Leu Ala Val His Gly Leu Arg Gln Pro Leu His
         35                  40                  45

Ser Ala Arg His Leu Val Ala Phe Gly Gly Gln Leu Gly Lys Val Leu
 50                  55                  60

Leu Gly Asp Thr Leu His Gln Pro Asn Pro Gln Asp Ala Arg Phe Gln
 65                  70                  75                  80

Asp Pro Ser Trp Arg Leu Asn Pro Phe Tyr Arg Arg Thr Leu Gln Ala
                 85                  90                  95

Tyr Leu Ala Trp Gln Lys Gln Leu Leu Ala Trp Ile Asp Glu Ser Asn
            100                 105                 110

Leu Asp Cys Asp Asp Arg Ala Arg Ala Arg Phe Leu Val Ala Leu Leu
        115                 120                 125

Ser Asp Ala Val Ala Pro Ser Asn Ser Leu Ile Asn Pro Leu Ala Leu
    130                 135                 140

Lys Glu Leu Phe Asn Thr Gly Gly Ile Ser Leu Leu Asn Gly Val Arg
145                 150                 155                 160

His Leu Leu Glu Asp Leu Val His Asn Gly Gly Met Pro Ser Gln Val
                165                 170                 175

Asn Lys Thr Ala Phe Glu Ile Gly Arg Asn Leu Ala Thr Thr Gln Gly
            180                 185                 190

Ala Val Val Phe Arg Asn Glu Val Leu Glu Leu Ile Gln Tyr Lys Pro
        195                 200                 205

Leu Gly Glu Arg Gln Tyr Ala Lys Pro Leu Leu Ile Val Pro Pro Gln
    210                 215                 220

Ile Asn Lys Tyr Tyr Ile Phe Asp Leu Ser Pro Glu Lys Ser Phe Val
225                 230                 235                 240

Gln Tyr Ala Leu Lys Asn Asn Leu Gln Val Phe Val Ile Ser Trp Arg
                245                 250                 255

Asn Pro Asp Ala Gln His Arg Glu Trp Gly Leu Ser Thr Tyr Val Glu
            260                 265                 270

Ala Leu Asp Gln Ala Ile Glu Val Ser Arg Glu Ile Thr Gly Ser Arg
        275                 280                 285

Ser Val Asn Leu Ala Gly Ala Cys Ala Gly Gly Leu Thr Val Ala Ala
    290                 295                 300

Leu Leu Gly His Leu Gln Val Arg Arg Gln Leu Arg Lys Val Ser Ser
305                 310                 315                 320

Val Thr Tyr Leu Val Ser Leu Leu Asp Ser Gln Met Glu Ser Pro Ala
                325                 330                 335

Met Leu Phe Ala Asp Glu Gln Thr Leu Glu Ser Ser Lys Arg Arg Ser
            340                 345                 350

Tyr Gln His Gly Val Leu Asp Gly Arg Asp Met Ala Lys Val Phe Ala
        355                 360                 365

Trp Met Arg Pro Asn Asp Leu Ile Trp Asn Tyr Trp Val Asn Asn Tyr
    370                 375                 380

Leu Leu Gly Arg Gln Pro Pro Ala Phe Asp Ile Leu Tyr Trp Asn Asn
385                 390                 395                 400

Asp Asn Thr Arg Leu Pro Ala Ala Phe His Gly Glu Leu Leu Asp Leu
                405                 410                 415

Phe Lys His Asn Pro Leu Thr Arg Pro Gly Ala Leu Glu Val Ser Gly
            420                 425                 430

Thr Ala Val Asp Leu Gly Lys Val Ala Ile Asp Ser Phe His Val Ala
```

```
                 435                 440                 445
Gly Ile Thr Asp His Ile Thr Pro Trp Asp Ala Val Tyr Arg Ser Ala
450                 455                 460

Leu Leu Leu Gly Gly Gln Arg Arg Phe Ile Leu Ser Asn Ser Gly His
465                 470                 475                 480

Ile Gln Ser Ile Leu Asn Pro Pro Gly Asn Pro Lys Ala Cys Tyr Phe
                485                 490                 495

Glu Asn Asp Lys Leu Ser Ser Asp Pro Arg Ala Trp Tyr Tyr Asp Ala
            500                 505                 510

Lys Arg Glu Glu Gly Ser Trp Trp Pro Val Trp Leu Gly Trp Leu Gln
        515                 520                 525

Glu Arg Ser Gly Glu Leu Gly Asn Pro Asp Phe Asn Leu Gly Ser Ala
    530                 535                 540

Ala His Pro Pro Leu Glu Ala Ala Pro Gly Thr Tyr Val His Ile Arg
545                 550                 555                 560

<210> SEQ ID NO 19
<211> LENGTH: 930
<212> TYPE: DNA
<213> ORGANISM: Umbellularia californica
<220> FEATURE:
<221> NAME/KEY: CDS
<222> LOCATION: (21)..(923)

<400> SEQUENCE: 19
cccgggagga ggattataaa atg act cta gag tgg aaa ccg aaa cca aaa ctg      53
                     Met Thr Leu Glu Trp Lys Pro Lys Pro Lys Leu
                      1               5                  10 cct caa ctg ctg gat gat cac ttc ggt ctg cac ggt ctg gtg ttt cgt     101
Pro Gln Leu Leu Asp Asp His Phe Gly Leu His Gly Leu Val Phe Arg
         15                  20                  25 cgt act ttc gca att cgt tct tat gaa gtg ggt cca gat cgt tct acc     149
Arg Thr Phe Ala Ile Arg Ser Tyr Glu Val Gly Pro Asp Arg Ser Thr
             30                  35                  40 tcc atc ctg gcc gtc atg aac cac atg cag gaa gcc acc ctg aat cac     197
Ser Ile Leu Ala Val Met Asn His Met Gln Glu Ala Thr Leu Asn His
     45                  50                  55 gcg aaa tct gtt ggt atc ctg ggt gat ggt ttc ggc act act ctg gaa     245
Ala Lys Ser Val Gly Ile Leu Gly Asp Gly Phe Gly Thr Thr Leu Glu
 60                  65                  70                  75 atg tct aaa cgt gac ctg atg tgg gta gtg cgc cgc acc cac gta gca     293
Met Ser Lys Arg Asp Leu Met Trp Val Val Arg Arg Thr His Val Ala
                 80                  85                  90 gta gag cgc tac cct act tgg ggt gac act gtg gaa gtc gag tgt tgg     341
Val Glu Arg Tyr Pro Thr Trp Gly Asp Thr Val Glu Val Glu Cys Trp
             95                 100                 105 att ggc gcg tcc ggt aac aat ggt atg cgt cgc gat ttt ctg gtc cgt     389
Ile Gly Ala Ser Gly Asn Asn Gly Met Arg Arg Asp Phe Leu Val Arg
        110                 115                 120 gac tgt aaa acg ggc gaa atc ctg acg cgt tgc acc tcc ctg agc gtt     437
Asp Cys Lys Thr Gly Glu Ile Leu Thr Arg Cys Thr Ser Leu Ser Val
    125                 130                 135 ctg atg aac acc cgc act cgt cgc ctg tct acc atc ccg gac gaa gtg     485
Leu Met Asn Thr Arg Thr Arg Arg Leu Ser Thr Ile Pro Asp Glu Val
140                 145                 150                 155 cgc ggt gag atc ggt cct gct ttc atc gat aac gtg gca gtt aaa gac     533
Arg Gly Glu Ile Gly Pro Ala Phe Ile Asp Asn Val Ala Val Lys Asp
                160                 165                 170 gac gaa atc aag aaa ctg caa aaa ctg aac gac tcc acc gcg gac tac     581
```

-continued

```
                    Asp Glu Ile Lys Lys Leu Gln Lys Leu Asn Asp Ser Thr Ala Asp Tyr
                                    175                 180                 185 atc cag ggc ggt ctg act ccg cgc tgg aac gac ctg gat gtt aat cag          629
Ile Gln Gly Gly Leu Thr Pro Arg Trp Asn Asp Leu Asp Val Asn Gln
        190                 195                 200 cat gtg aac aac ctg aaa tac gtt gct tgg gtc ttc gag act gtg ccg          677
His Val Asn Asn Leu Lys Tyr Val Ala Trp Val Phe Glu Thr Val Pro
205                 210                 215 gac agc att ttc gaa agc cat cac att tcc tct ttt act ctg gag tac          725
Asp Ser Ile Phe Glu Ser His His Ile Ser Ser Phe Thr Leu Glu Tyr
220                 225                 230                 235 cgt cgc gaa tgt act cgc gac tcc gtt ctg cgc agc ctg acc acc gta          773
Arg Arg Glu Cys Thr Arg Asp Ser Val Leu Arg Ser Leu Thr Thr Val
        240                 245                 250 agc ggc ggt tct agc gag gca ggt ctg gtc tgc gac cat ctg ctg caa          821
Ser Gly Gly Ser Ser Glu Ala Gly Leu Val Cys Asp His Leu Leu Gln
                255                 260                 265 ctg gaa ggc ggc tcc gaa gtc ctg cgt gcg cgt acg gag tgg cgt cca          869
Leu Glu Gly Gly Ser Glu Val Leu Arg Ala Arg Thr Glu Trp Arg Pro
        270                 275                 280 aag ctg acg gat tct ttc cgc ggc atc tcc gta att ccg gcg gaa cct          917
Lys Leu Thr Asp Ser Phe Arg Gly Ile Ser Val Ile Pro Ala Glu Pro
285                 290                 295 cgt gtt taagctt                                                           930
Arg Val
300

<210> SEQ ID NO 20
<211> LENGTH: 301
<212> TYPE: PRT
<213> ORGANISM: Umbellularia californica

<400> SEQUENCE: 20

Met Thr Leu Glu Trp Lys Pro Lys Pro Lys Leu Pro Gln Leu Leu Asp
1               5                   10                  15

Asp His Phe Gly Leu His Gly Leu Val Phe Arg Arg Thr Phe Ala Ile
                20                  25                  30

Arg Ser Tyr Glu Val Gly Pro Asp Arg Ser Thr Ser Ile Leu Ala Val
        35                  40                  45

Met Asn His Met Gln Glu Ala Thr Leu Asn His Ala Lys Ser Val Gly
50                  55                  60

Ile Leu Gly Asp Gly Phe Gly Thr Thr Leu Glu Met Ser Lys Arg Asp
65                  70                  75                  80

Leu Met Trp Val Val Arg Arg Thr His Val Ala Val Glu Arg Tyr Pro
                85                  90                  95

Thr Trp Gly Asp Thr Val Glu Val Glu Cys Trp Ile Gly Ala Ser Gly
        100                 105                 110

Asn Asn Gly Met Arg Arg Asp Phe Leu Val Arg Asp Cys Lys Thr Gly
        115                 120                 125

Glu Ile Leu Thr Arg Cys Thr Ser Leu Ser Val Leu Met Asn Thr Arg
    130                 135                 140

Thr Arg Arg Leu Ser Thr Ile Pro Asp Glu Val Arg Gly Glu Ile Gly
145                 150                 155                 160

Pro Ala Phe Ile Asp Asn Val Ala Val Lys Asp Asp Glu Ile Lys Lys
                165                 170                 175

Leu Gln Lys Leu Asn Asp Ser Thr Ala Asp Tyr Ile Gln Gly Gly Leu
        180                 185                 190
```

```
Thr Pro Arg Trp Asn Asp Leu Asp Val Asn Gln His Val Asn Asn Leu
        195                 200                 205

Lys Tyr Val Ala Trp Val Phe Glu Thr Val Pro Asp Ser Ile Phe Glu
    210                 215                 220

Ser His His Ile Ser Ser Phe Thr Leu Glu Tyr Arg Arg Glu Cys Thr
225                 230                 235                 240

Arg Asp Ser Val Leu Arg Ser Leu Thr Thr Val Ser Gly Gly Ser Ser
                245                 250                 255

Glu Ala Gly Leu Val Cys Asp His Leu Gln Leu Glu Gly Gly Ser
                260                 265                 270

Glu Val Leu Arg Ala Arg Thr Glu Trp Arg Pro Lys Leu Thr Asp Ser
            275                 280                 285

Phe Arg Gly Ile Ser Val Ile Pro Ala Glu Pro Arg Val
        290                 295                 300

<210> SEQ ID NO 21
<211> LENGTH: 420
<212> TYPE: DNA
<213> ORGANISM: Pseudomonas putida

<400> SEQUENCE: 21
atggccaaag tgattgcgaa gaaaaagac gaagccctgg acacgcttgg cgaggtgcgc      60
ggctatgcgc gcaagatctg gctggccggt atcggcgcct acgccgcgt cggtcaggaa     120 ggcgctgact acttcaaaga gctggtcagg gcgggtgaag tgtcgagaa gcgcggcaag     180 aagcgcatcg acaaagagct cgatgcggcc aaccaccagc ttgacgaagt cggtgaagaa     240
gtgagccgcg tacgcggcaa ggtagaaatt caactcgaca agatcgaaaa agctttcgac     300
gcacgggtcg tcgcgccctt gaatcgcctg gtattccgt ctaaacatga cgttgaggcg     360
ttgtcgatca agcttgaaca gttgcatgag ctgcttgagc gcgtcgcgca caaaccataa     420

<210> SEQ ID NO 22
<211> LENGTH: 139
<212> TYPE: PRT
<213> ORGANISM: Pseudomonas putida

<400> SEQUENCE: 22

Met Ala Lys Val Ile Ala Lys Lys Asp Glu Ala Leu Asp Thr Leu
1               5                   10                  15

Gly Glu Val Arg Gly Tyr Ala Arg Lys Ile Trp Leu Ala Gly Ile Gly
            20                  25                  30

Ala Tyr Ala Arg Val Gly Gln Glu Gly Ala Asp Tyr Phe Lys Glu Leu
        35                  40                  45

Val Arg Ala Gly Glu Gly Val Glu Lys Arg Gly Lys Lys Arg Ile Asp
    50                  55                  60

Lys Glu Leu Asp Ala Ala Asn His Gln Leu Asp Glu Val Gly Glu Glu
65                  70                  75                  80

Val Ser Arg Val Arg Gly Lys Val Glu Ile Gln Leu Asp Lys Ile Glu
                85                  90                  95

Lys Ala Phe Asp Ala Arg Val Gly Arg Ala Leu Asn Arg Leu Gly Ile
            100                 105                 110

Pro Ser Lys His Asp Val Glu Ala Leu Ser Ile Lys Leu Glu Gln Leu
        115                 120                 125

His Glu Leu Leu Glu Arg Val Ala His Lys Pro
    130                 135
```

<210> SEQ ID NO 23
<211> LENGTH: 786
<212> TYPE: DNA
<213> ORGANISM: Pseudomonas putida

<400> SEQUENCE: 23

```
atggctggca agaagaacac cgaaaaagaa ggcagctcct gggtcggcgg gatcgagaaa      60
tactcccgca agatctggct ggcggggctg gtatctatt cgaagatcga ccaggacggc      120
ccgaagctgt tcgactcgct ggtgaaggat ggcgagaagg ccgagaagca ggcgaaaaag      180
acggctgaag atgttgccga gactgccaag tcttcgacca cttcgcgggt gtcgggcgtg      240
aaggaccgtg cgctgggcaa gtggagcgaa cttgaagaag ccttcgacaa gcgccttaac      300
agcgccatct cgcgccttgg cgtgccgagc cgcaacgaga tcaaggcact gcaccagcag      360
gtggacagcc tgaccaagca gatcgagaag ctgaccggtg cttcggttac gccgatttcg      420
tcgcgcgctg cagcaaccaa gccggctgca agcaaggctg cggccaagcc actggccaag      480
gcagcagcta agcctgcggc gaaaacggcg gcggccaaac tgctggcaa aaccgcagcg      540
gccaaacccg cagccaaaac cgcagcggaa aaacctgcag ctaagccagc agccaagcct      600
gcagcggcca aacctgcggc agccaagaaa cctgcggtga agaaagctcc agccaaaccg      660
gcagcggcca aaccagcagc accagctgcc agcgctgcgc ctgcagcgac cacagcaccg      720
gcaactgccg ccaccccggc cagcagcacg ccgtcggcac cgactggcac cggtaccctg      780
atctga                                                                786
```

<210> SEQ ID NO 24
<211> LENGTH: 261
<212> TYPE: PRT
<213> ORGANISM: Pseudomonas putida

<400> SEQUENCE: 24

```
Met Ala Gly Lys Lys Asn Thr Glu Lys Glu Gly Ser Ser Trp Val Gly
1               5                   10                  15

Gly Ile Glu Lys Tyr Ser Arg Lys Ile Trp Leu Ala Gly Leu Gly Ile
            20                  25                  30

Tyr Ser Lys Ile Asp Gln Asp Gly Pro Lys Leu Phe Asp Ser Leu Val
        35                  40                  45

Lys Asp Gly Glu Lys Ala Glu Lys Gln Ala Lys Lys Thr Ala Glu Asp
    50                  55                  60

Val Ala Glu Thr Ala Lys Ser Ser Thr Thr Ser Arg Val Ser Gly Val
65                  70                  75                  80

Lys Asp Arg Ala Leu Gly Lys Trp Ser Glu Leu Glu Glu Ala Phe Asp
                85                  90                  95

Lys Arg Leu Asn Ser Ala Ile Ser Arg Leu Gly Val Pro Ser Arg Asn
            100                 105                 110

Glu Ile Lys Ala Leu His Gln Gln Val Asp Ser Leu Thr Lys Gln Ile
        115                 120                 125

Glu Lys Leu Thr Gly Ala Ser Val Thr Pro Ile Ser Ser Arg Ala Ala
    130                 135                 140

Ala Thr Lys Pro Ala Ala Ser Lys Ala Ala Lys Pro Leu Ala Lys
145                 150                 155                 160

Ala Ala Ala Lys Pro Ala Ala Lys Thr Ala Ala Ala Lys Pro Ala Gly
                165                 170                 175

Lys Thr Ala Ala Ala Lys Pro Ala Ala Lys Thr Ala Ala Glu Lys Pro
            180                 185                 190
```

```
Ala Ala Lys Pro Ala Ala Lys Pro Ala Ala Lys Pro Ala Ala
        195                 200                 205

Lys Lys Pro Ala Val Lys Lys Ala Pro Ala Lys Pro Ala Ala Lys
    210                 215                 220

Pro Ala Ala Pro Ala Ala Ser Ala Ala Pro Ala Ala Thr Thr Ala Pro
225                 230                 235                 240

Ala Thr Ala Ala Thr Pro Ala Ser Ser Thr Pro Ser Ala Pro Thr Gly
                245                 250                 255

Thr Gly Thr Leu Ile
        260

<210> SEQ ID NO 25
<211> LENGTH: 48
<212> TYPE: DNA
<213> ORGANISM: Artificial Sequence
<220> FEATURE:
<223> OTHER INFORMATION: Primer

<400> SEQUENCE: 25
gacgatgaat tcaggaggta ttaataatga gccaggtcca gaacattc          48

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
gacgatggat ccggcccgac ggtagggaaa                              30

<210> SEQ ID NO 27
<211> LENGTH: 48
<212> TYPE: DNA
<213> ORGANISM: Artificial Sequence
<220> FEATURE:
<223> OTHER INFORMATION: Primer

<400> SEQUENCE: 27
gacgatgaat tcaggaggta ttaataatgg cgctcgatcc tgaggtgc          48

<210> SEQ ID NO 28
<211> LENGTH: 33
<212> TYPE: DNA
<213> ORGANISM: Artificial Sequence
<220> FEATURE:
<223> OTHER INFORMATION: Primer

<400> SEQUENCE: 28
gacgatggat cccttcgctt cagtccggcc gct                          33

<210> SEQ ID NO 29
<211> LENGTH: 47
<212> TYPE: DNA
<213> ORGANISM: Artificial Sequence
<220> FEATURE:
<223> OTHER INFORMATION: Primer

<400> SEQUENCE: 29
gacgatgaat tcaggaggta ttaataatgc ccaccgcctg gctcgac           47

<210> SEQ ID NO 30
<211> LENGTH: 33
<212> TYPE: DNA
```

<213> ORGANISM: Artificial Sequence
<220> FEATURE:
<223> OTHER INFORMATION: Primer

<400> SEQUENCE: 30
gacgaaggat cctcagccct gtagccggct cca            33

<210> SEQ ID NO 31
<211> LENGTH: 48
<212> TYPE: DNA
<213> ORGANISM: Artificial Sequence
<220> FEATURE:
<223> OTHER INFORMATION: Primer

<400> SEQUENCE: 31
gacgatgaat tcaggaggta ttaataatgc cattcgtacc cgtagcag            48

<210> SEQ ID NO 32
<211> LENGTH: 33
<212> TYPE: DNA
<213> ORGANISM: Artificial Sequence
<220> FEATURE:
<223> OTHER INFORMATION: Primer

<400> SEQUENCE: 32
gacgatggat cctcagacga agcagaggct gag            33

<210> SEQ ID NO 33
<211> LENGTH: 47
<212> TYPE: DNA
<213> ORGANISM: Artificial Sequence
<220> FEATURE:
<223> OTHER INFORMATION: Primer

<400> SEQUENCE: 33
ggggagctca ggaggtataa ttaatgagtc agaagaacaa taacgag            47

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
gggggtacct catcgttcat gcacgtaggt            30

<210> SEQ ID NO 35
<211> LENGTH: 46
<212> TYPE: DNA
<213> ORGANISM: Artificial Sequence
<220> FEATURE:
<223> OTHER INFORMATION: Primer

<400> SEQUENCE: 35
ggggagctca ggaggtataa ttaatgcgag aaaagcagga atcggg            46

<210> SEQ ID NO 36
<211> LENGTH: 32
<212> TYPE: DNA
<213> ORGANISM: Artificial Sequence
<220> FEATURE:
<223> OTHER INFORMATION: Primer

<400> SEQUENCE: 36
gggggtacct cagcgtatat gcacgtaggt gc            32

<210> SEQ ID NO 37
<211> LENGTH: 46
<212> TYPE: DNA
<213> ORGANISM: Artificial Sequence
<220> FEATURE:
<223> OTHER INFORMATION: Primer

<400> SEQUENCE: 37
gggtctagaa ggaggtataa ttaatgcgag aaaagcagga atcggg         46

<210> SEQ ID NO 38
<211> LENGTH: 32
<212> TYPE: DNA
<213> ORGANISM: Artificial Sequence
<220> FEATURE:
<223> OTHER INFORMATION: Primer

<400> SEQUENCE: 38
gggaagcttt cagcgtatat gcacgtaggt gc         32

<210> SEQ ID NO 39
<211> LENGTH: 44
<212> TYPE: DNA
<213> ORGANISM: Artificial Sequence
<220> FEATURE:
<223> OTHER INFORMATION: Primer

<400> SEQUENCE: 39
gggggtacca ggaggtataa ttaatgttgc agacacgcat catc         44

<210> SEQ ID NO 40
<211> LENGTH: 30
<212> TYPE: DNA
<213> ORGANISM: Artificial Sequence
<220> FEATURE:
<223> OTHER INFORMATION: Primer

<400> SEQUENCE: 40
gggtctagat tacaacgtgg aaaggaacgc         30

<210> SEQ ID NO 41
<211> LENGTH: 60
<212> TYPE: DNA
<213> ORGANISM: Artificial Sequence
<220> FEATURE:
<223> OTHER INFORMATION: Primer

<400> SEQUENCE: 41
ggtcagacca ctttatttat tttttacag gggagtgtta gcggcatgcg ttcctattcc         60

<210> SEQ ID NO 42
<211> LENGTH: 60
<212> TYPE: DNA
<213> ORGANISM: Artificial Sequence
<220> FEATURE:
<223> OTHER INFORMATION: Primer

<400> SEQUENCE: 42
ctccgccatt cagcgcggat tcatatagct ttgaccttct taaacacgag gttccgccgg         60

<210> SEQ ID NO 43
<211> LENGTH: 60
<212> TYPE: DNA
<213> ORGANISM: Artificial Sequence
<220> FEATURE:

<223> OTHER INFORMATION: Primer

<400> SEQUENCE: 43
gagtccaact tgtttttgct gtgttatgga aatctcacta gcggcatgcg ttcctattcc    60

<210> SEQ ID NO 44
<211> LENGTH: 60
<212> TYPE: DNA
<213> ORGANISM: Artificial Sequence
<220> FEATURE:
<223> OTHER INFORMATION: Primer

<400> SEQUENCE: 44
acccctcgtt tgaggggttt gctctttaaa cggaagggat taaacacgag gttccgccgg    60

<210> SEQ ID NO 45
<211> LENGTH: 32
<212> TYPE: DNA
<213> ORGANISM: Artificial Sequence
<220> FEATURE:
<223> OTHER INFORMATION: Primer

<400> SEQUENCE: 45
gggctcgagt taaccggcac ggaactcgct cg                                  32

<210> SEQ ID NO 46
<211> LENGTH: 36
<212> TYPE: DNA
<213> ORGANISM: Artificial Sequence
<220> FEATURE:
<223> OTHER INFORMATION: Primer

<400> SEQUENCE: 46
gggctcgagt tggtaacgaa tcagacaatt gacggc                              36

<210> SEQ ID NO 47
<211> LENGTH: 70
<212> TYPE: DNA
<213> ORGANISM: Artificial Sequence
<220> FEATURE:
<223> OTHER INFORMATION: Primer

<400> SEQUENCE: 47
tgaataattg cttgttttta agaaaaaga aacagcggct ggtccgctgt gtgtaggctg     60
gagctgcttc                                                           70

<210> SEQ ID NO 48
<211> LENGTH: 41
<212> TYPE: DNA
<213> ORGANISM: Artificial Sequence
<220> FEATURE:
<223> OTHER INFORMATION: Primer

<400> SEQUENCE: 48
tcgatggtgt caacgtaaat gattccgggg atccgtcgac c                        41

<210> SEQ ID NO 49
<211> LENGTH: 21
<212> TYPE: DNA
<213> ORGANISM: Artificial Sequence
<220> FEATURE:
<223> OTHER INFORMATION: Primer

<400> SEQUENCE: 49
catttacgtt gacaccatcg a                                              21

```
<210> SEQ ID NO 50
<211> LENGTH: 22
<212> TYPE: DNA
<213> ORGANISM: Artificial Sequence
<220> FEATURE:
<223> OTHER INFORMATION: Primer

<400> SEQUENCE: 50
tcaggcttta ttgtccactt tg                                              22

<210> SEQ ID NO 51
<211> LENGTH: 63
<212> TYPE: DNA
<213> ORGANISM: Artificial Sequence
<220> FEATURE:
<223> OTHER INFORMATION: Primer

<400> SEQUENCE: 51
caggtcagac cactttattt attttttac aggggagtgt gaagcggcat gcgttcctat      60
tcc                                                                   63

<210> SEQ ID NO 52
<211> LENGTH: 60
<212> TYPE: DNA
<213> ORGANISM: Artificial Sequence
<220> FEATURE:
<223> OTHER INFORMATION: Primer

<400> SEQUENCE: 52
ttgcaggtca gttgcagttg ttttccaaaa actttcccca gtgtaggctg gagctgcttc     60

<210> SEQ ID NO 53
<211> LENGTH: 63
<212> TYPE: DNA
<213> ORGANISM: Artificial Sequence
<220> FEATURE:
<223> OTHER INFORMATION: Primer

<400> SEQUENCE: 53
tctggtacga ccagatcacc ttgcggattc aggagactga gaagcggcat gcgttcctat     60
tcc                                                                   63

<210> SEQ ID NO 54
<211> LENGTH: 60
<212> TYPE: DNA
<213> ORGANISM: Artificial Sequence
<220> FEATURE:
<223> OTHER INFORMATION: Primer

<400> SEQUENCE: 54
aacccgctca aacaccgtcg caatacsctg acccagaccg gtgtaggctg gagctgcttc     60
```